(12) United States Patent
Niitsu et al.

(10) Patent No.: US 11,690,990 B2
(45) Date of Patent: Jul. 4, 2023

(54) METHOD FOR MANUFACTURING MICROPROJECTION UNIT

(71) Applicant: KAO CORPORATION, Tokyo (JP)

(72) Inventors: Takatoshi Niitsu, Utsunomiya (JP); Satoshi Ueno, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 748 days.

(21) Appl. No.: 16/620,207

(22) PCT Filed: May 31, 2018

(86) PCT No.: PCT/JP2018/021072
§ 371 (c)(1),
(2) Date: Dec. 6, 2019

(87) PCT Pub. No.: WO2018/225628
PCT Pub. Date: Dec. 13, 2018

(65) Prior Publication Data
US 2020/0129746 A1    Apr. 30, 2020

(30) Foreign Application Priority Data

Jun. 7, 2017  (JP) .................................. 2017-112348
Jun. 7, 2017  (JP) .................................. 2017-112349

(51) Int. Cl.
*A61M 37/00*     (2006.01)
*B29C 43/02*     (2006.01)
(Continued)

(52) U.S. Cl.
CPC ....... *A61M 37/0015* (2013.01); *B29C 43/021* (2013.01); *B29C 65/02* (2013.01);
(Continued)

(58) Field of Classification Search
None
See application file for complete search history.

(56) References Cited

U.S. PATENT DOCUMENTS

2002/0020688 A1   2/2002  Sherman et al.
2005/0178760 A1   8/2005  Chang et al.
(Continued)

FOREIGN PATENT DOCUMENTS

CN    101879336 A    11/2010
CN    103561936 A    2/2014
(Continued)

OTHER PUBLICATIONS

International Search Report, issued in PCT/JP2018/021072, PCT/ISA/210, dated Jul. 24, 2018.

*Primary Examiner* — Jacob T Minskey
*Assistant Examiner* — Adrianna N Konves
(74) *Attorney, Agent, or Firm* — Birch, Stewart, Kolasch & Birch, LLP

(57) ABSTRACT

A method for manufacturing a microprojection unit (10) according to the invention involves: a microprojection tool forming step of forming a microprojection tool (1) by bringing a projecting mold part (11) into contact from one surface (2D) side of a base sheet (2A) including a thermoplastic resin, and thus forming a protrusion (3) that protrudes from another surface (2U) side, and withdrawing the projecting mold part (11) from the interior of the protrusion (3); a joining step of joining the one surface (2D) side of the base sheet (2A), in which the microprojection tool (1) has been formed, and a tip end of a base component (4); and a cutting step of cutting the base sheet (2A), to which the base component (4) has been joined, along a contour (4L) of the base component (4) at a position more inward than the base component's contour (4L) in a planar view of the base sheet (2A) as viewed from the microprojection tool (1) side, to manufacture a microprojection unit (10).

20 Claims, 20 Drawing Sheets

(51) Int. Cl.
  *B29C 65/02* (2006.01)
  *B29C 65/48* (2006.01)
  *B29C 69/00* (2006.01)
  *B29K 101/12* (2006.01)
  *B29L 31/00* (2006.01)

(52) U.S. Cl.
  CPC ............ *B29C 65/48* (2013.01); *B29C 69/001* (2013.01); *A61M 2037/0023* (2013.01); *A61M 2037/0053* (2013.01); *B29C 2043/026* (2013.01); *B29C 2101/12* (2013.01); *B29L 2031/7544* (2013.01)

(56) References Cited

U.S. PATENT DOCUMENTS

| | | | |
|---|---|---|---|
| 2010/0140271 A1* | 6/2010 | Benedetti | B65D 51/228 220/361 |
| 2014/0052067 A1 | 2/2014 | Sausse et al. | |
| 2014/0154494 A1 | 6/2014 | Kato et al. | |
| 2017/0239855 A1 | 8/2017 | Niitsu et al. | |
| 2019/0030308 A1 | 1/2019 | Niitsu et al. | |

FOREIGN PATENT DOCUMENTS

| | | |
|---|---|---|
| JP | 2002-172169 A | 6/2002 |
| JP | 2003-93521 A | 4/2003 |
| JP | 2013-172833 A | 9/2013 |
| JP | 2013-236865 A | 11/2013 |
| JP | 2013-244341 A | 12/2013 |
| JP | 2014-519344 A | 8/2014 |
| JP | 2014-176568 A | 9/2014 |
| JP | 2017-35432 A | 2/2017 |
| JP | 2017-51325 A | 3/2017 |
| WO | WO 2017/130799 A1 | 8/2017 |

* cited by examiner

Fig. 4
(a)
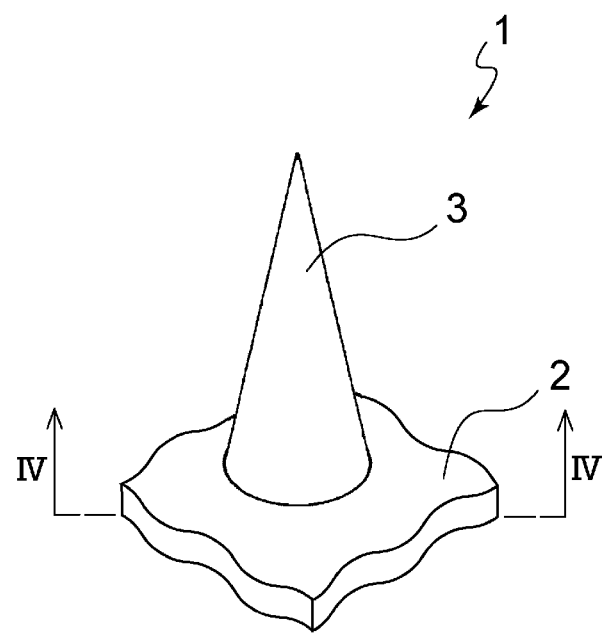
(b)
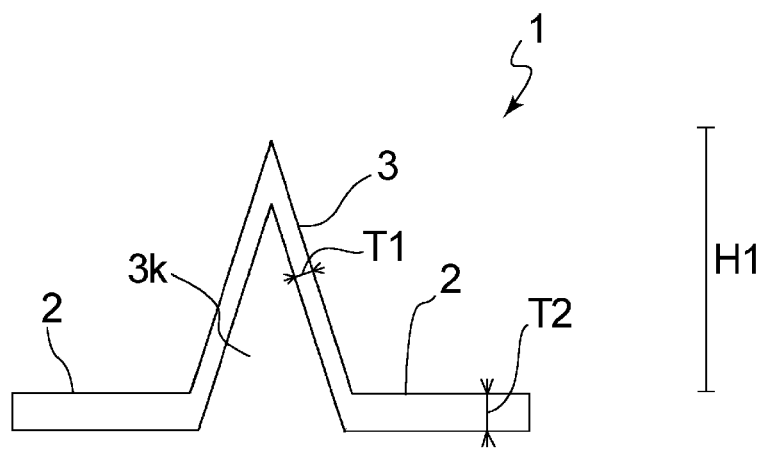

Fig. 5
(a)
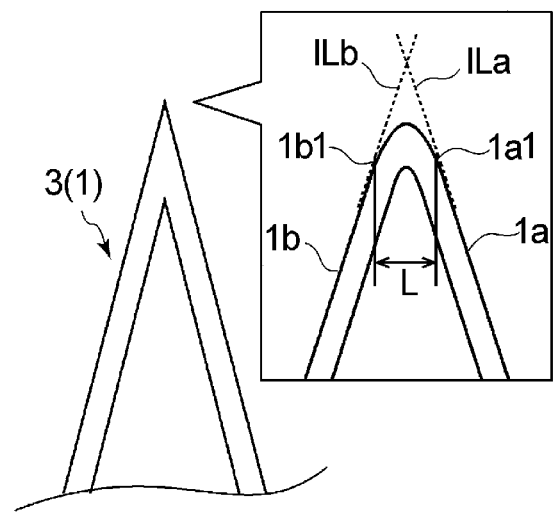
(b)
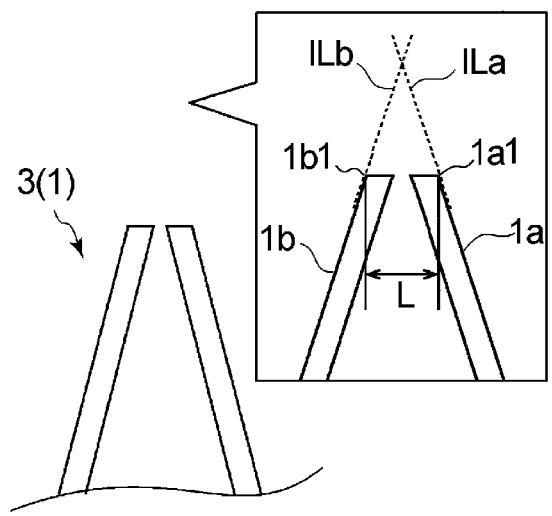

Fig.14
(a)
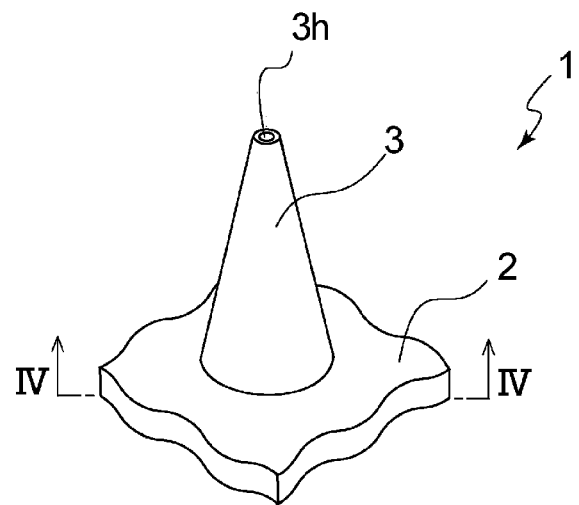
(b)
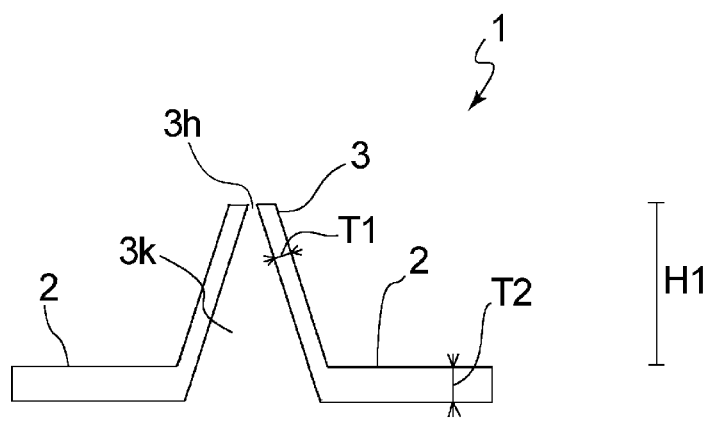

Fig.15
(a)
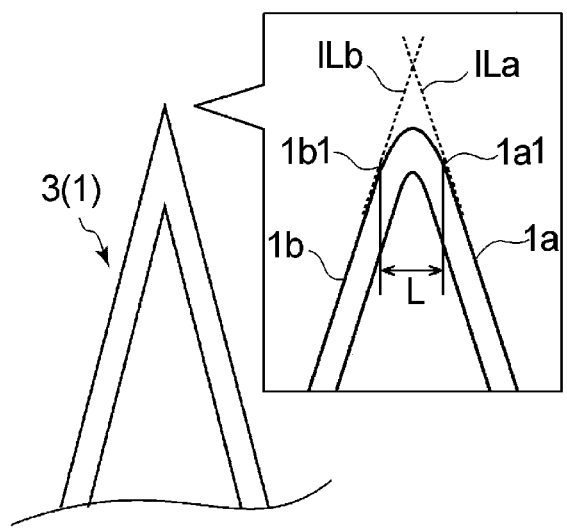
(b)
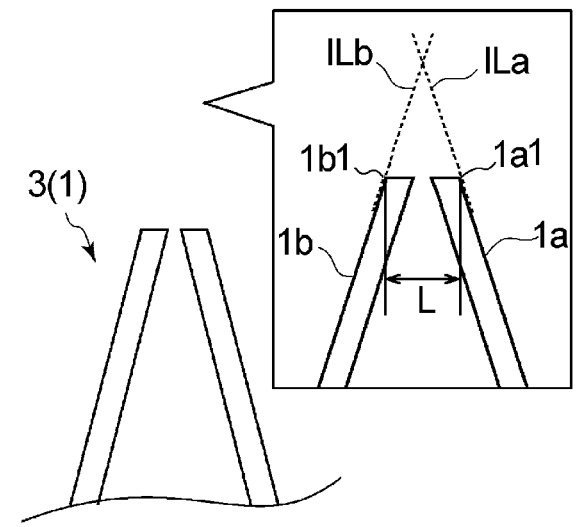

METHOD FOR MANUFACTURING MICROPROJECTION UNIT

TECHNICAL FIELD

The present invention relates to a method for manufacturing a microprojection unit, and a microprojection unit.

BACKGROUND ART

Delivery of agents by microprojections including microneedles is receiving attention in recent years, because the same performance as delivering agents with syringes can be achieved without harming the skin and with less pain.

For example, Patent Literature 1 discloses a microneedle array including microneedle groups on a base portion. Patent Literature 2 discloses a fine nozzle wherein an outwardly-projecting protrusion is provided on a bottom portion of a resin cup. Patent Literature 3 discloses a microneedle structure including microneedles on a flat bottom surface of a fluid chamber.

CITATION LIST

Patent Literature

Patent Literature 1: JP 2014-176568A
Patent Literature 2: JP 2013-172833A
Patent Literature 3: US 2002/0020688A1

SUMMARY OF INVENTION

The present invention is a method for manufacturing a microprojection unit that includes: a microprojection tool including, on a base, a protrusion with a hollow interior; and a base component having a liquid retention space that is in communication with the interior of the protrusion through the base, the microprojection tool being joined to a tip end of the base component. The present invention provides a microprojection unit manufacturing method involving: a microprojection tool forming step of forming the microprojection tool by bringing a projecting mold part into contact from one surface side of a base sheet including a thermoplastic resin, and thus forming a protrusion that protrudes from another surface side of the base sheet, and withdrawing the projecting mold part from the interior of the protrusion; a joining step of joining the one surface side of the base sheet, in which the microprojection tool has been formed, and the tip end of the base component; and a cutting step of cutting the base sheet, to which the base component has been joined, along a contour of the base component at a position more inward than the base component's contour in a planar view of the base sheet as viewed from the microprojection tool side, to thereby manufacture the microprojection unit.

Further, the present invention is a method for manufacturing a microprojection unit that includes: a microprojection tool including, on a base, a protrusion with a hollow interior; and a base component having a liquid retention space that is in communication with the interior of the protrusion through the base, the microprojection tool being joined to a tip end of the base component. The present invention provides a microprojection unit manufacturing method involving: a microprojection tool forming step of forming the microprojection tool by bringing a projecting mold part into contact from one surface side of a base sheet including a thermoplastic resin, and thus forming a protrusion that protrudes from another surface side of the base sheet, and withdrawing the projecting mold part from the interior of the protrusion; and a joining-cutting step of joining the one surface side of the base sheet, in which the microprojection tool has been formed, and the tip end of the base component, and simultaneously cutting the base sheet, along a contour of the base component at a position more inward than the base component's contour in a planar view of the base sheet as viewed from the microprojection tool side, to thereby manufacture the microprojection unit.

Further, the present invention is a microprojection unit including: a microprojection tool including, on a base, a protrusion with a hollow interior; and a base component having a liquid retention space that is in communication with the interior of the protrusion through the base, the microprojection tool being joined to a tip end of the base component. The present invention provides a microprojection unit wherein, when a liquid is introduced into the liquid retention space of the base component and inner pressure is applied, a region where the protrusion is provided in the microprojection tool's base bends so as to project outward.

BRIEF DESCRIPTION OF DRAWINGS

FIG. 4(*a*) is a perspective view of a single protrusion of the microprojection unit illustrated in FIG. 1, and FIG. 4(*b*) is a cross-sectional view taken along line Iv-Iv illustrated in FIG. 4(*a*).

FIG. 5(*a*) is an explanatory diagram illustrating a method for measuring the tip end diameter of a protrusion illustrated in FIG. 4(*b*), and FIG. 5(*b*) is an explanatory diagram illustrating a method for measuring the tip end diameter of a protrusion in cases where the protrusion has a tip-end opening.

FIG. 14(a) is a perspective view of a single protrusion of the microprojection unit illustrated in FIG. 11, and FIG. 14(b) is a cross-sectional view taken along line Iv-Iv illustrated in FIG. 14(a).

FIG. 15(a) is an explanatory diagram illustrating a method for measuring the tip end diameter of a protrusion, and FIG. 15(b) is an explanatory diagram illustrating a method for measuring the tip end diameter of a protrusion in cases where the protrusion has a tip-end opening.

DESCRIPTION OF EMBODIMENTS

The microneedle array disclosed in Patent Literature 1 is manufactured by: preparing a silicon-made master mold having fine projections by subjecting a silicon substrate to etching etc.; then preparing a shaping mold by transferring the shape of the master mold; and pouring a resin into the shaping mold. The method, which involves a step for preparing a master mold and a step for preparing a shaping mold based on the master mold, is time-consuming and leads to increased manufacturing costs.

The method for manufacturing a fine nozzle having a protrusion on a bottom portion of a resin cup as disclosed in Patent Literature 2 involves: heating an elastic element from its back surface side by using a hot plate etc.; and warming the entire bottom portion of the resin cup arranged on the elastic element. This requires time to warm the entire bottom portion of the resin cup, thus making it difficult to increase productivity. Further, the process requires warming the entire bottom portion of the resin cup arranged on the elastic element, thus making it difficult to continuously manufacture fine nozzles.

The method for manufacturing a microneedle structure disclosed in Patent Literature 3 forms microneedles by pressing a plurality of pillars, consisting of heated micropillars, directly against a flat bottom surface of a fluid chamber. This limits the shape of the fluid chamber, which serves as a section to be attached to an external cylinder.

Accordingly, the present invention relates to a microprojection unit manufacturing method for efficiently and accurately manufacturing a microprojection unit including a microprojection tool and a base component.

Further, in the microneedle array disclosed in Patent Literature 1, a needle group consisting of microneedles is formed directly on the base portion. This limits the shape of the base portion on which the microneedles are formed.

Similarly, in the microneedle disclosed in Patent Literature 2, the fine nozzle is formed directly on the bottom portion of the resin cup. This limits the shape of the bottom portion of the resin cup on which the fine nozzle is formed. Similarly, in the microneedle structure disclosed in Patent Literature 3, the microneedles are formed directly on the flat bottom surface of the fluid chamber. This limits the shape of the bottom portion of the fluid chamber.

Furthermore, Patent Literatures 1 to 3 describe nothing about causing the base etc. to bend so as to project outward when a liquid is introduced and inner pressure is applied, to thereby improve puncturability.

Accordingly, the present invention relates to a microprojection unit capable of improving puncturability.

The invention is described below according to a preferred embodiment thereof with reference to the drawings.

Figure 1:
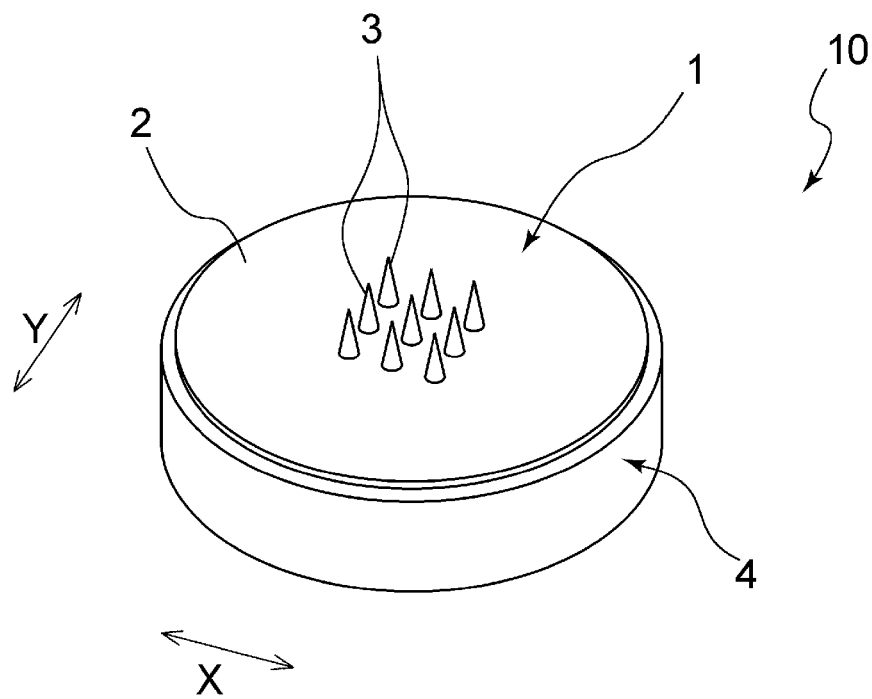
FIG. 1 is a schematic perspective view of an example of a microprojection unit manufactured by a microprojection unit manufacturing method according to the invention.

A manufacturing method of the invention is a method for manufacturing a microprojection unit in which a microprojection tool 1 is joined to a tip end of a base component 4. FIG. 1 illustrates a perspective view of a microprojection unit 10 according to an embodiment manufactured by a microprojection unit manufacturing method of the present embodiment (also referred to hereinafter simply as "microprojection unit 10"). The microprojection unit 10 includes: a microprojection tool 1 including, on a base 2, protrusions 3 with a hollow interior; and a base component 4 having a liquid retention space 4k (see FIG. 3) that is in communication with the interior of the protrusions 3 through the base 2. The microprojection unit is formed by joining the microprojection tool 1 to a tip end of the base component 4.

Figure 2:
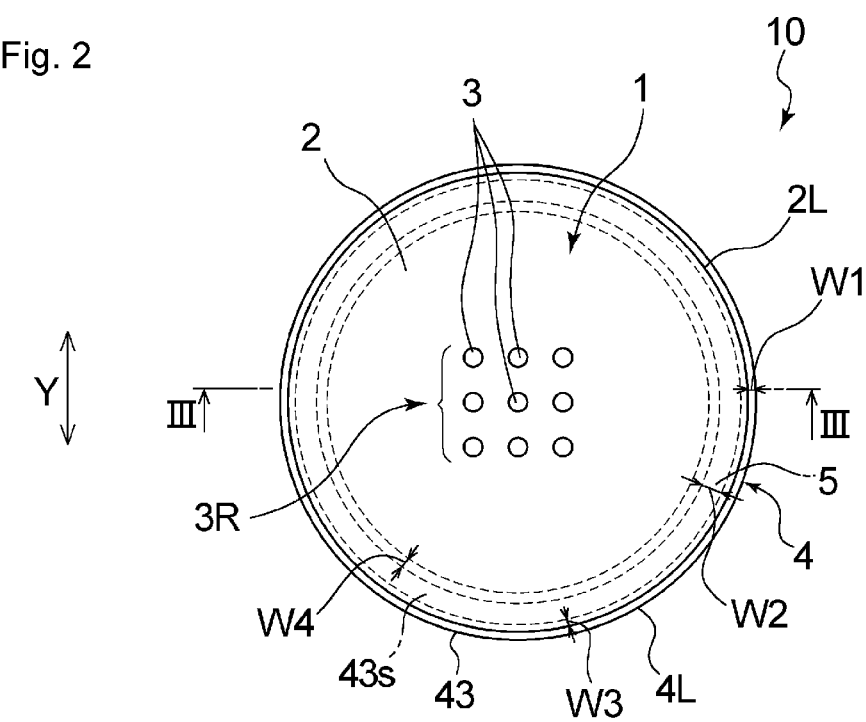
FIG. 2 is a plan view of the microprojection unit illustrated in FIG. 1 in a planar view from the microprojection tool side.

As regards the protrusions 3 of the microprojection tool 1, the number of protrusions 3, the arrangement of the protrusions 3, and the shape of the protrusion 3 are not particularly limited; in this microprojection unit 10, as illustrated in FIGS. 1 and 2, nine truncated circular-conic protrusions 3 are arranged on the upper surface of the sheet-like base 2. The arrayed nine protrusions 3 are arranged in three rows along the second direction (corresponding to the Y direction in the figures), which is the direction in which the later-described base sheet 2A is transported (corresponding to the longitudinal direction of the base sheet 2A), and in three columns along the first direction (corresponding to the X direction in the figures), which is the direction orthogonal to the second direction, i.e., the transporting direction, and which is the width direction of the base sheet 2A being transported.

Note that FIG. 4(a) is a perspective view of the microprojection tool 1, focusing on a single protrusion 3 among the protrusions 3 of the microprojection tool 1, and FIG. 4(b) is a cross-sectional view taken along line Iv-Iv illustrated in FIG. 4(a). The microprojection tool 1 illustrated in FIG. 4(a) includes: a sheet-like base 2; and a single circular-conic protrusion 3 provided so as to stand up on the base 2's upper surface (the surface on the opposite side from the base 2's surface opposing the base component 4). The microprojection tool 1 may have an opening at the tip-end side, but in this microprojection unit 10, as illustrated in FIG. 4(b), no opening is provided, and a hollow space 3k is formed so as to extend up to the interior of the protrusion 3, penetrating the base 2. In the microprojection unit 10, the interior space 3k of the protrusion 3 is formed in a circular-conic shape corresponding to the outer shape of the protrusion 3. It should be noted that, although the protrusion 3 in this microprojection unit 10 is circular-conic, the protrusion may have a shape other than a circular-conic shape, such as the shape of a truncated circular cone, a circular cylinder, a prism, a pyramid, or a truncated pyramid.

In cases where the protrusion 3 is to be used as a microneedle, in order for the tip end thereof to reach, for example, the stratum corneum, which is the outermost layer, or the dermis, which is a deeper layer, the protrusion height H1 (cf. FIG. 4(b)) of the protrusion is preferably 0.01 mm or greater, more preferably 0.02 mm or greater, and preferably 10 mm or less, more preferably 5 mm or less, further preferably 3 mm or less, and more specifically, preferably from 0.01 to 10 mm, more preferably from 0.01 to 5 mm, further preferably from 0.02 to 3 mm. The average thickness T1 of the protrusion 3 is preferably 0.005 mm or greater, more preferably 0.01 mm or greater, and preferably 1.0 mm or less, more preferably 0.5 mm or less, and more specifically, preferably from 0.005 to 1.0 mm, more preferably from 0.01 to 0.5 mm.

The tip end size, in diameter, of the protrusion 3 is preferably 0.001 mm or greater, more preferably 0.005 mm or greater, and preferably 0.5 mm or less, more preferably 0.3 mm or less, and more specifically, preferably from 0.001 to 0.5 mm, more preferably from 0.005 to 0.3 mm. The tip end diameter of the protrusion 3 of the microprojection tool 1 is measured as follows.

{Measurement of Tip End Diameter of Protrusion 3}

In cases where the tip end of the protrusion 3 is not opened, the tip end portion of the protrusion 3 of the microprojection tool 1 is observed in an enlarged state under a predetermined magnification using a scanning electron microscope (SEM) or a microscope, as in the SEM image illustrated in FIG. 5(a), for example.

Next, as illustrated in FIG. 5(a), an imaginary straight line 1La is extended along the straight-line portion of one lateral side 1a of the two lateral sides 1a, 1b. Also, an imaginary straight line 1Lb is extended along the straight-line portion of the other lateral side 1b. The point where the lateral side 1a separates from the imaginary straight line 1La on the tip end side is defined as a first tip end point 1a1, and the point where the other lateral side 1b separates from the imaginary straight line 1Lb is defined as a second tip end point 1b 1. The length L of a straight line that connects the first tip end point 1a1 and the second tip end point 1b1 defined as above is measured using a scanning electron microscope (SEM) or a microscope, and the measured length of the straight line is defined as the tip end diameter of the microprojection tool 1. In cases where the tip end of the protrusion 3 is opened, as illustrated in FIG. 5(b), imaginary straight lines 1La, 1Lb are rendered assuming that the protrusion 3 has a tip end on the opening side and the intersection point of the imaginary lines is defined as the apex of the protrusion 3, and the aforementioned method illustrated in FIG. 5(a) is employed to measure the tip end diameter.

As illustrated in FIGS. 1 and 2, the nine protrusions 3 arranged on the upper surface of the sheet-like base 2 are preferably arranged such that the center-to-center distance in the second direction is uniform and the center-to-center distance in the first direction is uniform, and preferably, the center-to-center distance in the second direction is the same as the center-to-center distance in the first direction. Preferably, the center-to-center distance in the second direction between the protrusions 3 is preferably 0.01 mm or greater, more preferably 0.05 mm or greater, and preferably 10 mm or less, more preferably 5 mm or less, and more specifically, preferably from 0.01 to 10 mm, more preferably from 0.05 to 5 mm. The center-to-center distance in the first direction between the protrusions 3 is preferably 0.01 mm or greater, more preferably 0.05 mm or greater, and preferably 10 mm or less, more preferably 5 mm or less, and more specifically, preferably from 0.01 to 10 mm, more preferably from 0.05 to 5 mm.

The base 2 is formed in a sheet shape having a uniform thickness, and its thickness T2 (see FIG. 4(b)) is preferably 0.01 mm or greater, more preferably 0.02 mm or greater, and preferably 1.0 mm or less, more preferably 0.7 mm or less, and more specifically, preferably from 0.01 to 1.0 mm, more preferably from 0.02 to 0.7 mm.

As illustrated in FIG. 2, the microprojection unit 10 has, on the upper surface of the base 2, a protrusion region 3R which is a region in which the nine protrusions 3 are formed. Herein, the protrusion region 3R refers to a region surrounded by the outermost protrusions 3 in a planar direction including the first direction and the second direction in a planar view of the microprojection unit 10 as viewed from the microprojection tool 1 side. The protrusion region 3R is formed more inward than a later-described joined region 5 with the base component 4.

Figure 3:
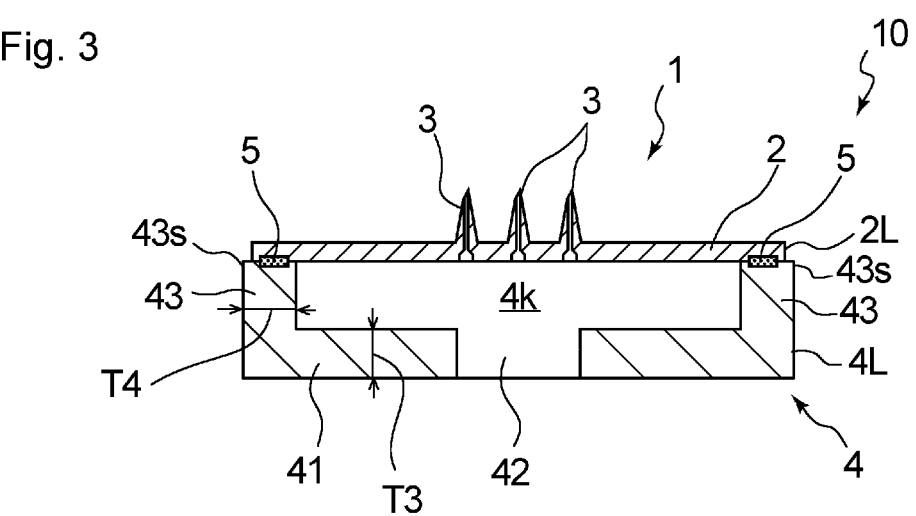
FIG. 3 is a cross-sectional view taken along line illustrated in FIG. 2.

As illustrated in FIG. 3, the base component 4 has a liquid retention space 4k that is in communication with the interior space 3k of the protrusions 3 through the base 2. The base component 4 includes: a bottom portion 41 that forms a lower surface on the opposite side from an upper surface where the joined region 5 with the microprojection tool 1 is formed; a liquid supply path 42 that penetrates the bottom portion 41 and supplies a liquid into the liquid retention space 4k; and a peripheral wall portion 43 that is arranged so as to extend over the entire outer periphery of the bottom portion 41 and is arranged in a standing condition on the upper surface (the surface on the microprojection tool 1 side) of the bottom portion 41. The space surrounded by the microprojection tool 1's base 2, the bottom portion 41, and the peripheral wall portion 43 constitutes the liquid retention space 4k. As described above, the peripheral wall portion 43 is arranged around the outer periphery of the liquid retention space 4k. The microprojection unit 10 is formed such that, for example, a syringe for supplying a liquid can be connected to a supply opening of the liquid supply path 42 of the base component 4.

In relation to the base component 4, the shape of the contour 4L of the base component 4 in a planar view of the microprojection unit 10 viewed from the microprojection tool 1 side—i.e., the outer peripheral shape of the bottom portion 41—is not particularly limited; in this microprojection unit 10, the shape is circular, as illustrated in FIG. 2. In the microprojection unit 10 illustrated in FIG. 1, the entire outer shape of the base component 4 is formed in a circular cylindrical shape, with the bottom portion 41 being circular. Note that, although the shape of the contour 4L of the base component 4 is circular in this microprojection unit 10, the shape may be, for example, elliptical, rhombic, triangular, rectangular, or pentagonal, other than circular. The entire shape of the base component 4 may be, for example, a circular-conic shape, a prism, or a pyramid, other than a circular cylinder.

From the viewpoint of easily allowing the base 2 to bend so as to project outward when a liquid is introduced into the liquid retention space 4k and inner pressure is applied, it is preferable that, in the base component 4, the thickness T3 (see FIG. 3) of the base component 4's bottom portion 41 is greater than the thickness T2 of the base 2, and is preferably 1.0 mm or greater, more preferably 1.5 mm or greater, and preferably 10 mm or less, more preferably 5 mm or less, and more specifically, preferably from 1.0 to 10 mm, more preferably from 1.5 to 5 mm.

In the base component 4, from the same viewpoint, it is preferable that the thickness T4 (see FIG. 3) of the base component 4's peripheral wall portion 43 is greater than the thickness T2 of the base 2, and is preferably 1.0 mm or greater, more preferably 1.5 mm or greater, and preferably 10 mm or less, more preferably 5 mm or less, and more specifically, preferably from 1.0 to 10 mm, more preferably from 1.5 to 5 mm.

In the microprojection unit 10, as illustrated in FIGS. 2 and 3, the contour of the microprojection tool 1—i.e., the contour 2L of the base 2 of the microprojection tool 1—is arranged at a position more inward than the contour 4L of the base component 4 in a planar view from the microprojection tool 1 side. From the viewpoint of improving appearance and the feel upon use, it is preferable that the contour 2L of the base 2 of the microprojection tool 1 is arranged on the inner side of the contour 4L of the base component 4 with a spacing W1 therebetween of preferably 0.05 mm or greater, more preferably 0.1 mm or greater, and preferably 5 mm or less, more preferably 3 mm or less, and more specifically, preferably from 0.05 to 5 mm, more preferably from 0.1 to 3 mm.

In the microprojection unit 10, as illustrated in FIG. 2, a joined region 5 where the base component 4 and the microprojection tool 1 have been joined together is provided at a position within the contour of the microprojection tool—i.e., the contour 2L of the base 2 of the microprojection tool 1—in a planar view from the microprojection tool 1 side. The joined region 5 is formed as a continuous joined region on a tip-end wall portion 43s of the peripheral wall portion 43 arranged so as to extend over the outer periphery of the liquid retention space 4k of the base component 4, and is arranged in an annular ring shape over the entire region of the outer periphery of the liquid retention space 4k. Herein, the "position within the contour 2L" either means that the contour 2L of the base 2 of the microprojection tool 1 matches the outer-side peripheral edge of the continuous joined region 5, or the outer-side peripheral edge of the continuous joined region 5 is arranged more inward than the contour 2L of the base 2 of the microprojection tool 1.

In the microprojection unit 10, as illustrated in FIG. 2, from the viewpoint of improving adhesion strength, appearance, and the feel upon use, it is preferable that the width W2 of the continuous joined region 5 in a planar view from the microprojection tool 1 side is preferably 0.5 mm or greater, more preferably 1 mm or greater, and preferably 5 mm or less, more preferably 3 mm or less, and more specifically, preferably from 0.5 to 5 mm, more preferably from 1 to 3 mm.

In the microprojection unit 10, as illustrated in FIG. 2, from the viewpoint of improving cutting stability, appearance, and the feel upon use, it is preferable that, in a planar view from the microprojection tool 1 side, the spacing W3 between the contour 2L of the base 2 and the outer-side peripheral edge of the joined region 5 is arranged at a spacing W3 of preferably 0.05 mm or greater, more preferably 0.1 mm or greater, and preferably 5 mm or less, more preferably 3 mm or less, and more specifically, preferably from 0.05 to 5 mm, more preferably from 0.1 to 3 mm.

In the microprojection unit 10, as illustrated in FIG. 2, from the viewpoint of forming the protrusion region 3R more inward than the joined region 5, it is preferable that, in a planar view from the microprojection tool 1 side, the spacing W4 between the inner-side peripheral edge of the joined region 5 and the inner wall of the tip-end wall portion 43s of the peripheral wall portion 43 is arranged at a spacing W4 of preferably 0.05 mm or greater, more preferably 0.1 mm or greater, and preferably 5 mm or less, more preferably 3 mm or less, and more specifically, preferably from 0.05 to 5 mm, more preferably from 0.1 to 3 mm.

Figure 6:
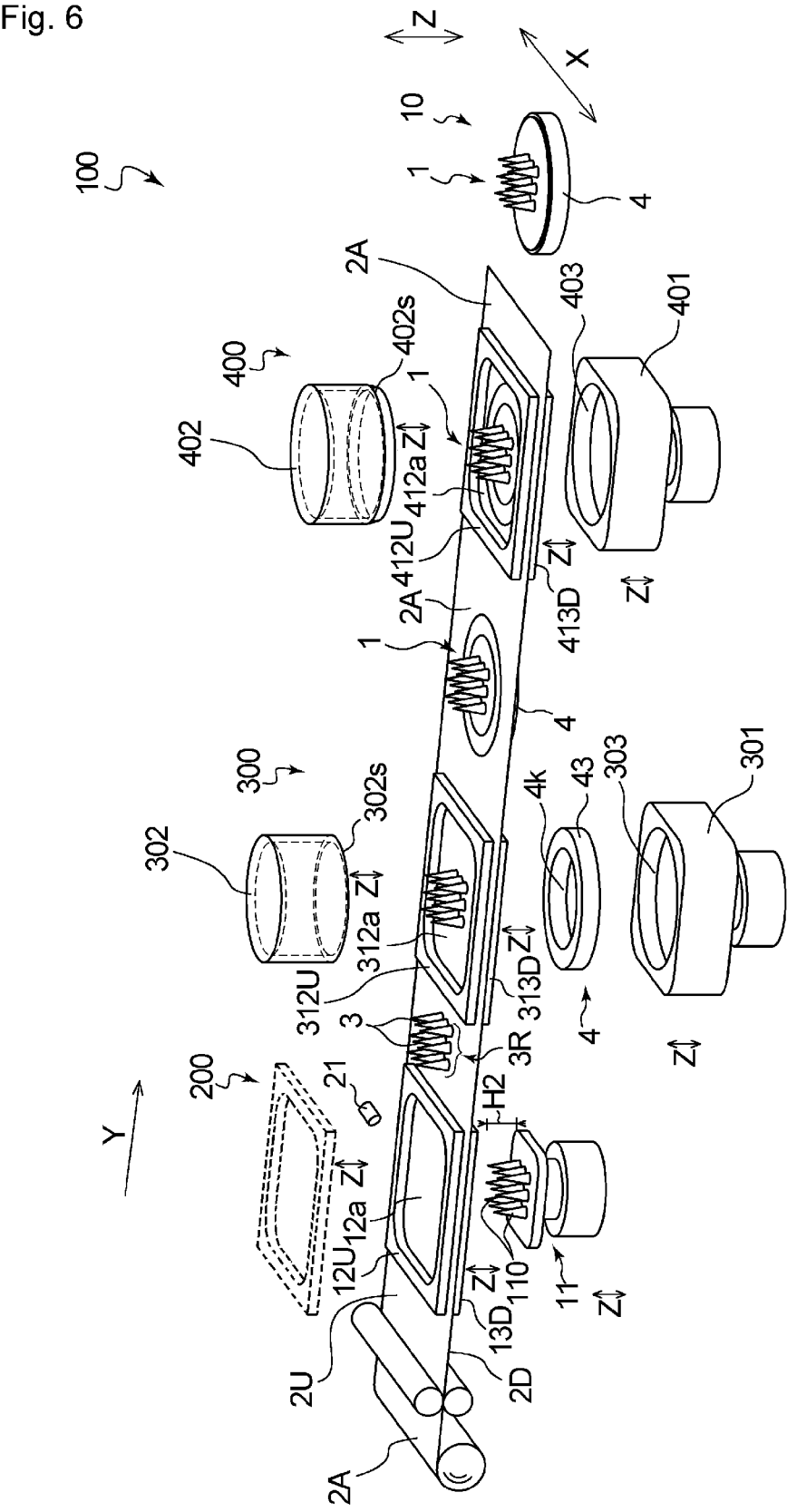
FIG. 6 is a diagram illustrating an overall configuration of a preferred manufacturing device for manufacturing the microprojection unit illustrated in FIG. 1.

Next, a method for manufacturing a microprojection unit of the invention is described with reference to FIGS. 6 to 10, taking a method for manufacturing the aforementioned microprojection unit 10 as an example. FIG. 6 illustrates an overall configuration of a manufacturing device 100 according to a preferred embodiment used for implementing the method for manufacturing the microprojection unit 10. It should be noted that, the protrusions 3 of the microprojection unit 10 are actually very small as described above, but for the sake of explanation, the protrusions 3 are illustrated very large in the figures.

In the following description, the direction in which the base sheet 2A is transported (the longitudinal direction of the base sheet 2A) is referred to as the Y direction, the direction orthogonal to the transporting direction, which is the width direction of the base sheet 2A being transported, is referred to as the X direction, and the thickness direction of the base sheet 2A being transported is referred to as the Z direction.

The method for manufacturing a microprojection unit 10 involves: a microprojection tool forming step of forming a microprojection tool 1 by bringing a projecting mold part 11 into contact from one surface 2D side of a base sheet 2A including a thermoplastic resin, and thus forming protrusions 3 that protrude from another surface 2U side of the base sheet 2A, and withdrawing the projecting mold part 11 from the interior of the protrusions 3; a joining step of joining the one surface 2D side of the base sheet 2A, in which the microprojection tool 1 has been formed, and a tip end of a base component 4; and a cutting step of cutting the base sheet 2A, to which the base component 4 has been joined, at a position more inward than the base component 4's contour 4L in a planar view of the base sheet 2A as viewed from the microprojection tool 1 side, to manufacture a microprojection unit 10.

As illustrated in FIG. 6, the manufacturing device 100 includes, from the upstream side toward the downstream side in the transporting direction (corresponding to the Y direction): a microprojection tool forming section 200 that forms a microprojection tool 1; a member joining section 300 that joins a base component 4 and a base sheet 2A in which the microprojection tool 1 has been formed; and a member cutting section 400 that cuts the base sheet 2A to thereby manufacture a microprojection unit 10. In the manufacturing device 100, the microprojection tool forming section 200 includes, as illustrated in FIG. 7: a protrusion forming section 210 for forming protrusions 3 in the base sheet 2A; a cooling section 220; and a release section 230 where the projecting mold part 11 is withdrawn.

In the present Specification, the projecting mold part 11 is a member including projecting molds 110 which are sections inserted into the base sheet 2A, and in the present embodiment, the projecting mold part 11 is structured so as to be arranged on a disk-shaped foundation. The projecting mold part's structure, however, is not limited thereto, and the projecting mold part may consist only of the projecting mold 110, or the projecting mold part 11 may include a plurality of projecting molds 110 arranged on a platform-like support.

Figure 7:
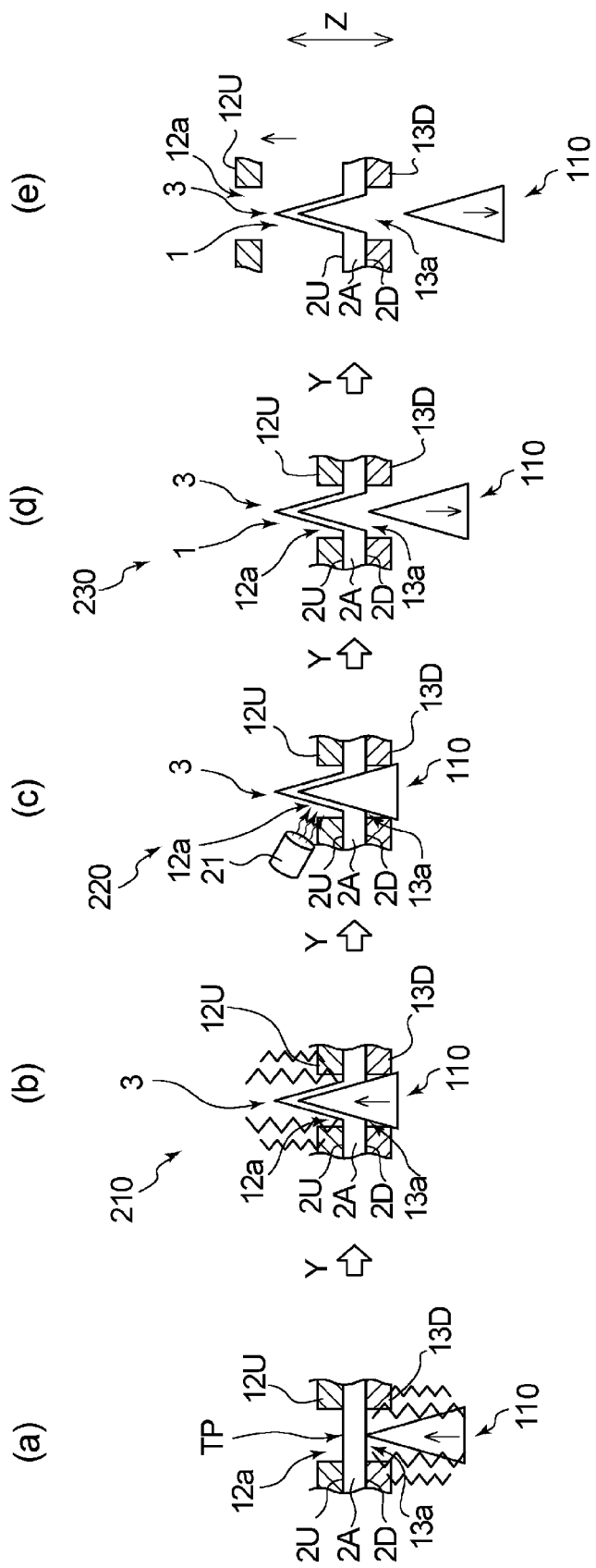
FIGS. 7(*a*) to 7(*e*) are diagrams illustrating steps for manufacturing a microprojection tool by employing the manufacturing device illustrated in FIG. 6.

The protrusion forming section 210 is described using FIGS. 6 and 7. As illustrated in FIG. 6, the protrusion forming section 210 includes a projecting mold part 11 including a heating means (not illustrated). In the manufacturing device 100, a heating means may be provided to the projecting mold part 11. Further, in the manufacturing device 100, there may be no other heating means except for the heating means of the projecting mold part 11. It should be noted that, in this Specification, "there is no other heating means except for the heating means of the projecting mold part 11" not only refers to cases where other heating means are completely eliminated, but also refers to cases where a means for heating to a temperature below the softening temperature of the base sheet 2A, or to a temperature below the glass transition temperature, is provided. Note, however, that it is preferable to completely eliminate all other heating means. In the manufacturing device 100, the heating means of the projecting mold part 11 is an ultrasonic vibration device.

In the method for manufacturing the microprojection unit 10 by using the manufacturing device 100, first, as illustrated in FIG. 6, a continuous base sheet 2A is paid out from a material roll of the base sheet 2A formed including a thermoplastic resin, and is transported in the transporting direction. Then, when the base sheet 2A has been fed to a predetermined position, the transportation of the base sheet 2A is stopped. In this way, in the method for manufacturing the microprojection unit 10, the continuous base sheet 2A is transported intermittently.

The base sheet 2A is a sheet that constitutes the base 2 of the microprojection tool 1 being manufactured, and is formed by including a thermoplastic resin. Examples of the thermoplastic resin include poly-fatty acid esters, polycarbonate, polypropylene, polyethylene, polyester, polyamide, polyamide imide, polyether ether ketone, polyetherimide, polystyrene, polyethylene terephthalate, polyvinyl chloride, nylon resin, acrylic resin, and combinations thereof. From the viewpoint of biodegradability, poly-fatty acid esters are preferably used. Concrete examples of poly-fatty acid esters include polylactic acid, polyglycolic acid, and combinations thereof. Note that the base sheet 2A may be formed of a mixture including, for example, hyaluronic acid, collagen, starch, cellulose, etc., in addition to thermoplastic resin. The thickness of the base sheet 2A is substantially the same as the thickness T2 of the base 2 of the microprojection tool 1 being manufactured.

Next, in the microprojection tool forming step of the method for manufacturing the microprojection unit 10, as illustrated in FIGS. 7(*a*) and 7(*b*), the projecting mold part 11 is brought into contact from the one surface 2D side of the continuous base sheet 2A being transported in the transporting direction, and, while softening, with heat, a contact section TP in the base sheet 2A where the projecting mold part contacts the base sheet, the projecting mold part 11 is inserted into the base sheet 2A, to form protrusions 3 that protrude from the other surface 2U side of the base sheet 2A (protrusion forming step). In the protrusion forming section 210, an opening plate 12U, as a warp-suppressing means, is arranged on the other surface 2U side (upper surface side) of the base sheet 2A, and a second opening plate 13D, as a warp-suppressing means, is arranged on the one surface 2D side (lower surface side) of the base sheet 2A.

The projecting mold part 11 is shaped so as to have a circular-conic section with a sharp tip end, to correspond to the outer shape of the circular-conic protrusion 3 of the microprojection tool 1 being manufactured. More specifically, in the manufacturing device 100, as illustrated in FIG. 6, the projecting mold part 11 includes projecting molds 110 corresponding to the number and arrangement of the protrusions 3 on the microprojection tool 1 to be manufactured and corresponding substantially to the outer shape of each protrusion 3; and nine circular-conic projecting molds 110 are provided corresponding to the nine truncated circular-conic protrusions 3. In this way, by using the projecting mold part 11 having a plurality of projecting molds 110, a plurality of protrusions 3 arranged on the upper surface of the sheet-like base 2 are formed. In the manufacturing device 100, the projecting mold part 11 is arranged such that the respective tip ends of the projecting molds 110 face upward, and is movable at least vertically in the thickness direction. Preferably, in the manufacturing device 100, the projecting mold part 11 can be moved vertically in the thickness direction by an electric actuator (not illustrated). Note that it is preferable that the heating means of the projecting mold part 11 is operated from immediately before the projecting mold part 11 comes into contact with the base sheet 2A to immediately before the base sheet reaches the following cooling step.

The operation of the projecting mold part 11 and heating conditions of the heating means of the projecting mold part 11, such as the activation etc. of the heating means of the projecting mold part 11, are controlled by a control means (not illustrated) provided to the manufacturing device 100.

As described above, in the manufacturing device 100, the heating means of the projecting mold part 11 is an ultrasonic vibration device. As regards the ultrasonic vibration of the projecting mold part 11 by the ultrasonic vibration device, from the viewpoint of forming the protrusions 3, the frequency thereof is preferably 10 kHz or greater, more preferably 15 kHz or greater, and preferably 50 kHz or less, more preferably 40 kHz or less, and more specifically, preferably from 10 to 50 kHz, more preferably from 15 to 40 kHz. Further, from the viewpoint of forming the protrusions 3, the amplitude of the ultrasonic vibration of the projecting mold part 11 by the ultrasonic vibration device is preferably 1 μm or greater, more preferably 5 μm or greater, and preferably 60 μm or less, more preferably 50 μm or less, and more specifically, preferably from 1 to 60 μm, more preferably from 5 to 50 μm.

The shape of the projecting mold part 11 on the tip-end side only needs to be shaped so as to correspond to the outer shape of the protrusion 3 of the microprojection tool 1 being manufactured. The height H2 (cf. FIG. 6) of the projecting mold 110 of the projecting mold part 11 is formed equal to or slightly higher than the protrusion height H1 (cf. FIG. 4(*b*)) of the protrusion 3 of the microprojection tool 1 being manufactured, and is preferably 0.01 mm or greater, more preferably 0.02 mm or greater, and preferably 30 mm or less, more preferably 20 mm or less, and more specifically, preferably from 0.01 to 30 mm, more preferably from 0.02 to 20 mm. The tip end diameter D1 (cf. FIG. 8) of the projecting mold 110 of the projecting mold part 11 is preferably 0.001 mm or greater, more preferably 0.005 mm or greater, and preferably 1 mm or less, more preferably 0.5 mm or less, and more specifically, preferably from 0.001 to 1 mm, more preferably from 0.005 to 0.5 mm. The tip end diameter D1 of the projecting mold 110 of the projecting mold part 11 is measured as described below.

The base diameter D2 of the projecting mold 110 of the projecting mold part 11 is preferably 0.1 mm or greater, more preferably 0.2 mm or greater, and preferably 5 mm or less, more preferably 3 mm or less, and more specifically, preferably from 0.1 to 5 mm, more preferably from 0.2 to 3 mm. From the viewpoint of easily achieving sufficient strength, the tip end angle α of the projecting mold 110 of the projecting mold part 11 is preferably 1 degree or greater, more preferably 5 degrees or greater. From the viewpoint of obtaining a protrusion 3 having an appropriate angle, the tip end angle α is preferably 60 degrees or less, more preferably 45 degrees or less, and more specifically, preferably from 1 to 60 degrees, more preferably from 5 to 45 degrees. The tip end angle α of the projecting mold part 11 is measured as follows.

{Measurement of Tip End Diameter of Projecting Mold 110 of Projecting Mold Part 11}

Figure 8:
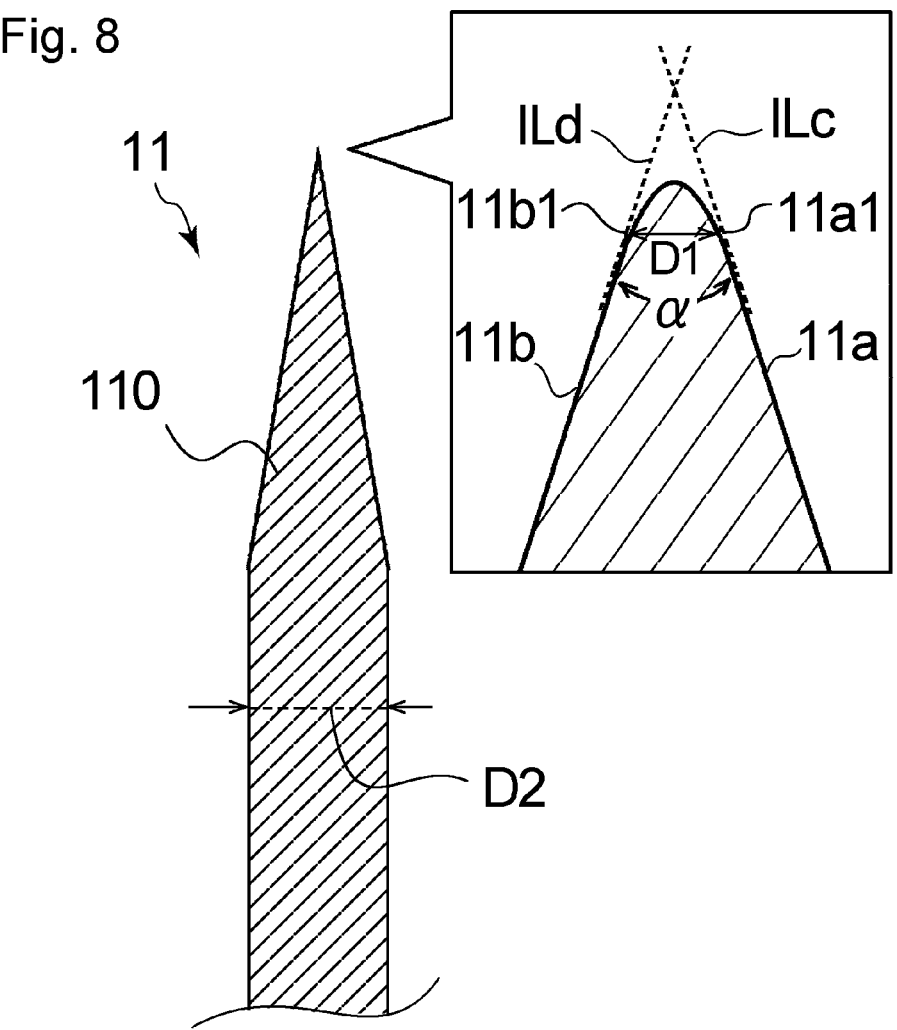
FIG. 8 is an explanatory diagram illustrating a method for measuring the tip end angle of a projecting mold part.

The tip end portion of the projecting mold 110 of the projecting mold part 11 is observed in an enlarged state under a predetermined magnification using a scanning electron microscope (SEM) or a microscope. Next, as illustrated in FIG. 8, an imaginary straight line 1Lc is extended along the straight-line portion of one lateral side 11a of the two lateral sides 11a, 11b. Also, an imaginary straight line 1Ld is extended along the straight-line portion of the other lateral side 11b. The point where the lateral side 11a separates from the imaginary straight line 1Lc on the tip end side is defined as a first tip end point 11a1, and the point where the other lateral side 11b separates from the imaginary straight line 1Ld is defined as a second tip end point 11b1. The length D1 of a straight line that connects the first tip end point 11a1 and the second tip end point 11b1 defined as above is measured using a scanning electron microscope or a microscope, and the measured length of the straight line is defined as the tip end diameter of the projecting mold 110.

{Measurement of Tip End Angle α of Projecting Mold 110 of Projecting Mold Part 11}

The tip end portion of the projecting mold 110 of the projecting mold part 11 is observed in an enlarged state under a predetermined magnification using a scanning electron microscope or a microscope, as in the SEM image illustrated in FIG. 8, for example. Next, as illustrated in FIG. 8, an imaginary straight line 1Lc is extended along the straight-line portion of one lateral side 11a of the two lateral sides 11a, 11b. Also, an imaginary straight line 1Ld is extended along the straight-line portion of the other lateral side 11b. The angle formed between the imaginary straight line 1Lc and the imaginary straight line 1Ld is measured using a scanning electron microscope or a microscope, and the measured angle is defined as the tip end angle α of the projecting mold 110 of the projecting mold part 11.

The projecting mold part 11 is formed of a high-strength material that is hard to bend/break. Examples of materials for the projecting mold part 11 include metals, such as steel, stainless steel, aluminum, aluminum alloy, nickel, nickel alloy, cobalt, cobalt alloy, copper, copper alloy, beryllium copper, and beryllium copper alloy, and ceramics.

As described above, the opening plate 12U used in the protrusion forming step is arranged on the other surface 2U side of the base sheet 2A as illustrated in FIGS. 6 and 7, and serves to make the base sheet 2A less likely to warp/bend when the projecting mold part 11 is inserted from the one surface 2D side. Thus, the opening plate 12U is arranged so as to support a region other than a region, in the base sheet 2A, into which the projecting mold part 11 is inserted—i.e., a region other than the protrusion region 3R, which is a region, in the base sheet 2A, where the protrusions 3 are formed. In the manufacturing device 100, the opening plate 12U arranged as described above is a board-like opening plate having an opening 12a opened so as to surround the protrusion region 3R. The opening plate 12U supports the base sheet 2A in regions other than the opening 12a.

In the manufacturing device 100, as illustrated in FIG. 6, a single opening 12a is formed in the opening plate 12U, and the opening area of the single opening 12a is formed so as to be greater than the total cross-sectional area of the projecting molds 110 so that a plurality of projecting molds 110 of the projecting mold part 11 can be passed through the single opening. Note that a plurality of openings 12a may be formed in the opening plate 12U so as to correspond to the respective projecting molds 110 such that the plurality of projecting molds 110 are passed therethrough respectively.

The opening plate 12U is movable in a direction separating from the direction contacting the base sheet 2A. In the manufacturing device 100, the opening plate 12U can move vertically in the thickness direction by an electric actuator. The operation of the opening plate 12U is controlled by a control means provided to the manufacturing device 100.

The material constituting the opening plate 12U may be the same as the material of the projecting mold part 11, and may be formed of a synthetic resin, for example.

The manufacturing device 100 includes an ultrasonic vibration device as a heating means of the projecting mold part 11. In the method for manufacturing the microprojection unit 10, the protrusion forming step is performed in a state where the base sheet 2A is sandwiched between the opening plate 12U and the second opening plate 13D. In the protrusion forming step using the manufacturing device 100, the projecting mold part 11 is passed through an opening 13a in the later-described second opening plate 13D from the one surface 2D side (lower surface side) of the base sheet 2A, and, while causing ultrasonic vibration in the projecting mold part 11 in advance by the ultrasonic vibration device, the projecting mold part 11 is made to contact the one surface 2D of the base sheet 2A, as illustrated in FIG. 7(a). Thus, the contact sections TP are softened. Then, as illustrated in FIG. 7(b), while softening the contact sections TP, the projecting mold part 11 is raised from the one surface 2D side (lower surface side) of the base sheet 2A toward the other surface 2U side (upper surface side), and the projecting mold part 11 is inserted into the base sheet 2A, while suppressing warping of the base sheet 2A with the opening plate 12U arranged on the other surface 2U side (upper surface side) of the base sheet 2A, thereby forming protrusions 3 that protrude from the other surface 2U side (upper surface side) of the base sheet 2A.

From the viewpoint of forming the protrusions 3, the heating temperature of the base sheet 2A by heating the projecting mold part 11 is preferably equal to or higher than the glass transition temperature of the base sheet 2A being used to below the melting temperature thereof, and more preferably, equal to or higher than the softening temperature of the base sheet 2A to below the melting temperature thereof. More specifically, the heating temperature is preferably 30° C. or higher, more preferably 40° C. or higher, and preferably 300° C. or lower, more preferably 250° C. or lower, and more specifically, preferably from 30° C. to 300° C., more preferably from 40° C. to 250° C. In cases where the base sheet 2A is heated by using an ultrasonic vibration device, the aforementioned heating temperature range is employed as the temperature range of a section of the base sheet 2A that comes into contact with the projecting mold 110. On the other hand, in cases where the base sheet 2A is heated by using a heating heater device instead of the ultrasonic vibration device, the heating temperature of the projecting mold part 11 simply needs to be adjusted within the aforementioned range. It should be noted that the glass transition temperature (Tg) is measured according to the following measurement method, and the softening temperature is measured according to JIS K-7196 "Testing method for softening temperature of thermoplastic film and sheeting by thermomechanical analysis".

{Method for Measuring Glass Transition Temperature (Tg)}

The glass transition temperature is determined by measuring the heat quantity by using a DSC measurement device. More specifically, the measurement device used is a differential scanning calorimeter (Diamond DSC) from Perkin Elmer. A 10-mg test piece is sampled from the base sheet. As for the measurement conditions, the temperature is maintained at 20° C. for 5 minutes, and then the temperature is raised from 20° C. to 320° C. at a rate of 5° C./minute, to obtain a DSC curve wherein the horizontal axis indicates temperature and the vertical axis indicates heat quantity. The glass transition temperature Tg is determined from the DSC curve.

Note that the "glass transition temperature (Tg) of the base sheet" refers to the glass transition temperature (Tg) of the resin constituting the base sheet. In cases where there are a plurality of types of constituent resins and the plurality of glass transition temperatures (Tg) are different from each other, the heating temperature of the base sheet by the heating means is preferably at least equal to or higher than the lowest glass transition temperature (Tg) among the plurality of glass transition temperatures (Tg), and more preferably equal to or higher than the highest glass transition temperature (Tg) among the plurality of glass transition temperatures (Tg).

The same applies to the "softening temperature of the base sheet", as with the glass transition temperature (Tg). In cases where there are a plurality of types of constituent resins in the base sheet and the plurality of softening temperatures are different from each other, the heating temperature of the base sheet by the heating means is preferably at least equal to or higher than the lowest softening temperature among the plurality of softening temperatures, and more preferably equal to or higher than the highest softening temperature among the plurality of softening temperatures.

In cases where the base sheet includes two or more types of resins having different melting points, the heating temperature of the base sheet by the heating means is preferably below the lowest melting point among the plurality of melting points.

If the insertion speed for inserting the projecting mold part 11 into the base sheet 2A is too slow, the resin will get heated and softened excessively, whereas if the insertion speed is too fast, heating and softening will be insufficient. Thus, from the viewpoint of forming the protrusions 3 efficiently, the insertion speed is preferably 0.1 mm/second or greater, more preferably 1 mm/second or greater, and preferably 1000 mm/second or less, more preferably 800 mm/second or less, and more specifically, preferably from 0.1 to 1000 mm/second, more preferably from 1 to 800 mm/second. The softening time is the time from when the elevation of the heated-state projecting mold part 11 is stopped until the following cooling step is performed while keeping the projecting mold part 11 inserted in the interior of the protrusion 3. Although a too-long softening time will result in excessive heating, from the viewpoint of supplementing insufficient heating, the softening time is preferably 0 seconds or longer, more preferably 0.1 seconds or longer, and preferably 10 seconds or less, more preferably 5 seconds or less, and more specifically, preferably from 0 to 10 seconds, more preferably from 0.1 to 5 seconds.

From the viewpoint of forming the protrusions 3 efficiently, the insertion height of the projecting mold part 11 inserted into the base sheet 2A is preferably 0.01 mm or greater, more preferably 0.02 mm or greater, and preferably 10 mm or less, more preferably 5 mm or less, and more specifically, preferably from 0.01 to 10 mm, more preferably from 0.02 to 5 mm. Herein, "insertion height" refers to the distance between the apex of the projecting mold part 11 and the other surface 2U (upper surface) of the base sheet 2A in a state where the projecting mold part 11 is inserted furthest in the base sheet 2A. So, the insertion height in the protrusion forming step refers to the distance measured in the perpendicular direction from the other surface 2U to the apex of the projecting mold part 11 in a state where the projecting mold part 11 has been inserted furthest in the protrusion forming step and the projecting mold part 11 has emerged from the other surface 2U of the base sheet 2A.

In cases of manufacturing a microprojection tool 1 that has an opening in the vicinity of the tip end of each protrusion 3 and the interior space 3k of each protrusion 3 is formed from the base 2 up to the opening, the opening can be formed by inserting the projecting mold part 11 into the base sheet 2A until it penetrates the base sheet by controlling the operations of the projecting mold part 11 and/or the heating conditions etc. of the heating means of the projecting mold part 11 in the protrusion forming step.

In cases of manufacturing a microprojection tool 1 that has an opening in a position deviating from the center of the tip end of the protrusion 3, first, a non-penetrating protrusion 3 that protrudes from the other surface 2U side of the base sheet 2A is formed by: bringing the projecting mold part 11 into contact from the one surface 2D side of the base sheet 2A including a thermoplastic resin; and while softening, with heat, a contact section in the base sheet 2A where the projecting mold part 11 contacts the base sheet 2A, inserting the projecting mold part 11 into the base sheet 2A toward the other surface 2U side of the base sheet 2A. Then, the protrusion 3 is cooled in a state where the projecting mold part 11 is inserted in the interior of the protrusion 3. Then, the projecting mold part 11 is removed from the interior of the protrusion 3, to form a hollow-interior protrusion 3. Thereafter, an opening penetrating the interior of the protrusion 3 may be formed in a position deviating from the center of the tip end of the protrusion 3 that has been formed.

Next, in the manufacturing device 100, as illustrated in FIG. 7(c), a cooling section 220 is provided subsequent to the protrusion forming section 210. The cooling section 220 includes, for example, a cold air blowing device (not illustrated). In the microprojection tool forming step of the method for manufacturing the microprojection unit 10, after the protrusion forming step using the manufacturing device 100, the protrusions 3 are cooled by using this cold air blowing device in a state where the projecting mold part 11 is inserted in the interior of the protrusions 3 (cooling step). More specifically, in the manufacturing device 100, the opening plate 12U is arranged on the other surface 2U side (upper surface side) of the base sheet 2A and the later-described second opening plate 13D is arranged on the one surface 2D side (lower surface side) of the base sheet 2A. Thus, in the method for manufacturing the microprojection unit 10, the cooling step is performed in a state where the base sheet 2A is sandwiched between the opening plate 12U and the second opening plate 13D. In the cold air blowing device of the manufacturing device 100, as illustrated in FIG. 4, an air vent 21 for blowing cold air is provided on the other surface 2U side (upper surface side) of the base sheet 2A, and cooling is performed by blowing cold air from the air vent 21 in a state where the projecting mold part 11 is kept inserted in the interior of the protrusions 3. Note that, during cooling, heating of the projecting mold part 11 with the heating device may be continued or stopped, but it is preferable that heating is stopped.

From the viewpoint of forming the protrusions 3, the temperature of the cold air to be blown is preferably −50° C. or higher, more preferably −40° C. or higher, and preferably 26° C. or lower, more preferably 10° C. or lower, and more specifically, preferably from −50° C. to 26° C., more preferably from −40° C. to 10° C. From the viewpoint of balancing moldability and processing time, the cooling time for cooling by blowing cold air is preferably 0.01 seconds or longer, more preferably 0.5 seconds or longer, and preferably 60 seconds or less, more preferably 30 seconds or less, and more specifically, preferably from 0.01 to 60 seconds, more preferably from 0.5 to 30 seconds.

In cases where the heating means of the projecting mold part 11 is ultrasonic vibration as in the manufacturing device 100, the cold air blowing device does not necessarily have to be provided, and cooling can be achieved by simply turning off the vibration of the ultrasonic vibration device. From this viewpoint, using ultrasonic vibration as the heating means is preferable in terms that the device can be simplified and microprojection tools 1 can be manufactured easily at high speed. Further, heat is less likely to be transmitted to sections of the base sheet 2A that are not in contact with the projecting mold part 11 and cooling is performed efficiently by stopping the application of ultrasonic vibration; this is advantageous in that deformation is less likely to occur in sections other than the section being molded.

Next, in the manufacturing device 100, as illustrated in FIG. 7(*d*), a release section 230 is provided subsequent to the cooling section 220. In the microprojection tool forming step of the method for manufacturing the microprojection unit 10, the projecting mold part 11 is withdrawn from the interior of the protrusions 3 after the cooling step, to form a microprojection tool 1 (release step). In the release step, the second opening plate 13D, which serves as a warp-suppressing means that suppresses warping of the base sheet 2A, is used when the projecting mold part 11 is withdrawn from the interior of the protrusions 3, to thereby form the microprojection tool 1. In the manufacturing device 100, the second opening plate 13D used in the release step is arranged on the one surface 2D side of the base sheet 2A, and is arranged at a position corresponding to the predetermined position to which the base sheet 2A is fed.

The second opening plate 13D used in the release step is arranged on the one surface 2D side of the base sheet 2A as illustrated in FIGS. 6 and 7, and serves to make the base sheet 2A less likely to warp/bend when the projecting mold part 11 is withdrawn from the one surface 2D side. Thus, the second opening plate 13D is arranged so as to support a region other than a region, in the base sheet 2A, from which the projecting mold part 11 is withdrawn—i.e., a region other than the protrusion region 3R, which is a region, in the base sheet 2A, where the protrusions 3 are formed. In the manufacturing device 100, the second opening plate 13D arranged as described above is a board-like second opening plate having an opening 13a opened so as to surround the protrusion region 3R. The second opening plate 13D supports the base sheet 2A in regions other than the opening 13a.

In the manufacturing device 100, as illustrated in FIG. 7, a single opening 13a is formed in the second opening plate 13D, and the opening area of the single opening 13a is formed so as to be greater than the total cross-sectional area of the projecting molds 110 so that a plurality of projecting molds 110 of the projecting mold part 11 can be passed through the single opening. Note that a plurality of openings 13a may be formed in the second opening plate 13D so as to correspond to the respective projecting molds 110 such that the plurality of projecting molds 110 are passed therethrough respectively. In the manufacturing device 100, the opening 13a of the second opening plate 13D is arranged concentrically with the opening 12a of the opening plate 12U. Thus, the openings 12a, 13a of the pair of the opening plate 12U and the second opening plate 13D sandwiching the base sheet 2A overlap one another in the thickness direction.

In the manufacturing device 100, the opening 12a of the opening plate 12U and the opening 13a of the second opening plate 13D have the same opening shape. Note that the shape of the openings 12a, 13a as viewed from the upper surface side of the opening plates 12U, 13D is not particularly limited; in the manufacturing device 100, the openings are both circular, and the opening diameter of the openings 12a, 13a is the same.

The second opening plate 13D may be fixed, but in the manufacturing device 100, the second opening plate is movable in a direction separating from the direction contacting the base sheet 2A. The second opening plate 13D is made movable vertically in the thickness direction by an electric actuator (not illustrated).

The operation of the second opening plate 13D is controlled by a control means (not illustrated) provided to the manufacturing device 100.

The material constituting the second opening plate 13D may be the same as the material constituting the opening plate 12U or the material of the projecting mold part 11, and may be formed of a synthetic resin, for example.

In the manufacturing device 100, the opening plate 12U is arranged on the other surface 2U side (upper surface side) of the base sheet 2A, and the second opening plate 13D is arranged on the one surface 2D side (lower surface side) of the base sheet 2A. Thus, the release step is performed in a state where the base sheet 2A is sandwiched between the opening plate 12U and the second opening plate 13D. In the method for manufacturing the microprojection unit 10, as illustrated in FIG. 7(*e*), after performing the release step in a state where the base sheet 2A is sandwiched between the opening plate 12U and the second opening plate 13D, the second opening plate 13D is moved downward and the opening plate 12U is moved upward, and thereby, a microprojection tool 1 having protrusions 3 with a hollow interior is formed in the base sheet 2A (microprojection tool forming step).

Figure 9:
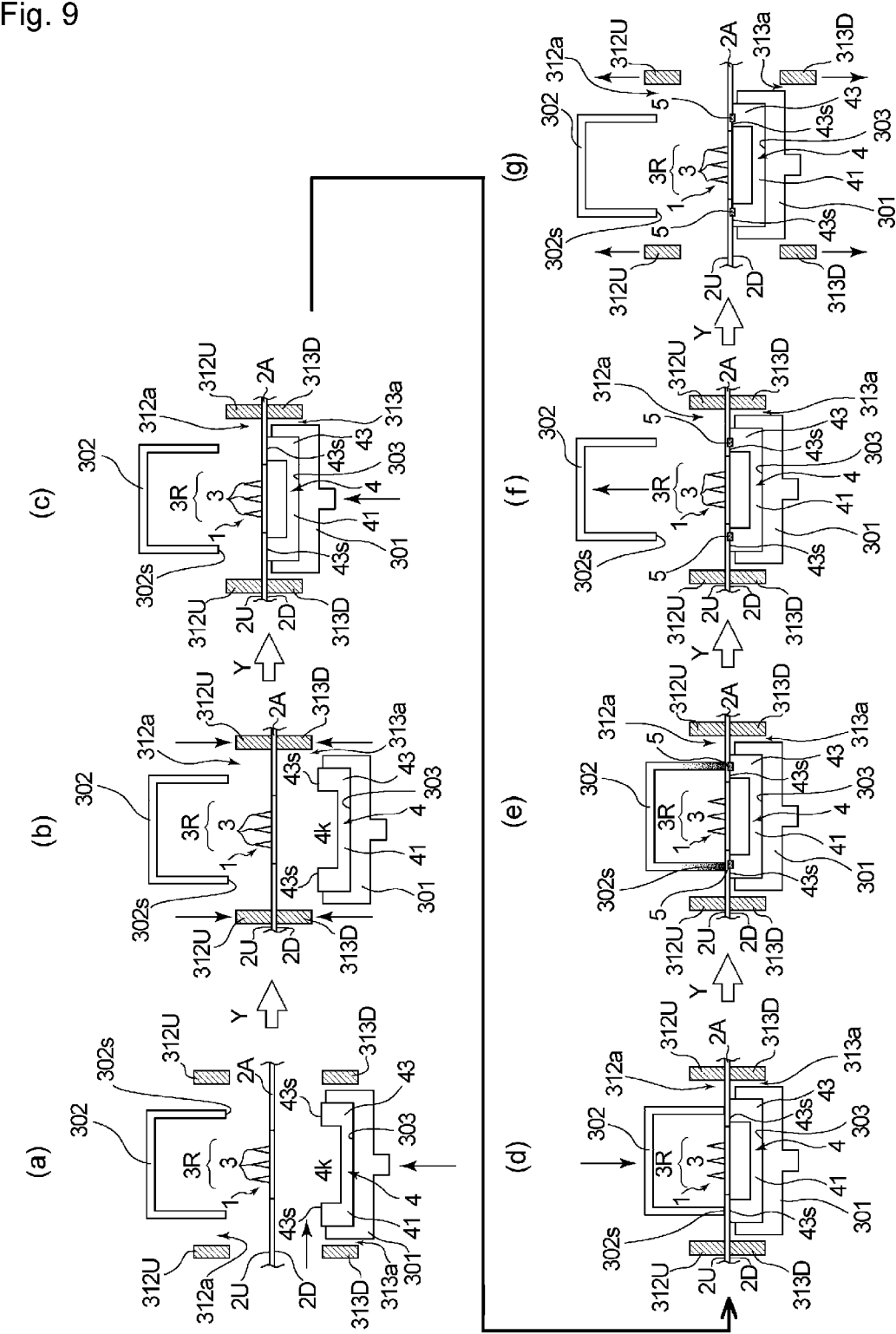
FIGS. 9(*a*) to 9(*g*) are diagrams illustrating a joining step for forming a joined region by employing the manufacturing device illustrated in FIG. 6.

Next, as illustrated in FIG. 6, the base sheet 2A, in which the microprojection tool 1 having the protrusions 3 has been formed, is moved in the transporting direction. In the step following the microprojection tool forming step, as illustrated in FIGS. 6 and 9, the one surface 2D side (lower surface side) of the base sheet 2A—in which the microprojection tool 1, manufactured in the microprojection tool forming step, has been formed—and the tip end of the base component 4 are joined together (joining step). Herein, the "tip end of the base component 4" refers to a section of the base component 4 located closest to the one surface 2D side (lower surface side) of the base sheet 2A; in the microprojection unit 10, it refers to the tip-end wall portion 43s which is the tip end of the peripheral wall portion 43 arranged so as to extend over the outer periphery of the liquid retention space 4k of the base component 4. The joining step is performed by using the manufacturing device 100's member joining section 300 for joining the base sheet 2A, in which the microprojection tool 1 has been formed, and the base component 4.

In cases of forming the joined region 5 by fusion-bonding, it is preferable that the base component 4 is formed including the same type of thermoplastic resin as the base sheet 2A, from the viewpoint of facilitating formation of the joined region 5. Examples of the thermoplastic resin include poly-fatty acid esters, polycarbonate, polypropylene, polyethylene, polyester, polyamide, polyamide imide, polyether ether ketone, polyetherimide, polystyrene, polyethylene terephthalate, polyvinyl chloride, nylon resin, acrylic resin, and combinations thereof. From the viewpoint of biodegradability, poly-fatty acid esters are preferably used. Concrete examples of poly-fatty acid esters include polylactic acid, polyglycolic acid, and combinations thereof. Note that, in cases where the joined region 5 is to be formed by using an adhesive, the base component 4 may be made of a material different from the base sheet 2A, and may be made of metal, for example.

In the manufacturing device 100, as illustrated in FIGS. 6 and 9, the member joining section 300 includes: a base component fixing part 301 that fixes the base component 4; a joining section 302 that joins the base sheet 2A, in which the microprojection tool 1 has been formed, and the base component 4; and a first upper opening plate 312U and a first lower opening plate 313D that sandwich the base sheet 2A, in which the microprojection tool 1 having the protrusions 3 has been formed. The base component fixing part 301 has a depression 303 having a shape corresponding to the outer shape of the entire base component 4. In the manufacturing device 100, the depression 303 is formed in a shape that fits with a cylindrical shape having a circular bottom portion 41.

As illustrated in FIG. 6, the base component fixing part 301, having the depression 303, is arranged on the one surface 2D (lower surface) side of the base sheet 2A, and holds the base component 4's bottom portion 41 side in a manner that the outer shape of the base component 4's bottom portion 41 side is fitted in the depression 303 and the tip-end wall portion 43s of the base component 4's peripheral wall portion 43 is exposed. The base component fixing part 301 may be fixed, but in this manufacturing device 100, the base component fixing part is movable in a direction separating from the direction contacting the base sheet 2A. More specifically, the base component fixing part 301 is made movable vertically in the thickness direction by an electric actuator (not illustrated).

The operation of the base component fixing part 301 is controlled by a control means (not illustrated) provided to the manufacturing device 100.

The base component fixing part 301 may be made of the same material as that of the projecting mold part 11, and may be made, for example, of a synthetic resin.

The joining section 302 is a section that joins the base sheet 2A, in which the microprojection tool 1 has been formed, and the base component 4. As illustrated in FIGS. 6 and 9, the joining section 302 annularly surrounds the protrusion region 3R, which is a region, in the base sheet 2A, where the protrusions 3 are formed, and has an annular ring-shaped tip-end portion 302s corresponding to the peripheral wall portion 43 of the base component 4. The joining section 302 having the tip-end portion 302s is formed in a tubular shape with the tip-end portion 302s side opened. Preferably, the width of the tip-end portion 302s of the joining section 302 is narrower than the width of the tip-end wall portion 43s of the peripheral wall portion 43 of the base component 4, and substantially matches the width W2 of the continuous joined region 5.

As illustrated in FIGS. 6 and 9, the joining section 302 is arranged on the other surface 2U (upper surface) side of the base sheet 2A. In the manufacturing device 100, the joining section 302 is movable in a direction separating from the direction contacting the base sheet 2A. More specifically, the joining section 302 is made movable vertically in the thickness direction by an electric actuator (not illustrated).

The operation of the joining section 302 is controlled by a control means (not illustrated) provided to the manufacturing device 100.

Examples of means for performing joining in the joining step include heat sealing, ultrasound, a laser, an adhesive, or the like. In the manufacturing device 100, the joining means in the joining section 302 is a joining means by heat sealing. Note that heat sealing, ultrasound, and laser are joining means that perform joining by employing fusion-bonding, i.e., a phenomenon in which the materials of the base sheet 2A and the base component 4 are molten and bonded by heat. For the adhesive, it is possible to use, for example, a hot-melt adhesive, which is conventionally used in this type of product.

As illustrated in FIG. 9, the first lower opening plate 313D is arranged on the one surface 2D (lower surface) side of the base sheet 2A, and is formed of a board-like plate having a single opening 313a. The opening area of the opening 313a is formed greater than the planar area of the base component fixing part 301 so that the base component fixing part 301 can be passed therethrough when the base component fixing part 301 is moved upward in the thickness direction from the one surface 2D side.

As illustrated in FIG. 9, the first upper opening plate 312U is arranged on the other surface 2U (upper surface) side of the base sheet 2A, and is formed of a board-like plate having a single opening 312a. The opening area of the opening 312a is formed greater than the planar area of the joining section 302 so that the joining section 302 can be passed therethrough when the joining section 302 is moved downward in the thickness direction from the other surface 2U side.

The first lower opening plate 313D and the first upper opening plate 312U are movable in a direction separating from the direction contacting the base sheet 2A. In the manufacturing device 100, the first lower opening plate 313D and the first upper opening plate 312U are made movable vertically in the thickness direction by an electric actuator (not illustrated).

The operation of the first lower opening plate 313D and the first upper opening plate 312U is controlled by a control means (not illustrated) provided to the manufacturing device 100.

In the method for manufacturing the microprojection unit 10, the base component 4 is held in a manner that the outer shape of the base component 4's bottom portion 41 side is fitted in the depression 303 of the base component fixing part 301 and the tip-end wall portion 43s of the base component 4's peripheral wall portion 43 is exposed, as illustrated in FIG. 9(a).

Next, in the method for manufacturing the microprojection unit 10, as illustrated in FIG. 9(b), the first lower opening plate 313D is moved upward and the first upper opening plate 312U is moved downward, and the base sheet 2A, in which the microprojection tool 1 has been formed, is sandwiched between the first lower opening plate 313D and the first upper opening plate 312U at a position more outward than the protrusion region 3R where the protrusions 3 are formed in the base sheet 2A. In this way, the base sheet 2A, in which the microprojection tool 1 has been formed, is sandwiched between the first lower opening plate 313D and the first upper opening plate 312U. Then, as illustrated in FIG. 9(c), in a state where the base sheet 2A is sandwiched, the base component fixing part 301 holding the base component 4 is passed through the opening 313a of the first lower opening plate 313D from the one surface 2D side (lower surface side) of the base sheet 2A, and the tip-end wall portion 43s of the peripheral wall portion 43 of the base component 4 is brought into contact with the one surface 2D of the base sheet 2A.

Further, as illustrated in FIG. 9(d), in a state where the base sheet 2A, in which the microprojection tool 1 has been formed, is sandwiched between the first lower opening plate 313D and the first upper opening plate 312U, the joining section 302 is passed through the opening 312a of the first upper opening plate 312U from the other surface 2U side (upper surface side) of the base sheet 2A, and the annular ring-shaped tip-end portion 302s of the joining section 302 is brought into contact with the other surface 2U of the base sheet 2A. It should be noted that the base sheet 2A, in which the microprojection tool 1 has been formed, may be sandwiched by the first lower opening plate 313D and the first upper opening plate 312U after bringing the annular ring-shaped tip-end portion 302s of the joining section 302 into contact with the other surface 2U of the base sheet 2A.

Then, by using the first lower opening plate 313D arranged on the one surface 2D (lower surface) side of the base sheet 2A and the first upper opening plate 312U arranged on the other surface 2U (upper surface) side of the base sheet 2A, joining is performed in a state where the base sheet 2A, in which the microprojection tool 1 has been formed, is sandwiched between the first lower opening plate 313D and the first upper opening plate 312U. In the method for manufacturing the microprojection unit 10, as illustrated in FIG. 9(e), in a state where the base sheet 2A, in which the microprojection tool 1 has been formed, is sandwiched between the first lower opening plate 313D and the first upper opening plate 312U, heating is performed at the annular ring-shaped tip-end portion 302s of the joining section 302, and the one surface 2D side (lower surface side) of the base sheet 2A, in which the microprojection tool 1 has been formed, and the tip end of the base component 4 are joined together by forming a joined region 5 in the microprojection unit 10 while causing the base component 4's tip-end wall portion 43s and a portion of the base sheet 2A located on the tip-end wall portion 43s of the base component 4's peripheral wall portion 43 to melt. After forming the joined region 5 in the microprojection unit 10, heating of the joining section 302 is stopped.

The heating temperature when causing the joining section 302 to contact the base sheet 2A is preferably 100° C. or higher, more preferably 120° C. or higher, and preferably 300° C. or lower, more preferably 250° C. or lower, and more specifically, preferably from 100° C. to 300° C., more preferably from 120° C. to 250° C.

The heating time when causing the joining section 302 to contact the base sheet 2A is preferably 0.1 seconds or greater, and preferably 5.0 seconds or less, and more specifically, preferably from 0.1 to 5.0 seconds.

The pressing force (pressurizing force) when causing the joining section 302 to contact the base sheet 2A is preferably 10 N or greater, and preferably 100 N or less, and more specifically, preferably from 10 to 100 N.

After the joining step, as illustrated in FIG. 9(f), the joining section 302 is moved upward, in the thickness direction, from the other surface 2U side (upper surface side) of the base sheet 2A. Then, as illustrated in FIG. 9(g), the first lower opening plate 313D is moved downward, and the first upper opening plate 312U is moved upward. In this way, the base sheet 2A, to which the base component 4 has been joined and in which the microprojection tool 1 has been provided, is formed on the base component fixing part 301.

Next, as illustrated in FIG. 6, the base sheet 2A, in which the microprojection tool 1 having the protrusions 3 has been formed and to which the base component 4 has been joined, is moved in the transporting direction. In the step after the joining step, the base sheet 2A manufactured in the joining step, to which the base component 4 has been joined, is cut along the contour 4L of the base component 4 at a position more inward than the base component 4's contour 4L in a planar view of the base sheet 2A as viewed from the microprojection tool 1 side, to manufacture the microprojection unit 10 (cutting step). Herein, "more inward than the base component 4's contour" means, in other words, more inward than the outer periphery of the bottom portion 41 of the base component 4. The cutting step is performed by using the member cutting section 400 for cutting the base sheet 2A and thereby manufacturing the microprojection unit 10.

Figure 10:
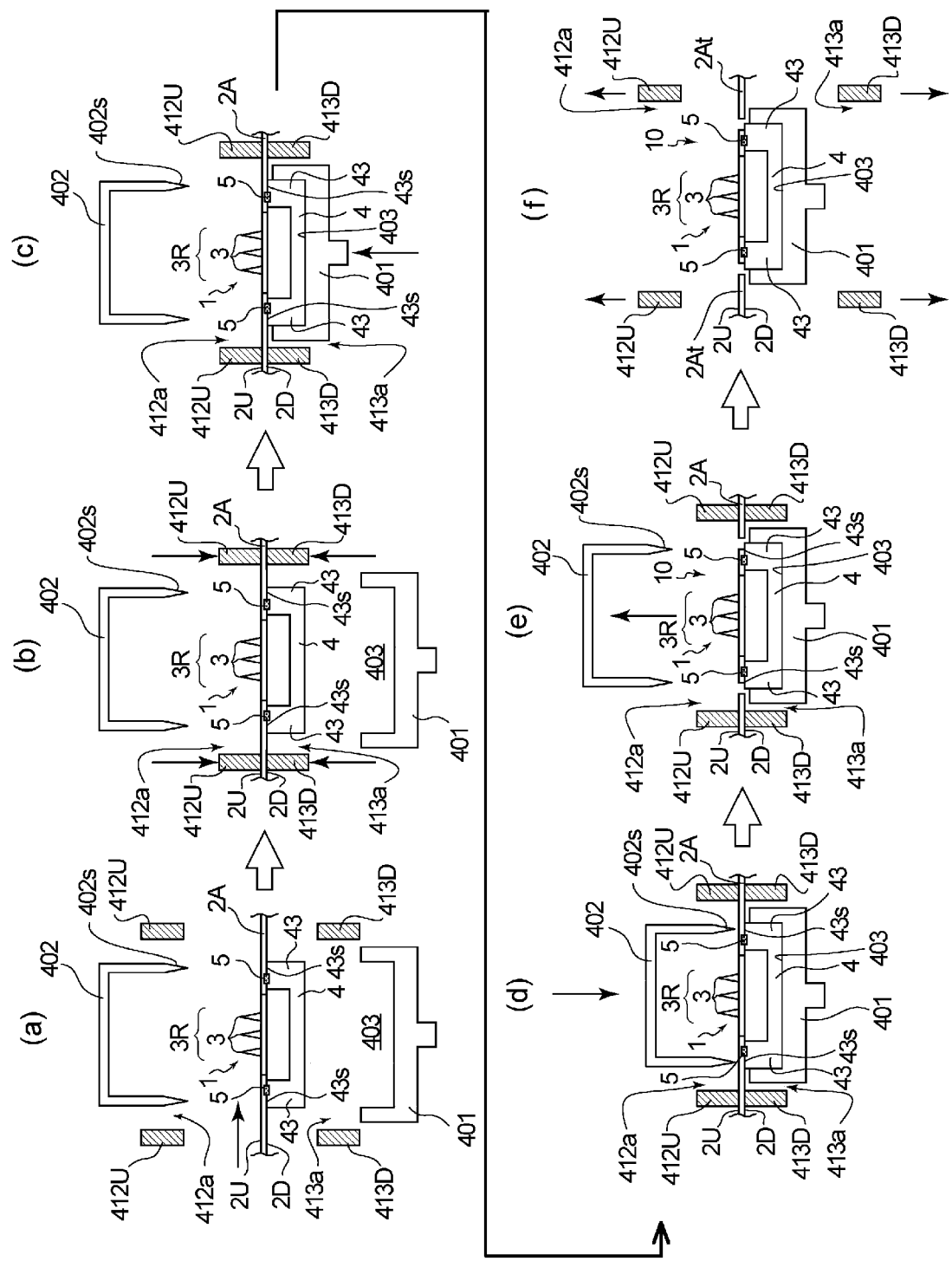
FIGS. 10(*a*) to 10(*f*) are diagrams illustrating a cutting step for forming a microprojection unit by performing cutting by employing the manufacturing device illustrated in FIG. 6.

In the manufacturing device 100, as illustrated in FIGS. 6 and 10, the member cutting section 400 includes: a base component fixing part 401 that fixes the base component 4; a cutting section 402 that cuts the base sheet 2A to which the base component 4 has been joined; and a second upper opening plate 412U and a second lower opening plate 413D that sandwich the base sheet 2A to which the base component 4 has been joined. The base component fixing part 401 has a depression 403 having a shape corresponding to the outer shape of the entire base component 4. In the microprojection unit 10, like the depression 303 of the base component fixing part 301 of the member joining section 300, the depression 403 is formed in a shape that fits with a cylindrical shape having a circular bottom portion 41.

As illustrated in FIGS. 6 and 10, the base component fixing part 401, having the depression 403, is arranged on the one surface 2D (lower surface) side of the base sheet 2A, and holds the base sheet 2A, to which the base component 4 has been joined, in a manner that the outer shape of the base component 4's bottom portion 41 side is fitted in the depression 403. The base component fixing part 401 may be fixed, but in this manufacturing device 100, like the base component fixing part 301 of the member joining section 300, the base component fixing part is movable in a direction separating from the direction contacting the base sheet 2A. More specifically, the base component fixing part 401 is made movable vertically in the thickness direction by an electric actuator (not illustrated).

The operation of the base component fixing part 401 is controlled by a control means (not illustrated) provided to the manufacturing device 100.

Like the base component fixing part 301 of the member joining section 300, the base component fixing part 401 may be made of the same material as that of the projecting mold part 11, and may be made, for example, of a synthetic resin.

The cutting section 402 is a section that cuts the base sheet 2A to which the base component 4 has been joined, and thereby manufactures the microprojection unit 10. As illustrated in FIGS. 6 and 10, the cutting section 402 annularly surrounds the protrusion region 3R, which is a region, in the base sheet 2A, where the protrusions 3 are formed, and has an annular ring-shaped tip-end portion 402s corresponding to the peripheral wall portion 43 of the base component 4. The cutting section 402 having the tip-end portion 402s is formed in a tubular shape with the tip-end portion 402s side opened.

As illustrated in FIGS. 6 and 10, the cutting section 402 is arranged on the other surface 2U (upper surface) side of the base sheet 2A. In the manufacturing device 100, the cutting section 402 is movable in a direction separating from the direction contacting the base sheet 2A. More specifically, the cutting section 402 is made movable vertically in the thickness direction by an electric actuator (not illustrated).

The operation of the cutting section 402 is controlled by a control means (not illustrated) provided to the manufacturing device 100.

Examples of means for cutting in the cutting step include means such as a punching blade or a laser. In the manufacturing device 100, the cutting means in the cutting section 402 is a cutting means consisting of a punching blade. Preferably, the blade at the tip-end portion 402s of the cutting section 402 is arranged within the range of the thickness T4 of the tip-end wall portion 43s of the peripheral wall portion 43 of the base component 4. In the manufacturing device 100, the blade at the tip-end portion 402s of the cutting section 402 is arranged at a position more inward than the contour 4L of the base component 4—i.e., the outer periphery of the bottom portion 41—and more outward than the outer-side peripheral edge of the continuous joined region 5. Note that a laser is a cutting means that, by irradiation with a laser beam, melts and cuts the base sheet 2A at the same time as melting and bonding the materials of the base sheet 2A and the base component 4 by heat as described above.

As illustrated in FIG. 10, like the first lower opening plate 313D of the member joining section 300, the second lower opening plate 413D is arranged on the one surface 2D (lower surface) side of the base sheet 2A, and is formed of a board-like plate having a single opening 413a. The opening area of the opening 413a is formed greater than the planar area of the base component fixing part 401 so that the base component fixing part 401 can be passed therethrough when the base component fixing part 401 is moved upward in the thickness direction from the one surface 2D side.

As illustrated in FIG. 10, like the first upper opening plate 312U of the member joining section 300, the second upper opening plate 412U is arranged on the other surface 2U (upper surface) side of the base sheet 2A, and is formed of a board-like plate having a single opening 412a. The opening area of the opening 412a is formed greater than the planar area of the cutting section 402 so that the cutting section 402 can be passed therethrough when the cutting section 402 is moved downward in the thickness direction from the other surface 2U side.

The second lower opening plate 413D and the second upper opening plate 412U are movable in a direction separating from the direction contacting the base sheet 2A. In the manufacturing device 100, the second lower opening plate 413D and the second upper opening plate 412U are made movable vertically in the thickness direction by an electric actuator (not illustrated).

The operation of the second lower opening plate 413D and the second upper opening plate 412U is controlled by a control means (not illustrated) provided to the manufacturing device 100.

In the method for manufacturing the microprojection unit 10, as illustrated in FIGS. 10(a) and 10(b), the second lower opening plate 413D is moved upward and the second upper opening plate 412U is moved downward, and the base sheet 2A, to which the base component 4 has been joined and in which the microprojection tool 1 has been provided, is sandwiched between the second lower opening plate 413D and the second upper opening plate 412U at a position, within the base sheet 2A, more outward than the contour 4L of the base component 4. In this way, the base sheet 2A, to which the base component 4 has been joined, is sandwiched between the second lower opening plate 413D and the second upper opening plate 412U.

Then, in the method for manufacturing the microprojection unit 10, as illustrated in FIG. 10(c), in a state where the base sheet 2A is sandwiched between the second lower opening plate 413D and the second upper opening plate 412U, the base component fixing part 401 is passed through the opening from the one surface 2D side (lower surface side) of the base sheet 2A. Then, the base sheet 2A, to which the base component 4 has been joined and in which the microprojection tool 1 has been provided, is held by fitting the outer shape on the bottom portion 41 side of the base component 4 within the depression 403 of the base component fixing part 401.

Then, the second lower opening plate 413D arranged on the one surface 2D (lower surface) side of the base sheet 2A and the second upper opening plate 412U arranged on the other surface 2U (upper surface) side of the base sheet 2A are used, and the base sheet 2A is cut, thus manufacturing a microprojection unit 10, in a state where the base sheet 2A, to which the base component 4 has been joined, is sandwiched between the second lower opening plate 413D and the second upper opening plate 412U. In the method for manufacturing the microprojection unit 10, as illustrated in FIG. 10(d), in a state where the base sheet 2A, to which the base component 4 has been joined, is sandwiched between the second lower opening plate 413D and the second upper opening plate 412U, the cutting section 402 is passed through the opening 412a of the second upper opening plate 412U from the other surface 2U side (upper surface side) of the base sheet 2A, and the microprojection unit 10 is manufactured by bringing the blade at the tip-end portion 402s of the cutting section 402 into contact with the other surface 2U of the base sheet 2A to cut the base sheet 2A along the contour 4L of the base component 4 at a position more inward than the base component 4's contour 4L in a planar view from the microprojection tool 1 side. In the cutting step of the method for manufacturing the microprojection unit 10, the microprojection unit 10 is manufactured by cutting the base sheet 2A on the tip-end wall portion 43s of the peripheral wall portion 43, which is arranged around the outer periphery of the liquid retention space 4k of the base component 4.

After the cutting step, as illustrated in FIG. 10(e), the cutting section 402 is moved upward, in the thickness direction, from the other surface 2U side (upper surface side) of the base sheet 2A. Then, as illustrated in FIG. 10(f), the second lower opening plate 413D is moved downward, and the second upper opening plate 412U is moved upward. Thereafter, a trimmed portion 2At of the base sheet 2A sandwiched between the second lower opening plate 413D and the second upper opening plate 412U is removed after moving the second lower opening plate 413D downward and moving the second upper opening plate 412U upward. In this way, the microprojection unit 10 is formed on the base component fixing part 401.

The microprojection unit 10 formed as above is then removed from the base component fixing part 401 and transported downstream in the transporting direction. By repeating the aforementioned steps, microprojection units 10 can be manufactured continuously and efficiently.

The microprojection unit 10 manufactured as above may be further shaped into a predetermined shape in subsequent steps.

As described above, as illustrated in FIG. 6, the manufacturing method for manufacturing the microprojection unit 10 by using the manufacturing device 100 involves: a joining step of joining the one surface 2D side (lower surface side) of the base sheet 2A, in which the microprojection tool 1 has been formed, and the tip end of the base component 4; and thereafter, a subsequent cutting step of cutting the base sheet 2A manufactured in the joining step, to which the base component 4 has been joined, along the contour 4L of the base component 4 at a position more inward than the base component 4's contour 4L in a planar view of the base sheet 2A as viewed from the microprojection tool 1 side, to manufacture the microprojection unit 10. As described above, the base component 4, which is a section to be attached to an external cylinder, is a member separate from the microprojection tool 1, and thus, the shape of the base component 4 is less prone to be restricted. Further, the microprojection unit 10, including the microprojection tool 1 and the base component 4, can be manufactured efficiently and accurately.

According to the manufacturing method for manufacturing the microprojection unit 10 by using the manufacturing device 100, the blade at the tip-end portion 402s of the cutting section 402 is arranged within the range of the thickness T4 of the tip-end wall portion 43s of the peripheral wall portion 43 of the base component 4, and, in the cutting step, the microprojection unit 10 is manufactured by cutting the base sheet 2A on the tip-end wall portion 43s of the peripheral wall portion 43, which is arranged around the outer periphery of the liquid retention space 4k of the base component 4, as illustrated in FIG. 9. Thus, tip-end wall portion 43s of the base component 4's peripheral wall portion 43 can serve as a receiving member against which the blade at the tip-end portion 402s of the cutting section 402 is pressed, and thus, there is no need to provide a separate receiving member. In this way, the microprojection unit 10 can be manufactured efficiently and accurately while suppressing increases in cost.

According to the manufacturing method for manufacturing the microprojection unit 10 by using the manufacturing device 100, as illustrated in FIG. 7, the protrusion forming step, the cooling step, and the release step of the microprojection tool forming step are performed in a state where the base sheet 2A is sandwiched between the opening plate 12U and the second opening plate 13D, which are warp-suppressing means. Thus, the hollow-interior microprojection tool 1 can be manufactured accurately.

According to the manufacturing method for manufacturing the microprojection unit 10 by using the manufacturing device 100, as illustrated in FIG. 7, only the contact section TP in the base sheet 2A, where the projecting mold part 11 contacts the base sheet, is softened by frictional heat when generating ultrasonic vibration which is the heating means (not illustrated) of the projecting mold part 11. Thus, microprojection tools 1 can be manufactured efficiently and continuously while saving energy.

According to the manufacturing method for manufacturing the microprojection unit 10 by using the manufacturing device 100, the shape of the microprojection tool 1 can be controlled freely by controlling at least one of: the conditions of the heating means (not illustrated) of the projecting mold part 11; the insertion height of the projecting mold part 11 into the base sheet 2A in the protrusion forming step; the softening time of the contact section TP in the base sheet 2A; the insertion speed of the projecting mold part 11 into the base sheet 2A; the shape of the projecting mold part 11; and cooling conditions in the cooling step.

According to the manufacturing method for manufacturing the microprojection unit 10 by using the manufacturing device 100, as illustrated in FIG. 9, the joined region 5 of the microprojection unit 10 is formed by using the joining section 302 in a state where the base sheet 2A, in which the microprojection tool 1 has been formed, is sandwiched between the first lower opening plate 313D and the first upper opening plate 312U. Thus, the one surface 2D side (lower surface side) of the base sheet 2A, in which the microprojection tool 1 has been formed, and the tip end of the base component 4 can be joined accurately.

According to the manufacturing method for manufacturing the microprojection unit 10 by using the manufacturing device 100, as illustrated in FIG. 10, cutting is performed with the cutting section 402, thereby manufacturing the microprojection unit 10, in a state where the base sheet 2A, to which the base component 4 has been joined, is sandwiched between the second lower opening plate 413D and the second upper opening plate 412U. Thus, the microprojection unit 10 can be manufactured accurately.

The present invention has been described above according to preferred embodiments thereof, but the invention is not limited to the foregoing embodiments, and can be modified as appropriate.

For example, as illustrated in FIG. 6, the method for manufacturing the microprojection unit 10 by using the aforementioned manufacturing device 100 involves: a joining step of joining the one surface 2D side (lower surface side) of the base sheet 2A, in which the microprojection tool 1 has been formed, and the tip end of the base component 4; and thereafter, a subsequent cutting step of cutting the base sheet 2A manufactured in the joining step, to which the base component 4 has been joined, to manufacture the microprojection unit 10; however, the joining step and the cutting step may be in the same step. That is, the method for manufacturing the microprojection unit 10 may involve: a microprojection tool forming step of forming a microprojection tool 1; and a joining-cutting step of joining the one surface 2D (lower surface) side of the base sheet 2A, in which the microprojection tool 1 has been formed, and the tip end of the base component 4, and simultaneously cutting the base sheet 2A, along the contour 4L of the base component 4 at a position more inward than the base component 4's contour 4L in a planar view of the base sheet 2A as viewed from the microprojection tool 1 side, to manufacture the microprojection unit 10. An example of a means that performs joining simultaneously with cutting in the joining-cutting step for manufacturing the microprojection unit 10 is a means such as a laser.

In the method for manufacturing the microprojection unit 10, in the joining-cutting step, a third lower opening plate arranged on the one surface 2D side (lower surface side) of the base sheet 2A and a third upper opening plate arranged on the other surface side (upper surface side) of the base sheet may be used, and, in a state where the base sheet 2A, in which the protrusions 3 have been formed, is sandwiched between the third lower opening plate and the third upper opening plate by moving the third lower opening plate above the base sheet 2A and moving the third upper opening plate below the base sheet 2A, the one surface 2D (lower surface) side of the base sheet 2A and the tip end of the base component 4 may be joined together while simultaneously cutting the base sheet 2A, to manufacture the microprojection unit 10. After the joining-cutting step, the third lower opening plate may be moved downward and the third upper opening plate may be moved upward.

In the method for manufacturing the microprojection unit 10, in the microprojection tool forming step, a second opening plate 13D arranged on the one surface 2D side (lower surface side) of the base sheet 2A and an opening plate 12U arranged on the other surface 2U side (upper surface side) of the base sheet 2A may be used, and the protrusions 3 may be formed in a state where the base sheet 2A is sandwiched between the opening plate 12U and the second opening plate 13D by moving the opening plate 12U to above the base sheet 2A and moving the second opening plate 13D to below the base sheet 2A. Then, after the microprojection tool forming step, the second opening plate 13D may be moved downward and the opening plate 12U may be moved upward, and the base sheet 2A in which the protrusions 3 have been formed may be transported to the next step.

In the manufacturing method for manufacturing the microprojection unit 10 by using the aforementioned manufacturing device 100, an ultrasonic vibration device is used as the heating means of the projecting mold part 11, but a heater may be used instead.

In the manufacturing method for manufacturing the microprojection unit 10 by using the aforementioned manufacturing device 100, the protrusions 3, the microprojection tool 1, and the microprojection unit 10 are formed by intermittently transporting a continuous base sheet 2A, as illustrated in FIG. 6. Instead, the protrusions 3, the microprojection tool 1, and the microprojection unit 10 may be molded by continuously transporting the continuous base sheet 2A and using a microprojection tool forming section 200, a member joining section 300, and a member cutting section 400 of the box-motion type that follow an endless track. Further, in the manufacturing method for manufacturing the microprojection unit 10, the protrusions 3, the microprojection tool 1, and the microprojection unit 10 may be molded by using a microprojection tool forming section and a joining-cutting section of the box-motion type that follow an endless track.

In the manufacturing method for manufacturing the microprojection unit 10 by using the aforementioned manufacturing device 100, as illustrated in FIG. 6, a projecting mold part 11 that is inserted into the base sheet 2A from below toward above in the thickness direction is used. Instead, the protrusions 3 may be molded by using a projecting mold part 11 that is inserted into the base sheet 2A from above toward below in the thickness direction.

In the manufacturing method for manufacturing the microprojection unit 10 by using the aforementioned manufacturing device 100, as illustrated in FIG. 6, the base sheet 2A is processed in a sandwiched state by using the opening plate 12U and the second opening plate 13D in the microprojection tool forming step and by using the third lower opening plate and the third upper opening plate in the joining-cutting step. Processing, however, may be performed without using these opening plates.

The invention is described below according to a preferred embodiment thereof with reference to the drawings.

Figure 11:
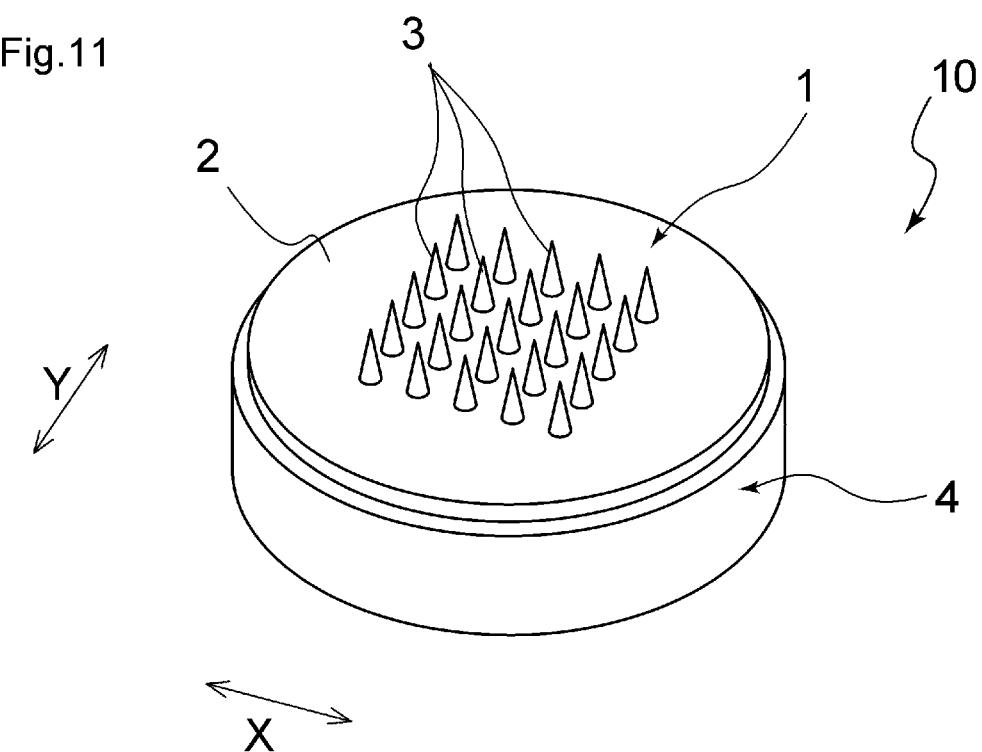
FIG. 11 is a schematic perspective view of a microprojection unit which is a preferred embodiment of a microprojection unit according to the invention.
Figure 12:
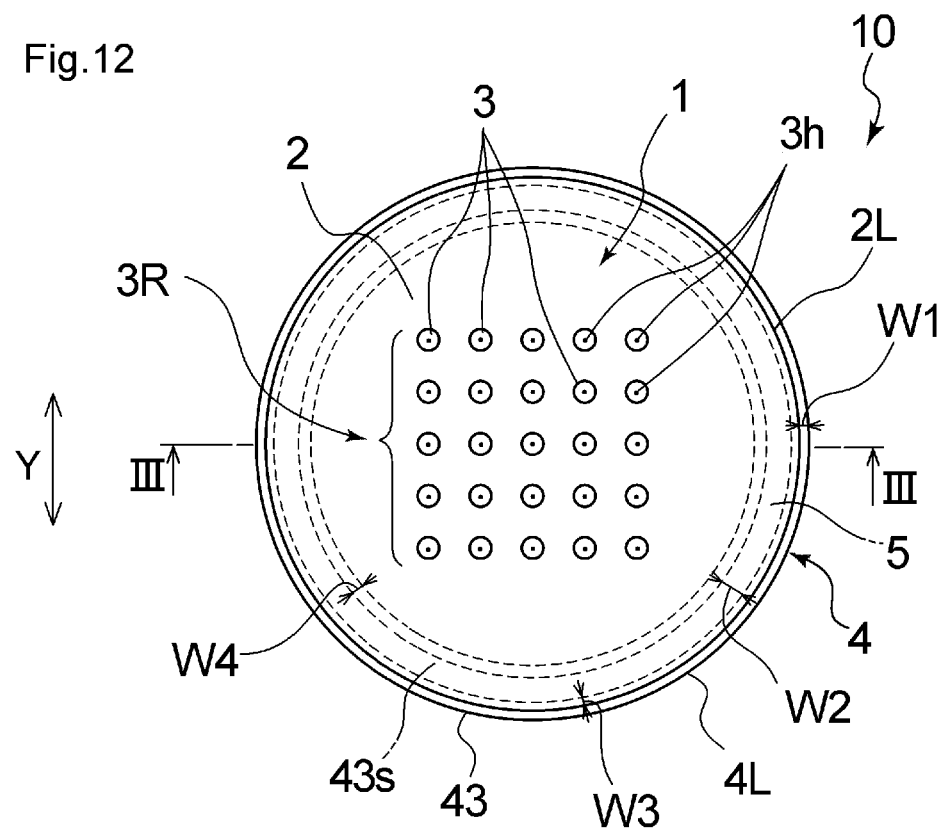
FIG. 12 is a plan view of the microprojection unit illustrated in FIG. 11 in a planar view from the microprojection tool side.
Figure 13:
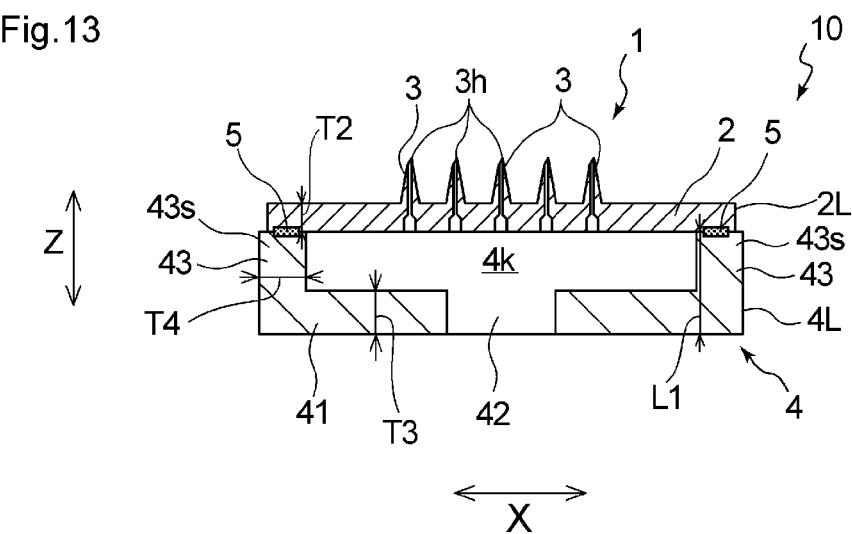
FIG. 13 is a cross-sectional view taken along line illustrated in FIG. 12.

A microprojection unit 10 according to a preferred embodiment of the microprojection unit of the present invention (also referred to hereinafter simply as "microprojection unit 10") includes: a microprojection tool 1 including, on a base 2, protrusions 3 with a hollow interior; and a base component 4 having a liquid retention space 4k (see FIG. 13) that is in communication with the interior of the protrusions 3 through the base 2. The microprojection unit is formed by joining the microprojection tool 1 to a tip end of the base component 4. FIG. 11 illustrates a perspective view of the microprojection unit 10. FIG. 12 illustrates a plan view of the microprojection unit 10. FIG. 13 illustrates a cross-sectional view of the microprojection unit 10.

As regards the protrusions 3 of the microprojection tool 1, the number of protrusions 3, the arrangement of the protrusions 3, and the shape of the protrusion 3 are not particularly limited; in this microprojection unit 10, as illustrated in FIGS. 11 and 12, twenty-five truncated circular-conic protrusions 3 are arranged on the upper surface of the sheet-like base 2. The arrayed twenty-five protrusions 3 are arranged in five rows along the second direction (corresponding to the Y direction in the figures), which is the direction in which the later-described base sheet 2A is transported (corresponding to the longitudinal direction of the base sheet 2A), and in five columns along the first direction (corresponding to the X direction in the figures), which is the direction orthogonal to the second direction, i.e., the transporting direction, and which is the width direction of the base sheet 2A being transported. It should be noted that the thickness direction of the microprojection unit 10 is described as the Z direction. FIG. 14(a) is a perspective view of the microprojection tool 1, focusing on a single protrusion 3 among the protrusions 3 of the microprojection tool 1, and FIG. 14(b) is a cross-sectional view taken along line Iv-Iv illustrated in FIG. 14(a).

The microprojection tool 1 illustrated in FIG. 14(a) includes: a sheet-like base 2; and a single circular-conic protrusion 3 provided so as to stand up on the base 2's upper surface (the surface on the opposite side from the base 2's surface opposing the base component 4). The microprojection tool 1 does not require an opening at the tip-end side, but in this microprojection unit 10, as illustrated in FIG. 14(b), an opening 3h is provided, and a space 3k penetrating from the base 2 to the opening 3h is formed in the interior of the protrusion 3. In the microprojection unit 10, the interior space 3k of the protrusion 3 is formed in a circular-conic shape corresponding to the outer shape of the protrusion 3. It should be noted that, although the protrusion 3 in this microprojection unit 10 is circular-conic, the protrusion may have a shape other than a circular-conic shape, such as the shape of a truncated circular cone, a circular cylinder, a prism, a pyramid, or a truncated pyramid.

In cases where the protrusion 3 is to be used as a microneedle, in order for the tip end thereof to reach, for example, the stratum corneum, which is the outermost layer, or the dermis, which is a deeper layer, the protrusion height H1 (cf. FIG. 14(b)) of the protrusion is preferably 0.01 mm or greater, more preferably 0.02 mm or greater, and preferably 10 mm or less, more preferably 5 mm or less, further preferably 3 mm or less, and more specifically, preferably from 0.01 to 10 mm, more preferably from 0.01 to 5 mm, further preferably from 0.02 to 3 mm. The average thickness T1 of the protrusion 3 is preferably 0.005 mm or greater, more preferably 0.01 mm or greater, and preferably 1.0 mm or less, more preferably 0.5 mm or less, and more specifically, preferably from 0.005 to 1.0 mm, more preferably from 0.01 to 0.5 mm.

The tip end size, in diameter, of the protrusion 3 is preferably 0.001 mm or greater, more preferably 0.005 mm or greater, and preferably 0.5 mm or less, more preferably 0.3 mm or less, and more specifically, preferably from 0.001 to 0.5 mm, more preferably from 0.005 to 0.3 mm. The tip end diameter of the protrusion 3 of the microprojection tool 1 is measured as follows.

{Measurement of Tip End Diameter of Protrusion 3}

In cases where the tip end of the protrusion 3 is not opened, the tip end portion of the protrusion 3 of the microprojection tool 1 is observed in an enlarged state under a predetermined magnification using a scanning electron microscope (SEM) or a microscope, as in the SEM image illustrated in FIG. 15(a), for example.

Next, as illustrated in FIG. 15(a), an imaginary straight line 1La is extended along the straight-line portion of one lateral side 1a of the two lateral sides 1a, 1b. Also, an imaginary straight line 1Lb is extended along the straight-line portion of the other lateral side 1b. The point where the lateral side 1a separates from the imaginary straight line 1La on the tip end side is defined as a first tip end point 1a1, and the point where the other lateral side 1b separates from the imaginary straight line 1Lb is defined as a second tip end point 1b 1. The length L of a straight line that connects the first tip end point 1a1 and the second tip end point 1b 1 defined as above is measured using a scanning electron microscope (SEM) or a microscope, and the measured length of the straight line is defined as the tip end diameter of the microprojection tool 1. In cases where there is an opening 3h at the tip end of the protrusion 3 as in this microprojection unit 10, as illustrated in FIG. 15(b), imaginary straight lines 1La, 1Lb are rendered assuming that the protrusion 3 has a tip end on the opening side and the intersection point of the imaginary lines is defined as the apex of the protrusion 3, and the aforementioned method illustrated in FIG. 15(a) is employed to measure the tip end diameter.

From the viewpoint of easily supplying an agent with the microprojection unit 10, it is preferable that the opening 3h has an opening area of preferably 0.7 $\mu m^2$ or greater, more preferably 20 $\mu m^2$ or greater, and preferably 200000 $\mu m^2$ or less, more preferably 70000 $\mu m^2$ or less, and more specifically, preferably from 0.7 to 200000 $\mu m^2$, more preferably from 20 to 70000 $\mu m^2$.

As illustrated in FIGS. 11 and 12, the twenty-five protrusions 3 arranged on the upper surface of the sheet-like base 2 are preferably arranged such that the center-to-center distance in the second direction is uniform and the center-to-center distance in the first direction is uniform, and preferably, the center-to-center distance in the second direction is the same as the center-to-center distance in the first direction. Preferably, the center-to-center distance in the second direction between the protrusions 3 is preferably 0.01 mm or greater, more preferably 0.05 mm or greater, and preferably 10 mm or less, more preferably 5 mm or less, and more specifically, preferably from 0.01 to 10 mm, more preferably from 0.05 to 5 mm. The center-to-center distance in the first direction between the protrusions 3 is preferably 0.01 mm or greater, more preferably 0.05 mm or greater, and preferably 10 mm or less, more preferably 5 mm or less, and more specifically, preferably from 0.01 to 10 mm, more preferably from 0.05 to 5 mm.

The base 2 is formed in a sheet shape having a uniform thickness. In cases where the base 2 and the base component 4 are formed of the same type of material, from the viewpoint of easily allowing the base 2 to bend so as to project outward when a liquid is introduced into the liquid retention space 4k and inner pressure is applied, it is preferable that the thickness T2 (see FIG. 14(b)) of the base 2 is thinner than the later-described thickness T3 (see FIG. 13) of the bottom portion 41 of the base component 4, and it is preferable that the ratio (T2/T3) of the thickness T2 of the base 2 to the thickness T3 of the bottom portion 41 of the base component 4 is preferably 0.001 or greater, more preferably 0.01 or greater, and preferably 1 or less, more preferably 0.5 or less, and preferably from 0.001 to 1, more preferably from 0.01 to 0.5. The thickness T2 of the base 2 is preferably 0.01 mm or greater, more preferably 0.02 mm or greater, and preferably 1.0 mm or less, more preferably 0.7 mm or less, and more specifically, preferably from 0.01 to 1.0 mm, more preferably from 0.02 to 0.7 mm.

As illustrated in FIG. 12, the microprojection unit 10 has, on the upper surface of the base 2, a protrusion region 3R which is a region having the twenty-five protrusions 3—i.e., a region in which the twenty-five protrusions 3 are formed. Herein, the protrusion region 3R refers to a region surrounded by the outermost protrusions 3 in a planar direction including the first direction and the second direction in a planar view of the microprojection unit 10 as viewed from the microprojection tool 1 side. The protrusion region 3R is formed more inward than a later-described joined region 5 with the base component 4.

As illustrated in FIG. 13, the base component 4 has a liquid retention space 4k that is in communication with the interior space 3k of the protrusions 3 through the base 2. The base component 4 includes: a bottom portion 41 that forms a lower surface on the opposite side from an upper surface where the joined region 5 with the microprojection tool 1 is formed; a liquid supply path 42 that penetrates the bottom portion 41 and supplies a liquid into the liquid retention space 4k; and a peripheral wall portion 43 that is arranged so as to extend over the entire outer periphery of the bottom portion 41 and is arranged in a standing condition on the upper surface (the surface on the microprojection tool 1 side) of the bottom portion 41. The space surrounded by the microprojection tool 1's base 2, the bottom portion 41, and the peripheral wall portion 43 constitutes the liquid retention space 4k. As described above, the peripheral wall portion 43 is arranged around the outer periphery of the liquid retention space 4k. The microprojection unit 10 is formed such that, for example, a syringe for supplying a liquid can be connected to a supply opening of the liquid supply path 42 of the base component 4.

In relation to the base component 4, the shape of the contour 4L of the base component 4 in a planar view of the microprojection unit 10 viewed from the microprojection tool 1 side—i.e., the outer peripheral shape of the bottom portion 41—is not particularly limited; in this microprojection unit 10, the shape is circular, as illustrated in FIG. 12. In the microprojection unit 10 illustrated in FIG. 11, the entire outer shape of the base component 4 is formed in a circular cylindrical shape, with the bottom portion 41 being circular. Note that, although the shape of the contour 4L of the base component 4 is circular in this microprojection unit 10, the shape may be, for example, elliptical, rhombic, triangular, rectangular, or pentagonal, other than circular. The entire shape of the base component 4 may be, for example, a circular-conic shape, a prism, or a pyramid, other than a circular cylinder.

From the viewpoint of easily allowing the base 2 to bend so as to project outward when a liquid is introduced into the liquid retention space 4k and inner pressure is applied, it is preferable that, in the base component 4, the thickness T3 (see FIG. 13) of the base component 4's bottom portion 41 is greater than the thickness T2 of the base 2, and is preferably 1.0 mm or greater, more preferably 1.5 mm or greater, and preferably 10 mm or less, more preferably 5 mm or less, and more specifically, preferably from 1.0 to 10 mm, more preferably from 1.5 to 5 mm.

In the base component 4, from the same viewpoint, it is preferable that the thickness T4 (see FIG. 13) of the base component 4's peripheral wall portion 43 is greater than the thickness T2 of the base 2, and is preferably 1.0 mm or greater, more preferably 1.5 mm or greater, and preferably 10 mm or less, more preferably 5 mm or less, and more specifically, preferably from 1.0 to 10 mm, more preferably from 1.5 to 5 mm.

In the microprojection unit 10, as illustrated in FIG. 13, in a cross-sectional view of the microprojection unit 10 along the thickness direction, the thickness T2 of the base 2 of the microprojection tool 1 is formed smaller than the length L1, in the thickness direction, of the base component 4 in the joined region 5 where the base component 4 and the microprojection tool 1 have been joined together. FIG. 13 is a cross-sectional view along line illustrated in FIG. 12, and, in cases where the base component 4 is circular in a planar view of the microprojection unit 10 viewed from the microprojection tool 1 side, the figure is a cross-sectional view in which the line passes through the center of the circle of the base component 4.

From the viewpoint of easily allowing the base 2 to bend so as to project outward when a liquid is introduced into the liquid retention space 4k and inner pressure is applied, it is preferable that the ratio (T2/L1) of the thickness T2 of the base 2 of the microprojection tool 1 to the length L1, in the thickness direction, of the base component 4 at the position of the joined region 5 is preferably 0.005 or greater, more preferably 0.01 or greater, and preferably 0.5 or less, more preferably 0.3 or less, and preferably from 0.005 to 0.5, more preferably from 0.01 to 0.3. It is preferable that the length L1, in the thickness direction, of the base component 4 is preferably 2 mm or greater, more preferably 3 mm or greater, and preferably 20 mm or less, more preferably 15 mm or less, and more specifically, preferably from 2 to 20 mm, more preferably from 3 to 15 mm.

In the microprojection unit 10, as illustrated in FIGS. 12 and 13, the contour of the microprojection tool 1—i.e., the contour 2L of the base 2 of the microprojection tool 1—is arranged at a position more inward than the contour 4L of the base component 4 in a planar view from the microprojection tool 1 side. From the viewpoint of improving appearance and the feel upon use, it is preferable that the contour 2L of the base 2 of the microprojection tool 1 is arranged on the inner side of the contour 4L of the base component 4 with a spacing W1 therebetween of preferably 0.05 mm or greater, more preferably 0.1 mm or greater, and preferably 5 mm or less, more preferably 3 mm or less, and more specifically, preferably from 0.05 to 5 mm, more preferably from 0.1 to 3 mm.

In the microprojection unit 10, as illustrated in FIG. 12, a joined region 5 where the base component 4 and the microprojection tool 1 have been joined together is provided at a position within the contour of the microprojection tool—i.e., the contour 2L of the base 2 of the microprojection tool 1—in a planar view from the microprojection tool 1 side. The joined region 5 is formed as a continuous joined region on a tip-end wall portion 43s of the peripheral wall portion 43 arranged so as to extend over the outer periphery of the liquid retention space 4k of the base component 4, and is arranged in an annular ring shape over the entire region of the outer periphery of the liquid retention space 4k. Herein, the "position within the contour 2L" either means that the contour 2L of the base 2 of the microprojection tool 1 matches the outer-side peripheral edge of the continuous joined region 5, or the outer-side peripheral edge of the continuous joined region 5 is arranged more inward than the contour 2L of the base 2 of the microprojection tool 1.

In the microprojection unit 10, as illustrated in FIG. 12, from the viewpoint of improving adhesion strength, appearance, and the feel upon use, it is preferable that the width W2 of the continuous joined region 5 in a planar view from the microprojection tool 1 side is preferably 0.5 mm or greater, more preferably 1 mm or greater, and preferably 5 mm or less, more preferably 3 mm or less, and more specifically, preferably from 0.5 to 5 mm, more preferably from 1 to 3 mm.

In the microprojection unit 10, as illustrated in FIG. 12, from the viewpoint of improving cutting stability, appearance, and the feel upon use, it is preferable that, in a planar view from the microprojection tool 1 side, the spacing W3 between the contour 2L of the base 2 and the outer-side peripheral edge of the joined region 5 is arranged at a spacing W3 of preferably 0.05 mm or greater, more preferably 0.1 mm or greater, and preferably 5 mm or less, more preferably 3 mm or less, and more specifically, preferably from 0.05 to 5 mm, more preferably from 0.1 to 3 mm.

In the microprojection unit 10, as illustrated in FIGS. 12 and 13, the base component 4 includes a bottom portion 41 surrounding the liquid retention space 4k, and a peripheral wall portion 43 arranged so as to extend over the entire outer periphery of the bottom portion 41; the base component 4 is joined with the microprojection tool 1 on an upper surface of the peripheral wall portion 43 opposing the microprojection tool 1; and a non-joined region that is not joined with the microprojection tool 1 is provided on the liquid retention space 4k side of the upper surface. Stated differently, by providing a non-joined region which is a region where liquid can enter between the microprojection tool 1 and the tip-end wall portion 43s, the base 2 is allowed to easily bend so as to project outward when an inner pressure is applied. From the viewpoint of causing the protrusions 3 to bend so as to project outward and thereby improving puncturability to the skin, it is preferable that the spacing W4 between the inner-side peripheral edge of the joined region 5 on the protrusion region 3R side and the inner wall of the tip-end wall portion 43s of the peripheral wall portion 43 is arranged at a spacing W4 of preferably 0.05 mm or greater, more preferably 0.1 mm or greater, and preferably 5 mm or less, more preferably 3 mm or less, and more specifically, preferably from 0.05 to 5 mm, more preferably from 0.1 to 3 mm.

Figure 16:
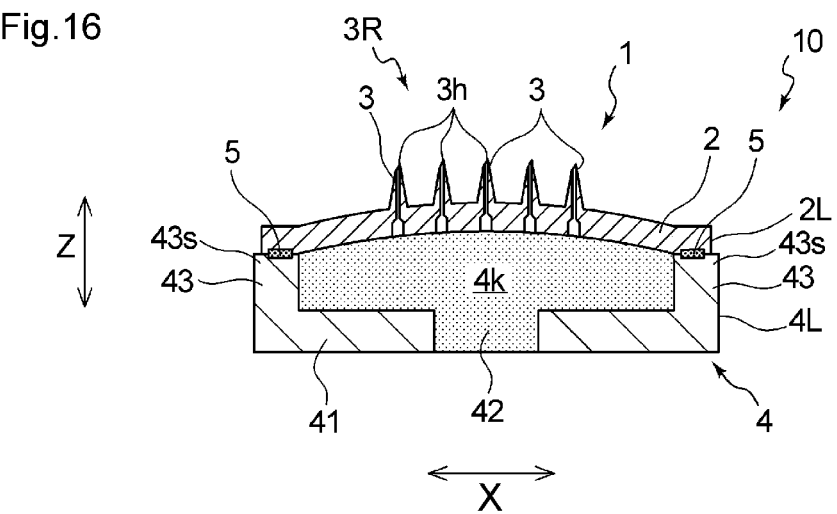
FIG. 16 is a schematic cross-sectional view illustrating a state in which the microprojection unit illustrated in FIG. 11 is used.

In the microprojection unit 10, as illustrated in FIGS. 11 and 13, the microprojection tool 1 having the protrusions 3 on the base 2 is a separate member from the base component 4, and the microprojection tool 1 is joined to the tip end of the base component 4. Thus, the shapes of the microprojection tool 1 and the base component 4 are less prone to be restricted, and there is a high degree of freedom in selecting the base component 4. Further, in this microprojection unit 10, upon use, when a liquid is supplied from a syringe etc. into the liquid retention space 4k of the base component 4 through the liquid supply path 42, and the liquid is introduced into the liquid retention space 4k and an inner pressure is applied as illustrated in FIG. 16, the region provided with the protrusions 3 on the base 2 of the microprojection tool 1 bends so as to project outward. The region provided with the protrusions 3 on the base 2 of the microprojection tool 1 bends so as to project outward as described above, and thus, the puncturability of the twenty-five protrusions 3 arranged on the upper surface of the base 2 is improved and also the feel upon use is improved. Particularly, as regards the twenty-five protrusions 3 arranged on the upper surface of the base 2, the puncturing direction of the twenty-four protrusions 3 other than the central protrusion 3 will extend radially from the central protrusion, thus improving the puncturability of the protrusions 3 and improving the feel upon use.

Particularly, in the microprojection unit 10, in a cross-sectional view as illustrated in FIG. 13, the thickness T2 of the base 2 of the microprojection tool 1 is formed smaller than the length L1, in the thickness direction, of the base component 4 in the joined region 5. Since the base is formed as described above so as to be outwardly bendable, the base 2 of the microprojection tool 1 can easily bend and follow the projections and depressions on the user's skin, thus improving the puncturability of the protrusions 3 and improving the feel upon use.

Figure 17:
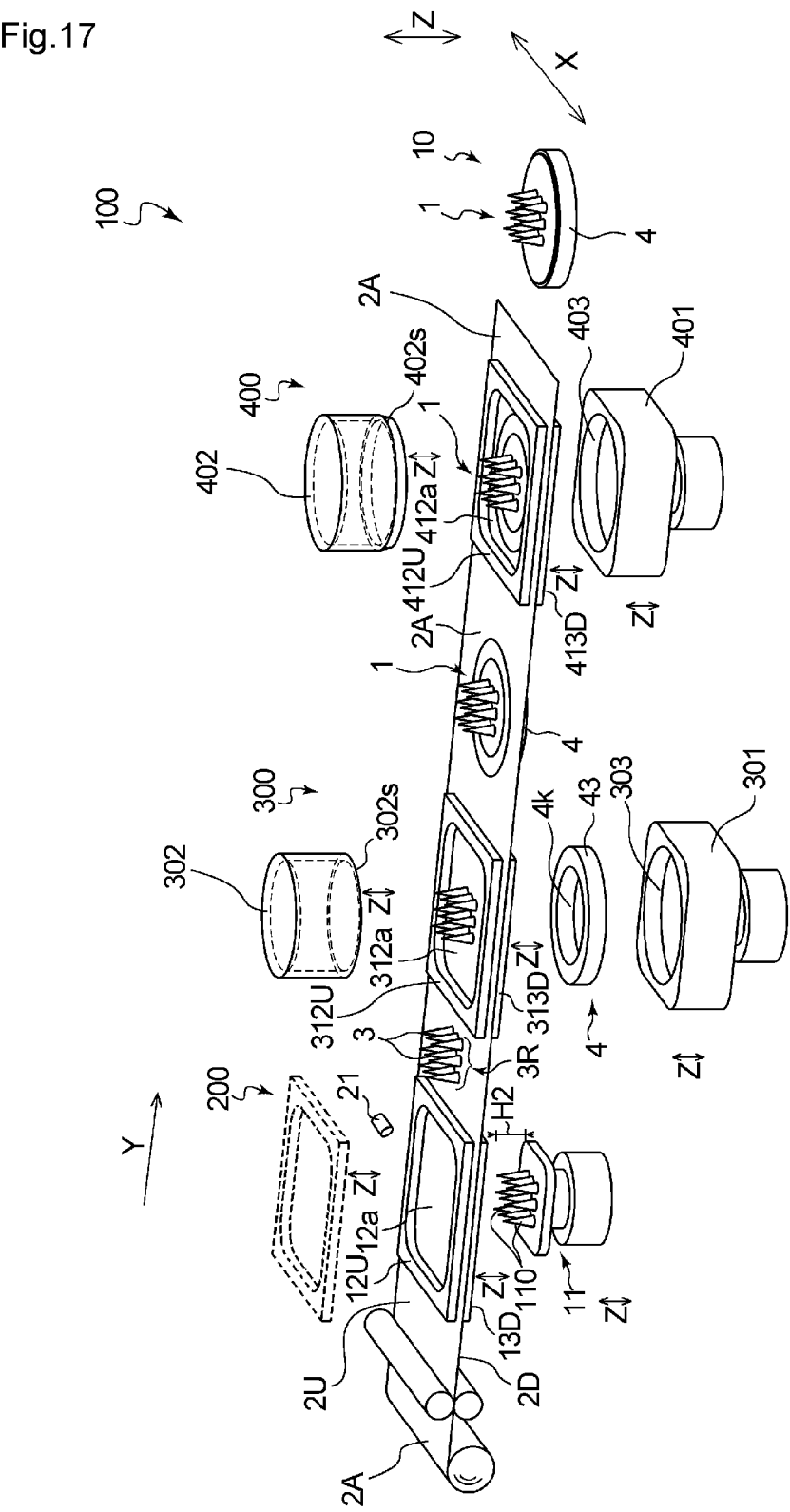
FIG. 17 is a diagram illustrating an overall configuration of a preferred manufacturing device for manufacturing the microprojection unit illustrated in FIG. 11.

The aforementioned microprojection unit 10 can be manufactured, for example, by using a manufacturing device 100 described below. FIG. 17 illustrates an overall configuration of a manufacturing device 100 used for implementing the method for manufacturing the microprojection unit 10. A method for manufacturing the microprojection unit 10 by using the manufacturing device 100 is described below with reference to FIGS. 17 to 21. It should be noted that the protrusions 3 of the microprojection unit 10 are actually very small as described above, but for the sake of explanation, the protrusions 3 are illustrated very large in the figures.

In the following description, the direction in which the base sheet 2A is transported (the longitudinal direction of the base sheet 2A) is referred to as the Y direction, the direction orthogonal to the transporting direction, which is the width direction of the base sheet 2A being transported, is referred to as the X direction, and the thickness direction of the base sheet 2A being transported is referred to as the Z direction.

The method for manufacturing a microprojection unit 10 involves: a microprojection tool forming step of forming a microprojection tool 1 by bringing a projecting mold part 11 into contact from one surface 2D side of a base sheet 2A including a thermoplastic resin, and thus forming protrusions 3 that protrude from another surface 2U side of the base sheet 2A, and withdrawing the projecting mold part 11 from the interior of the protrusions 3; a joining step of joining the one surface 2D side of the base sheet 2A, in which the microprojection tool 1 has been formed, and a tip end of a base component 4; and a cutting step of cutting the base sheet 2A, to which the base component 4 has been joined, at a position more inward than the base component 4's contour 4L in a planar view of the base sheet 2A as viewed from the microprojection tool 1 side, to manufacture a microprojection unit 10.

As illustrated in FIG. 17, the manufacturing device 100 includes, from the upstream side toward the downstream side in the transporting direction (corresponding to the Y direction): a microprojection tool forming section 200 that forms a microprojection tool 1; a member joining section 300 that joins a base component 4 and a base sheet 2A in which the microprojection tool 1 has been formed; and a member cutting section 400 that cuts the base sheet 2A to thereby manufacture a microprojection unit 10. In the manufacturing device 100, the microprojection tool forming section 200 includes, as illustrated in FIG. 18: a protrusion forming section 210 for forming protrusions 3 in the base sheet 2A; a cooling section 220; and a release section 230 where the projecting mold part 11 is withdrawn.

In the present Specification, the projecting mold part 11 is a member including projecting molds 110 which are sections inserted into the base sheet 2A, and in the present embodiment, the projecting mold part 11 is structured so as to be arranged on a disk-shaped foundation. The projecting mold part's structure, however, is not limited thereto, and the projecting mold part may consist only of the projecting mold 110, or the projecting mold part 11 may include a plurality of projecting molds 110 arranged on a platform-like support.

Figure 18:
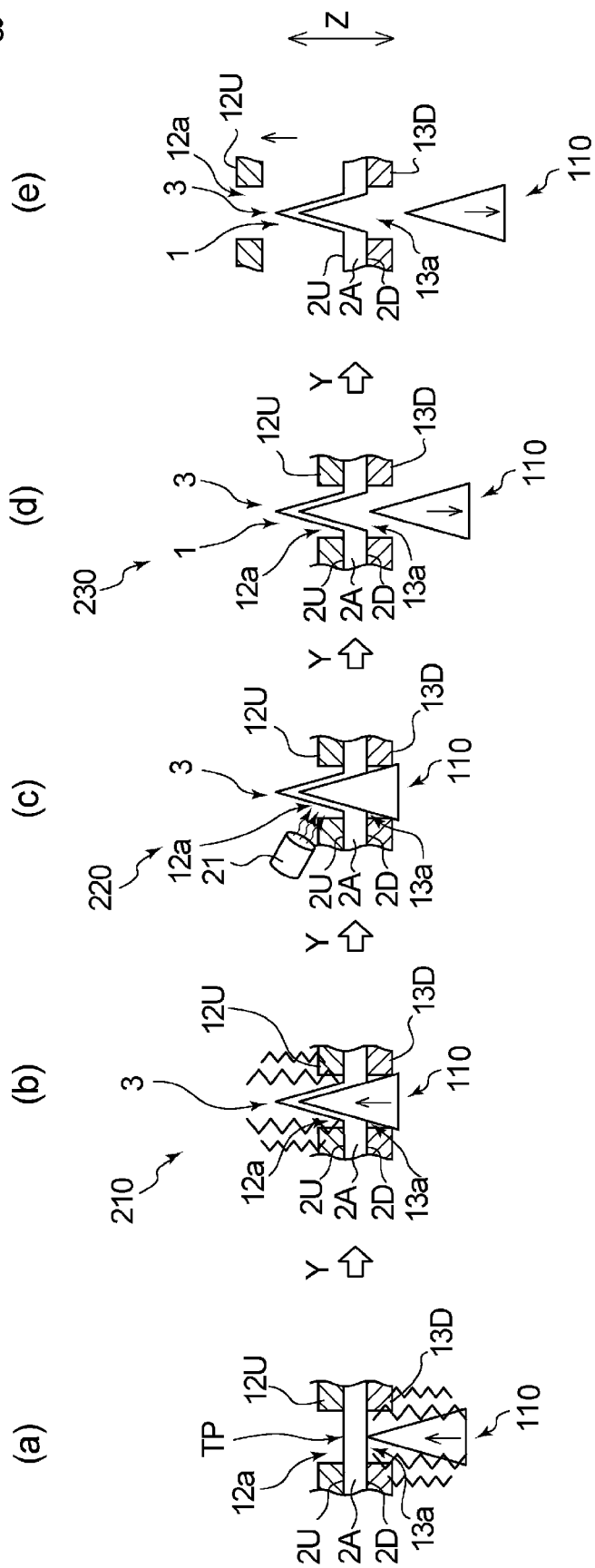
FIGS. 18(a) to 18(e) are diagrams illustrating steps for manufacturing a microprojection tool by employing the manufacturing device illustrated in FIG. 17.

The protrusion forming section 210 is described using FIGS. 17 and 18. As illustrated in FIGS. 17 and 18, the protrusion forming section 210 includes a projecting mold part 11 including a heating means (not illustrated). In the manufacturing device 100, a heating means may be provided to the projecting mold part 11. Further, in the manufacturing device 100, there may be no other heating means except for the heating means of the projecting mold part 11. It should be noted that, in this Specification, "there is no other heating means except for the heating means of the projecting mold part 11" not only refers to cases where other heating means are completely eliminated, but also refers to cases where a means for heating to a temperature below the softening temperature of the base sheet 2A, or to a temperature below the glass transition temperature, is provided. Note, however, that it is preferable to completely eliminate all other heating means. In the manufacturing device 100, the heating means of the projecting mold part 11 is an ultrasonic vibration device.

In the method for manufacturing the microprojection unit 10 by using the manufacturing device 100, first, as illustrated in FIG. 17, a continuous base sheet 2A is paid out from a material roll of the base sheet 2A formed including a thermoplastic resin, and is transported in the transporting direction. Then, when the base sheet 2A has been fed to a predetermined position, the transportation of the base sheet 2A is stopped. In this way, in the method for manufacturing the microprojection unit 10, the continuous base sheet 2A is transported intermittently.

The base sheet 2A is a sheet that constitutes the base 2 of the microprojection tool 1 being manufactured, and is formed by including a thermoplastic resin. Examples of the thermoplastic resin include poly-fatty acid esters, polycarbonate, polypropylene, polyethylene, polyester, polyamide, polyamide imide, polyether ether ketone, polyetherimide, polystyrene, polyethylene terephthalate, polyvinyl chloride, nylon resin, acrylic resin, and combinations thereof. From the viewpoint of biodegradability, poly-fatty acid esters are preferably used. Concrete examples of poly-fatty acid esters include polylactic acid, polyglycolic acid, and combinations thereof. Note that the base sheet 2A may be formed of a mixture including, for example, hyaluronic acid, collagen, starch, cellulose, etc., in addition to thermoplastic resin. The thickness of the base sheet 2A is substantially the same as the thickness T2 of the base 2 of the microprojection tool 1 being manufactured.

Next, in the microprojection tool forming step of the method for manufacturing the microprojection unit 10, as illustrated in FIGS. 18(a) and 18(b), the projecting mold part 11 is brought into contact from the one surface 2D side of the continuous base sheet 2A being transported in the transporting direction, and, while softening, with heat, a contact section TP in the base sheet 2A where the projecting mold part contacts the base sheet, the projecting mold part 11 is inserted into the base sheet 2A, to form protrusions 3 that protrude from the other surface 2U side of the base sheet 2A (protrusion forming step). In the protrusion forming section 210, an opening plate 12U, as a warp-suppressing means, is arranged on the other surface 2U side (upper surface side) of the base sheet 2A, and a second opening plate 13D, as a warp-suppressing means, is arranged on the one surface 2D side (lower surface side) of the base sheet 2A.

The projecting mold part 11 is shaped so as to have a circular-conic section with a sharp tip end, to correspond to the outer shape of the circular-conic protrusion 3 of the microprojection tool 1 being manufactured. More specifically, in the manufacturing device 100, as illustrated in FIG.

17, the projecting mold part 11 includes projecting molds 110 corresponding to the number and arrangement of the protrusions 3 on the microprojection tool 1 to be manufactured and corresponding substantially to the outer shape of each protrusion 3; and twenty-five circular-conic projecting molds 110 are provided corresponding to the twenty-five truncated circular-conic protrusions 3. In this way, by using the projecting mold part 11 having a plurality of projecting molds 110, a plurality of protrusions 3 arranged on the upper surface of the sheet-like base 2 are formed. In the manufacturing device 100, the projecting mold part 11 is arranged such that the respective tip ends of the projecting molds 110 face upward, and is movable at least vertically in the thickness direction. Preferably, in the manufacturing device 100, the projecting mold part 11 can be moved vertically in the thickness direction by an electric actuator (not illustrated). Note that it is preferable that the heating means of the projecting mold part 11 is operated from immediately before the projecting mold part 11 comes into contact with the base sheet 2A to immediately before the base sheet reaches the following cooling step.

The operation of the projecting mold part 11 and heating conditions of the heating means of the projecting mold part 11, such as the activation etc. of the heating means of the projecting mold part 11, are controlled by a control means (not illustrated) provided to the manufacturing device 100.

As described above, in the manufacturing device 100, the heating means of the projecting mold part 11 is an ultrasonic vibration device. As regards the ultrasonic vibration of the projecting mold part 11 by the ultrasonic vibration device, from the viewpoint of forming the protrusions 3, the frequency thereof is preferably from 10 to 50 kHz, more preferably from 15 to 40 kHz. Further, from the viewpoint of forming the protrusions 3, the amplitude of the ultrasonic vibration of the projecting mold part 11 by the ultrasonic vibration device is preferably from 1 to 60 μm, more preferably from 5 to 50 μm.

The shape of the projecting mold part 11 on the tip-end side only needs to be shaped so as to correspond to the outer shape of the protrusion 3 of the microprojection tool 1 being manufactured. The height H2 (cf. FIG. 17) of the projecting mold 110 of the projecting mold part 11 is formed equal to or slightly higher than the height H1 of the protrusion 3 of the microprojection tool 1 being manufactured, and is preferably from 0.01 to 30 mm, more preferably from 0.02 to 20 mm. The tip end diameter D1 (cf. FIG. 19) of the projecting mold 110 of the projecting mold part 11 is preferably from 0.001 to 1 mm, more preferably from 0.005 to 0.5 mm. The tip end diameter D1 of the projecting mold 110 of the projecting mold part 11 is measured as described below.

The base diameter D2 of the projecting mold 110 of the projecting mold part 11 is preferably from 0.1 to 5 mm, more preferably from 0.2 to 3 mm. From the viewpoint of easily achieving sufficient strength, the tip end angle α of the projecting mold 110 of the projecting mold part 11 is preferably from 1 to 60 degrees, more preferably from 5 to 45 degrees. The tip end angle α of the projecting mold part 11 is measured as follows.

{Measurement of Tip End Diameter of Projecting Mold 110 of Projecting Mold Part 11}

Figure 19:
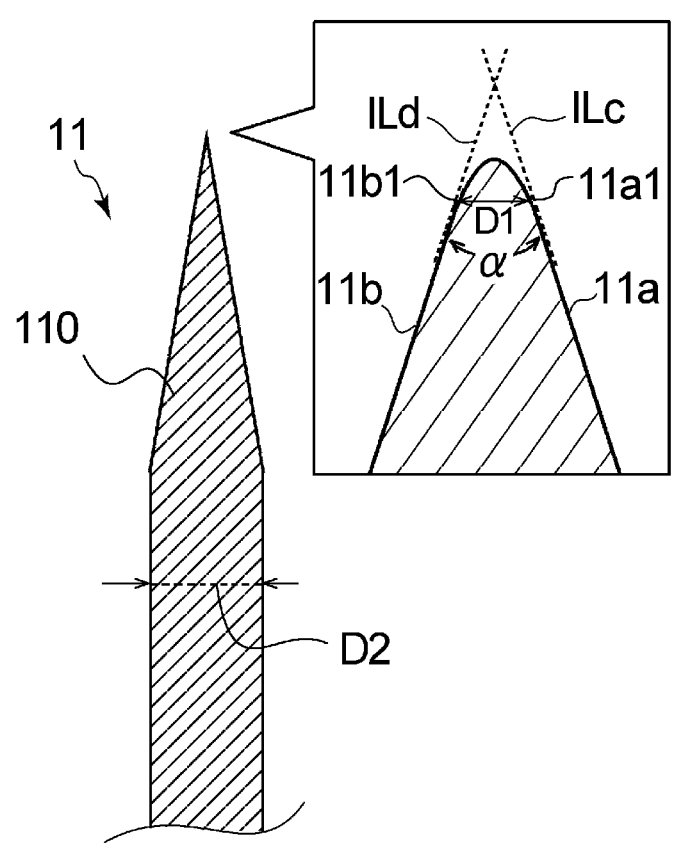
FIG. 19 is an explanatory diagram illustrating a method for measuring the tip end angle of a projecting mold part.

The tip end portion of the projecting mold 110 of the projecting mold part 11 is observed in an enlarged state under a predetermined magnification using a scanning electron microscope (SEM) or a microscope. Next, as illustrated in FIG. 19, an imaginary straight line 1Lc is extended along the straight-line portion of one lateral side 11a of the two lateral sides 11a, 11b. Also, an imaginary straight line 1Ld is extended along the straight-line portion of the other lateral side 11b. The point where the lateral side 11a separates from the imaginary straight line 1Lc on the tip end side is defined as a first tip end point 11a1, and the point where the other lateral side 11b separates from the imaginary straight line 1Ld is defined as a second tip end point 11b1. The length D1 of a straight line that connects the first tip end point 11a1 and the second tip end point 11b1 defined as above is measured using a scanning electron microscope (SEM) or a microscope, and the measured length of the straight line is defined as the tip end diameter of the projecting mold 110.

{Measurement of Tip End Angle α of Projecting Mold 110 of Projecting Mold Part 11}

The tip end portion of the projecting mold 110 of the projecting mold part 11 is observed in an enlarged state under a predetermined magnification using a scanning electron microscope (SEM) or a microscope, as in the SEM image illustrated in FIG. 19, for example. Next, as illustrated in FIG. 19, an imaginary straight line 1Lc is extended along the straight-line portion of one lateral side 11a of the two lateral sides 11a, 11b. Also, an imaginary straight line 1Ld is extended along the straight-line portion of the other lateral side 11b. The angle formed between the imaginary straight line 1Lc and the imaginary straight line 1Ld is measured using a scanning electron microscope (SEM) or a microscope, and the measured angle is defined as the tip end angle α of the projecting mold 110 of the projecting mold part 11.

The projecting mold part 11 is formed of a high-strength material that is hard to bend/break. Examples of materials for the projecting mold part 11 include metals, such as steel, stainless steel, aluminum, aluminum alloy, nickel, nickel alloy, cobalt, cobalt alloy, copper, copper alloy, beryllium copper, and beryllium copper alloy, and ceramics.

As described above, the opening plate 12U used in the protrusion forming step is arranged on the other surface 2U side of the base sheet 2A as illustrated in FIGS. 17 and 18, and serves to make the base sheet 2A less likely to warp/bend when the projecting mold part 11 is inserted from the one surface 2D side. Thus, the opening plate 12U is arranged so as to support a region other than a region, in the base sheet 2A, into which the projecting mold part 11 is inserted—i.e., a region other than the protrusion region 3R, which is a region, in the base sheet 2A, where the protrusions 3 are formed. In the manufacturing device 100, the opening plate 12U arranged as described above is a board-like opening plate having an opening 12a opened so as to surround the protrusion region 3R. The opening plate 12U supports the base sheet 2A in regions other than the opening 12a.

In the manufacturing device 100, as illustrated in FIG. 17, a single opening 12a is formed in the opening plate 12U, and the opening area of the single opening 12a is formed so as to be greater than the total cross-sectional area of the projecting molds 110 so that a plurality of projecting molds 110 of the projecting mold part 11 can be passed through the single opening. Note that a plurality of openings 12a may be formed in the opening plate 12U so as to correspond to the respective projecting molds 110 such that the plurality of projecting molds 110 are passed therethrough respectively.

The opening plate 12U is movable in a direction separating from the direction contacting the base sheet 2A. In the manufacturing device 100, the opening plate 12U can move vertically in the thickness direction by an electric actuator.

The operation of the opening plate 12U is controlled by a control means provided to the manufacturing device 100.

The material constituting the opening plate 12U may be the same as the material of the projecting mold part 11, and may be formed of a synthetic resin, for example.

The manufacturing device 100 includes an ultrasonic vibration device as a heating means of the projecting mold part 11. In the method for manufacturing the microprojection unit 10, the protrusion forming step is performed in a state where the base sheet 2A is sandwiched between the opening plate 12U and the second opening plate 13D. In the protrusion forming step using the manufacturing device 100, the projecting mold part 11 is passed through an opening 13a in the later-described second opening plate 13D from the one surface 2D side (lower surface side) of the base sheet 2A, and, while causing ultrasonic vibration in the projecting mold part 11 in advance by the ultrasonic vibration device, the projecting mold part 11 is made to contact the one surface 2D of the base sheet 2A, as illustrated in FIG. 18(a). Thus, the contact sections TP are softened. Then, as illustrated in FIG. 18(b), while softening the contact sections TP, the projecting mold part 11 is raised from the one surface 2D side (lower surface side) of the base sheet 2A toward the other surface 2U side (upper surface side), and the projecting mold part 11 is inserted into the base sheet 2A, while suppressing warping of the base sheet 2A with the opening plate 12U arranged on the other surface 2U side (upper surface side) of the base sheet 2A, thereby forming protrusions 3 that protrude from the other surface 2U side (upper surface side) of the base sheet 2A.

From the viewpoint of forming the protrusions 3, the heating temperature of the base sheet 2A by heating the projecting mold part 11 is preferably equal to or higher than the glass transition temperature of the base sheet 2A being used to below the melting temperature thereof, and more preferably, equal to or higher than the softening temperature of the base sheet 2A to below the melting temperature thereof. More specifically, the heating temperature is preferably from 30° C. to 300° C., more preferably from 40° C. to 250° C. In cases where the base sheet 2A is heated by using an ultrasonic vibration device, the aforementioned heating temperature range is employed as the temperature range of a section of the base sheet 2A that comes into contact with the projecting mold 110. On the other hand, in cases where the base sheet 2A is heated by using a heating heater device instead of the ultrasonic vibration device, the heating temperature of the projecting mold part 11 simply needs to be adjusted within the aforementioned range. It should be noted that the glass transition temperature (Tg) is measured according to the following measurement method, and the softening temperature is measured according to JIS K-7196 "Testing method for softening temperature of thermoplastic film and sheeting by thermomechanical analysis".

{Method for Measuring Glass Transition Temperature (Tg)}

The glass transition temperature is determined by measuring the heat quantity by using a DSC measurement device. More specifically, the measurement device used is a differential scanning calorimeter (Diamond DSC) from Perkin Elmer. A 10-mg test piece is sampled from the base sheet. As for the measurement conditions, the temperature is maintained at 20° C. for 5 minutes, and then the temperature is raised from 20° C. to 320° C. at a rate of 5° C./minute, to obtain a DSC curve wherein the horizontal axis indicates temperature and the vertical axis indicates heat quantity. The glass transition temperature Tg is determined from the DSC curve.

Note that the "glass transition temperature (Tg) of base sheet" refers to the glass transition temperature (Tg) of the resin constituting the base sheet. In cases where there are a plurality of types of constituent resins and the plurality of glass transition temperatures (Tg) are different from each other, the heating temperature of the base sheet by the heating means is preferably at least equal to or higher than the lowest glass transition temperature (Tg) among the plurality of glass transition temperatures (Tg), and more preferably equal to or higher than the highest glass transition temperature (Tg) among the plurality of glass transition temperatures (Tg).

The same applies to the "softening temperature of the base sheet", as with the glass transition temperature (Tg). In cases where there are a plurality of types of constituent resins in the base sheet and the plurality of softening temperatures are different from each other, the heating temperature of the base sheet by the heating means is preferably at least equal to or higher than the lowest softening temperature among the plurality of softening temperatures, and more preferably equal to or higher than the highest softening temperature among the plurality of softening temperatures.

In cases where the base sheet includes two or more types of resins having different melting points, the heating temperature of the base sheet by the heating means is preferably below the lowest melting point among the plurality of melting points.

If the insertion speed for inserting the projecting mold part 11 into the base sheet 2A is too slow, the resin will get heated and softened excessively, whereas if the insertion speed is too fast, heating and softening will be insufficient. Thus, from the viewpoint of forming the protrusions 3 efficiently, the insertion speed is preferably from 0.1 to 1000 mm/second, more preferably from 1 to 800 mm/second. The softening time is the time from when the elevation of the heated-state projecting mold part 11 is stopped until the following cooling step is performed while keeping the projecting mold part 11 inserted in the interior of the protrusion 3. Although a too-long softening time will result in excessive heating, from the viewpoint of supplementing insufficient heating, the softening time is preferably from 0 to 10 seconds, more preferably from 0.1 to 5 seconds.

From the viewpoint of forming the protrusions 3 efficiently, the insertion height of the projecting mold part 11 inserted into the base sheet 2A is preferably from 0.01 to 10 mm, more preferably from 0.02 to 5 mm. Herein, "insertion height" refers to the distance between the apex of the projecting mold part 11 and the other surface 2U (upper surface) of the base sheet 2A in a state where the projecting mold part 11 is inserted furthest in the base sheet 2A. So, the insertion height in the protrusion forming step refers to the distance measured in the perpendicular direction from the other surface 2U to the apex of the projecting mold part 11 in a state where the projecting mold part 11 has been inserted furthest in the protrusion forming step and the projecting mold part 11 has emerged from the other surface 2U of the base sheet 2A.

The microprojection tool 1 has an opening 3h in the vicinity of the tip end of the protrusion 3. Thus, the opening 3h is formed by inserting the projecting mold part 11 into the base sheet 2A until it penetrates the base sheet by controlling the operations of the projecting mold part 11 and/or the heating conditions etc. of the heating means of the projecting mold part 11 in the protrusion forming step.

Next, in the manufacturing device 100, as illustrated in FIG. 18(c), a cooling section 220 is provided subsequent to the protrusion forming section 210. The cooling section 220 includes, for example, a cold air blowing device (not illustrated). In the microprojection tool forming step of the method for manufacturing the microprojection unit 10, after the protrusion forming step using the manufacturing device 100, the protrusions 3 are cooled by using this cold air blowing device in a state where the projecting mold part 11 is inserted in the interior of the protrusions 3 (cooling step). More specifically, in the manufacturing device 100, the opening plate 12U is arranged on the other surface 2U side (upper surface side) of the base sheet 2A and the later-described second opening plate 13D is arranged on the one surface 2D side (lower surface side) of the base sheet 2A. Thus, in the method for manufacturing the microprojection unit 10, the cooling step is performed in a state where the base sheet 2A is sandwiched between the opening plate 12U and the second opening plate 13D. In the cold air blowing device of the manufacturing device 100, as illustrated in FIG. 14, an air vent 21 for blowing cold air is provided on the other surface 2U side (upper surface side) of the base sheet 2A, and cooling is performed by blowing cold air from the air vent 21 in a state where the projecting mold part 11 is kept inserted in the interior of the protrusions 3. Note that, during cooling, heating of the projecting mold part 11 with the heating device may be continued or stopped, but it is preferable that heating is stopped.

From the viewpoint of forming the protrusions 3, the temperature of the cold air to be blown is preferably from −50° C. to 26° C., more preferably from −40° C. to 10° C. From the viewpoint of balancing moldability and processing time, the cooling time for cooling by blowing cold air is preferably from 0.01 to 60 seconds, more preferably from 0.5 to 30 seconds.

In cases where the heating means of the projecting mold part 11 is ultrasonic vibration as in the manufacturing device 100, the cold air blowing device does not necessarily have to be provided, and cooling can be achieved by simply turning off the vibration of the ultrasonic vibration device. From this viewpoint, using ultrasonic vibration as the heating means is preferable in terms that the device can be simplified and microprojection tools 1 can be manufactured easily at high speed. Further, heat is less likely to be transmitted to sections of the base sheet 2A that are not in contact with the projecting mold part 11 and cooling is performed efficiently by stopping the application of ultrasonic vibration; this is advantageous in that deformation is less likely to occur in sections other than the section being molded.

Next, in the manufacturing device 100, as illustrated in FIG. 18(d), a release section 230 is provided subsequent to the cooling section 220. In the microprojection tool forming step of the method for manufacturing the microprojection unit 10, the projecting mold part 11 is withdrawn from the interior of the protrusions 3 after the cooling step, to form a microprojection tool 1 (release step). In the release step, the second opening plate 13D, which serves as a warp-suppressing means that suppresses warping of the base sheet 2A, is used when the projecting mold part 11 is withdrawn from the interior of the protrusions 3, to thereby form the microprojection tool 1. In the manufacturing device 100, the second opening plate 13D used in the release step is arranged on the one surface 2D side of the base sheet 2A, and is arranged at a position corresponding to the predetermined position to which the base sheet 2A is fed.

The second opening plate 13D used in the release step is arranged on the one surface 2D side of the base sheet 2A as illustrated in FIGS. 17 and 18, and serves to make the base sheet 2A less likely to warp/bend when the projecting mold part 11 is withdrawn from the one surface 2D side. Thus, the second opening plate 13D is arranged so as to support a region other than a region, in the base sheet 2A, from which the projecting mold part 11 is withdrawn—i.e., a region other than the protrusion region 3R, which is a region, in the base sheet 2A, where the protrusions 3 are formed. In the manufacturing device 100, the second opening plate 13D arranged as described above is a board-like second opening plate having an opening 13a opened so as to surround the protrusion region 3R. The second opening plate 13D supports the base sheet 2A in regions other than the opening 13a.

In the manufacturing device 100, as illustrated in FIG. 18, a single opening 13a is formed in the second opening plate 13D, and the opening area of the single opening 13a is formed so as to be greater than the total cross-sectional area of the projecting molds 110 so that a plurality of projecting molds 110 of the projecting mold part 11 can be passed through the single opening. Note that a plurality of openings 13a may be formed in the second opening plate 13D so as to correspond to the respective projecting molds 110 such that the plurality of projecting molds 110 are passed therethrough respectively. In the manufacturing device 100, the opening 13a of the second opening plate 13D is arranged concentrically with the opening 12a of the opening plate 12U. Thus, the openings 12a, 13a of the pair of the opening plate 12U and the second opening plate 13D sandwiching the base sheet 2A overlap one another in the thickness direction.

In the manufacturing device 100, the opening 12a of the opening plate 12U and the opening 13a of the second opening plate 13D have the same opening shape. Note that the shape of the openings 12a, 13a as viewed from the upper surface side of the opening plates 12U, 13D is not particularly limited; in the manufacturing device 100, the openings are both circular, and the opening diameter of the openings 12a, 13a is the same.

The second opening plate 13D may be fixed, but in the manufacturing device 100, the second opening plate is movable in a direction separating from the direction contacting the base sheet 2A. The second opening plate 13D is made movable vertically in the thickness direction by an electric actuator (not illustrated).

The operation of the second opening plate 13D is controlled by a control means (not illustrated) provided to the manufacturing device 100.

The material constituting the second opening plate 13D may be the same as the material constituting the opening plate 12U or the material of the projecting mold part 11, and may be formed of a synthetic resin, for example.

In the manufacturing device 100, the opening plate 12U is arranged on the other surface 2U side (upper surface side) of the base sheet 2A, and the second opening plate 13D is arranged on the one surface 2D side (lower surface side) of the base sheet 2A. Thus, the release step is performed in a state where the base sheet 2A is sandwiched between the opening plate 12U and the second opening plate 13D. In the method for manufacturing the microprojection unit 10, as illustrated in FIG. 18(e), after performing the release step in a state where the base sheet 2A is sandwiched between the opening plate 12U and the second opening plate 13D, the second opening plate 13D is moved downward and the opening plate 12U is moved upward, and thereby, a microprojection tool 1 having protrusions 3 with a hollow interior is formed in the base sheet 2A (microprojection tool forming step).

Figure 20:
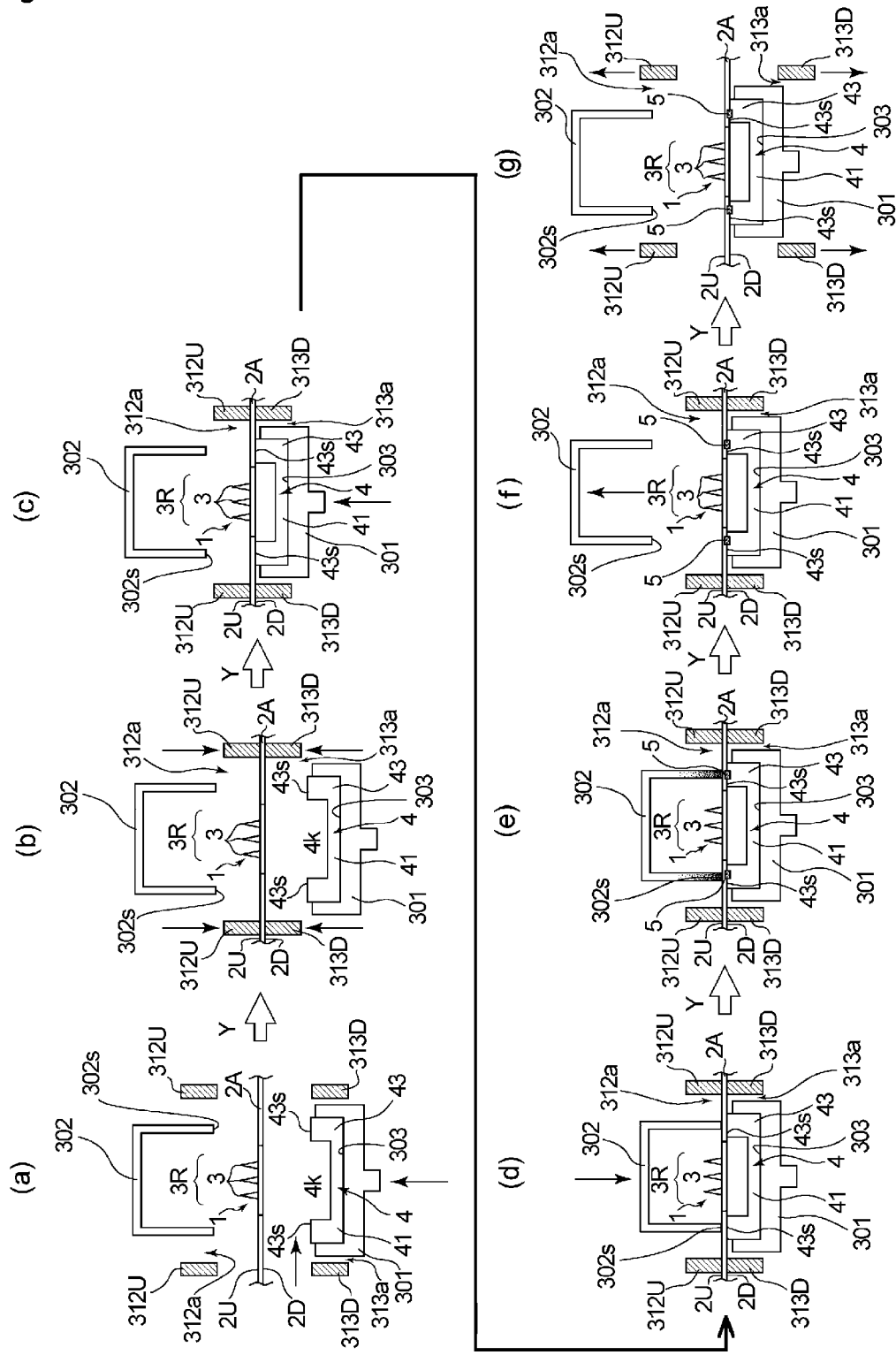
FIGS. 20(a) to 20(g) are diagrams illustrating a joining step for forming a joined region by employing the manufacturing device illustrated in FIG. 17.

Next, as illustrated in FIG. 17, the base sheet 2A, in which the microprojection tool 1 having the protrusions 3 has been formed, is moved in the transporting direction (Y direction). In the step following the microprojection tool forming step, as illustrated in FIGS. 17 and 20, the one surface 2D side (lower surface side) of the base sheet 2A—in which the microprojection tool 1, manufactured in the microprojection tool forming step, has been formed—and the tip end of the base component 4 are joined together (joining step). Herein, the "tip end of the base component 4" refers to a section of the base component 4 located closest to the one surface 2D side (lower surface side) of the base sheet 2A; in the microprojection unit 10, it refers to the tip-end wall portion 43s which is the tip end of the peripheral wall portion 43 arranged so as to extend over the outer periphery of the liquid retention space 4k of the base component 4. The joining step is performed by using the manufacturing device 100's member joining section 300 for joining the base sheet 2A, in which the microprojection tool 1 has been formed, and the base component 4.

In cases of forming the joined region 5 by fusion-bonding, it is preferable that the base component 4 is formed including the same type of thermoplastic resin as the base sheet 2A, from the viewpoint of facilitating formation of the joined region 5. Examples of the thermoplastic resin include poly-fatty acid esters, polycarbonate, polypropylene, polyethylene, polyester, polyamide, polyamide imide, polyether ether ketone, polyetherimide, polystyrene, polyethylene terephthalate, polyvinyl chloride, nylon resin, acrylic resin, and combinations thereof. From the viewpoint of biodegradability, poly-fatty acid esters are preferably used. Concrete examples of poly-fatty acid esters include polylactic acid, polyglycolic acid, and combinations thereof. Note that, in cases where the joined region 5 is to be formed by using an adhesive, the base component 4 may be made of a material different from the base sheet 2A, and may be made of metal, for example.

In the manufacturing device 100, as illustrated in FIGS. 17 and 20, the member joining section 300 includes: a base component fixing part 301 that fixes the base component 4; a joining section 302 that joins the base sheet 2A, in which the microprojection tool 1 has been formed, and the base component 4; and an upper opening plate 312U and a lower opening plate 313D that sandwich the base sheet 2A, in which the microprojection tool 1 having the protrusions 3 has been formed. The base component fixing part 301 has a depression 303 having a shape corresponding to the outer shape of the entire base component 4. In the microprojection unit 10, the depression 303 is formed in a shape that fits with a cylindrical shape having a circular bottom portion 41.

As illustrated in FIG. 17, the base component fixing part 301, having the depression 303, is arranged on the one surface 2D (lower surface) side of the base sheet 2A, and holds the base component 4's bottom portion 41 side in a manner that the outer shape of the base component 4's bottom portion 41 side is fitted in the depression 303 and the tip-end wall portion 43s of the base component 4's peripheral wall portion 43 is exposed. The base component fixing part 301 may be fixed, but in this manufacturing device 100, the base component fixing part is movable in a direction separating from the direction contacting the base sheet 2A. More specifically, the base component fixing part 301 is made movable vertically in the thickness direction by an electric actuator (not illustrated).

The operation of the base component fixing part 301 is controlled by a control means (not illustrated) provided to the manufacturing device 100.

The base component fixing part 301 may be made of the same material as that of the projecting mold part 11, and may be made, for example, of a synthetic resin.

The joining section 302 is a section that joins the base sheet 2A, in which the microprojection tool 1 has been formed, and the base component 4. As illustrated in FIGS. 17 and 20, the joining section 302 annularly surrounds the protrusion region 3R, which is a region, in the base sheet 2A, where the protrusions 3 are formed, and has an annular ring-shaped tip-end portion 302s corresponding to the peripheral wall portion 43 of the base component 4. The joining section 302 having the tip-end portion 302s is formed in a tubular shape with the tip-end portion 302s side opened. Preferably, the width of the tip-end portion 302s of the joining section 302 is narrower than the width of the tip-end wall portion 43s of the peripheral wall portion 43 of the base component 4, and substantially matches the width W2 of the continuous joined region 5.

As illustrated in FIGS. 17 and 20, the joining section 302 is arranged on the other surface 2U (upper surface) side of the base sheet 2A. In the manufacturing device 100, the joining section 302 is movable in a direction separating from the direction contacting the base sheet 2A. More specifically, the joining section 302 is made movable vertically in the thickness direction by an electric actuator (not illustrated).

The operation of the joining section 302 is controlled by a control means (not illustrated) provided to the manufacturing device 100.

Examples of means for performing joining in the joining step include heat sealing, ultrasound, a laser, an adhesive, or the like. In the manufacturing device 100, the joining means in the joining section 302 is a joining means by heat sealing. Note that heat sealing, ultrasound, and laser are joining means that perform joining by employing fusion-bonding, i.e., a phenomenon in which the materials of the base sheet 2A and the base component 4 are molten and bonded by heat. For the adhesive, it is possible to use, for example, a hot-melt adhesive, which is conventionally used in this type of product.

As illustrated in FIG. 20, the lower opening plate 313D is arranged on the one surface 2D (lower surface) side of the base sheet 2A, and is formed of a board-like plate having a single opening 313a. The opening area of the opening 313a is formed greater than the planar area of the base component fixing part 301 so that the base component fixing part 301 can be passed therethrough when the base component fixing part 301 is moved upward in the thickness direction from the one surface 2D side.

As illustrated in FIG. 20, the upper opening plate 312U is arranged on the other surface 2U (upper surface) side of the base sheet 2A, and is formed of a board-like plate having a single opening 312a. The opening area of the opening 312a is formed greater than the planar area of the joining section 302 so that the joining section 302 can be passed therethrough when the joining section 302 is moved downward in the thickness direction from the other surface 2U side.

The lower opening plate 313D and the upper opening plate 312U are movable in a direction separating from the direction contacting the base sheet 2A. In the manufacturing device 100, the lower opening plate 313D and the upper opening plate 312U are made movable vertically in the thickness direction by an electric actuator (not illustrated).

The operation of the lower opening plate 313D and the upper opening plate 312U is controlled by a control means (not illustrated) provided to the manufacturing device 100.

In the method for manufacturing the microprojection unit 10, the base component 4 is held in a manner that the outer shape of the base component 4's bottom portion 41 side is fitted in the depression 303 of the base component fixing part 301 and the tip-end wall portion 43s of the base component 4's peripheral wall portion 43 is exposed, as illustrated in FIG. 20(a).

Next, in the method for manufacturing the microprojection unit 10, as illustrated in FIG. 20(b), the lower opening plate 313D is moved upward and the upper opening plate 312U is moved downward, and the base sheet 2A, in which the microprojection tool 1 has been formed, is sandwiched between the lower opening plate 313D and the upper opening plate 312U at a position more outward than the protrusion region 3R where the protrusions 3 are formed in the base sheet 2A. In this way, the base sheet 2A, in which the microprojection tool 1 has been formed, is sandwiched between the lower opening plate 313D and the upper opening plate 312U. Then, as illustrated in FIG. 20(c), in a state where the base sheet 2A is sandwiched, the base component fixing part 301 holding the base component 4 is passed through the opening 313a of the lower opening plate 313D from the one surface 2D side (lower surface side) of the base sheet 2A, and the tip-end wall portion 43s of the peripheral wall portion 43 of the base component 4 is brought into contact with the one surface 2D of the base sheet 2A.

Further, as illustrated in FIG. 20(d), in a state where the base sheet 2A, in which the microprojection tool 1 has been formed, is sandwiched between the lower opening plate 313D and the upper opening plate 312U, the joining section 302 is passed through the opening 312a of the upper opening plate 312U from the other surface 2U side (upper surface side) of the base sheet 2A, and the annular ring-shaped tip-end portion 302s of the joining section 302 is brought into contact with the other surface 2U of the base sheet 2A. It should be noted that the base sheet 2A, in which the microprojection tool 1 has been formed, may be sandwiched by the lower opening plate 313D and the upper opening plate 312U after bringing the annular ring-shaped tip-end portion 302s of the joining section 302 into contact with the other surface 2U of the base sheet 2A.

In the method for manufacturing the microprojection unit 10, as illustrated in FIG. 20(e), in a state where the base sheet 2A, in which the microprojection tool 1 has been formed, is sandwiched between the lower opening plate 313D and the upper opening plate 312U, heating is performed at the annular ring-shaped tip-end portion 302s of the joining section 302, and the one surface 2D side (lower surface side) of the base sheet 2A, in which the microprojection tool 1 has been formed, and the tip end of the base component 4 are joined together by forming a joined region 5 in the microprojection unit 10 while causing the base component 4's tip-end wall portion 43s and a portion of the base sheet 2A located on the tip-end wall portion 43s of the base component 4's peripheral wall portion 43 to melt. After forming the joined region 5 in the microprojection unit 10, heating of the joining section 302 is stopped.

The heating temperature when causing the joining section 302 to contact the base sheet 2A is preferably 100° C. or higher, more preferably 120° C. or higher, and preferably 300° C. or lower, more preferably 250° C. or lower, and more specifically, preferably from 100° C. to 300° C., more preferably from 120° C. to 250° C.

The heating time when causing the joining section 302 to contact the base sheet 2A is preferably 0.1 seconds or greater, and preferably 5.0 seconds or less, and more specifically, preferably from 0.1 to 5.0 seconds.

The pressing force (pressurizing force) when causing the joining section 302 to contact the base sheet 2A is preferably 10 N or greater, and preferably 100 N or less, and more specifically, preferably from 10 to 100 N.

After performing the joining step, as illustrated in FIG. 20(f), the joining section 302 is moved upward, in the thickness direction, from the other surface 2U side (upper surface side) of the base sheet 2A. Then, as illustrated in FIG. 20(g), the lower opening plate 313D is moved downward, and the upper opening plate 312U is moved upward. In this way, the base sheet 2A, to which the base component 4 has been joined and in which the microprojection tool 1 has been provided, is formed on the base component fixing part 301.

Next, as illustrated in FIG. 17, the base sheet 2A, in which the microprojection tool 1 having the protrusions 3 has been formed and to which the base component 4 has been joined, is moved in the transporting direction (Y direction). In the step after the joining step, the base sheet 2A manufactured in the joining step, to which the base component 4 has been joined, is cut along the contour 4L of the base component 4 at a position more inward than the base component 4's contour 4L in a planar view of the base sheet 2A as viewed from the microprojection tool 1 side, to manufacture the microprojection unit 10 (cutting step). Herein, "more inward than the base component 4's contour" means, in other words, more inward than the outer periphery of the bottom portion 41 of the base component 4. The cutting step is performed by using the member cutting section 400 for cutting the base sheet 2A and thereby manufacturing the microprojection unit 10.

Figure 21:
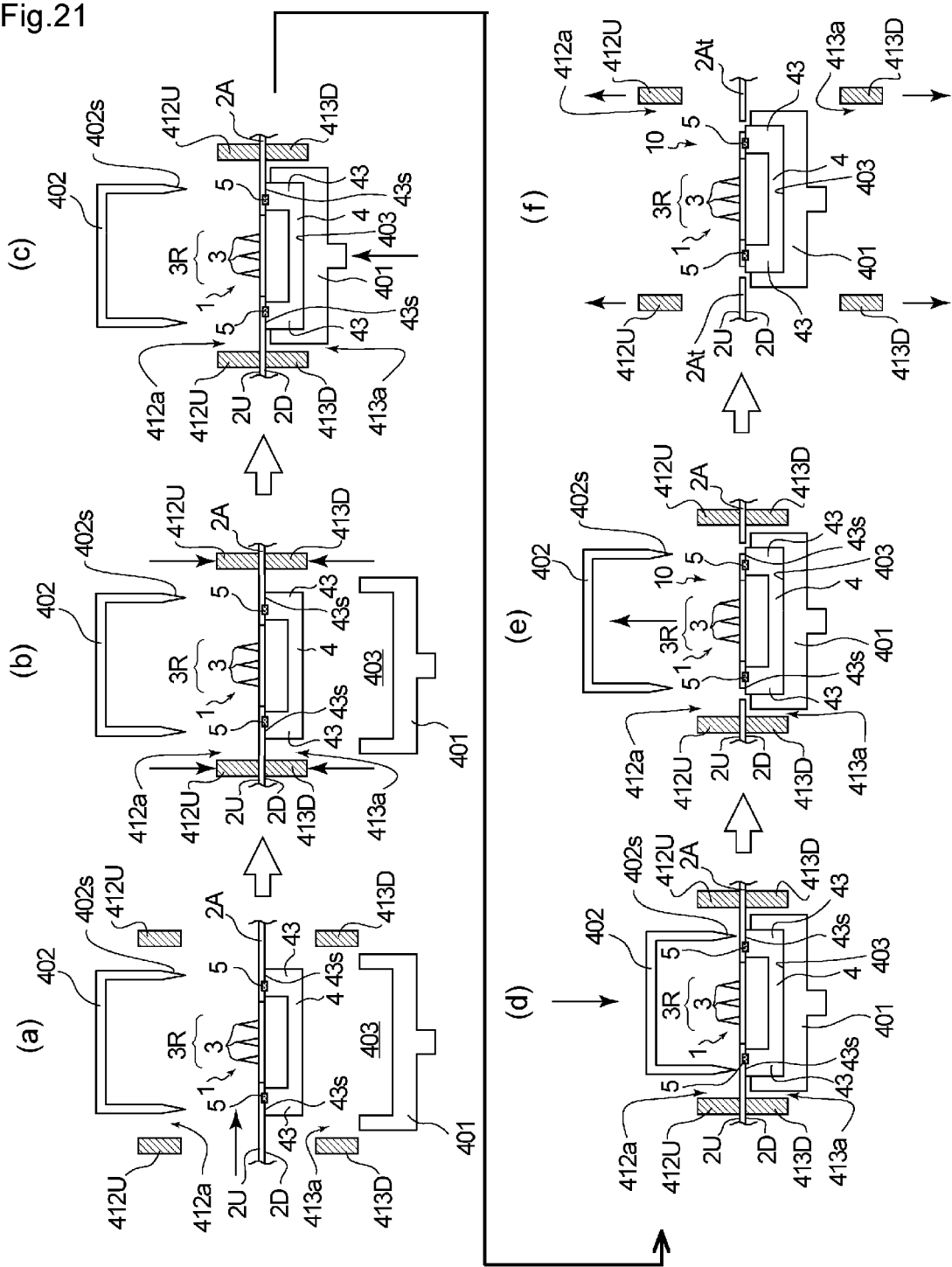
FIGS. 21(a) to 21(f) are diagrams illustrating a cutting step for forming a microprojection unit by performing cutting by employing the manufacturing device illustrated in FIG. 17.

In the manufacturing device 100, as illustrated in FIGS. 17 and 21, the member cutting section 400 includes: a base component fixing part 401 that fixes the base component 4; a cutting section 402 that cuts the base sheet 2A to which the base component 4 has been joined; and an upper opening plate 412U and a lower opening plate 413D that sandwich the base sheet 2A to which the base component 4 has been joined. The base component fixing part 401 has a depression 403 having a shape corresponding to the outer shape of the entire base component 4. In the microprojection unit 10, like the depression 303 of the base component fixing part 301 of the member joining section 300, the depression 403 is formed in a shape that fits with a cylindrical shape having a circular bottom portion 41.

As illustrated in FIGS. 17 and 21, the base component fixing part 401, having the depression 403, is arranged on the one surface 2D (lower surface) side of the base sheet 2A, and holds the base sheet 2A, to which the base component 4 has been joined, in a manner that the outer shape of the base component 4's bottom portion 41 side is fitted in the depression 403. The base component fixing part 401 may be fixed, but in this manufacturing device 100, like the base component fixing part 301 of the member joining section 300, the base component fixing part is movable in a direction separating from the direction contacting the base sheet 2A. More specifically, the base component fixing part 401 is made movable vertically in the thickness direction by an electric actuator (not illustrated).

The operation of the base component fixing part 401 is controlled by a control means (not illustrated) provided to the manufacturing device 100.

Like the base component fixing part 301 of the member joining section 300, the base component fixing part 401 may be made of the same material as that of the projecting mold part 11, and may be made, for example, of a synthetic resin.

The cutting section 402 is a section that cuts the base sheet 2A to which the base component 4 has been joined, and thereby manufactures the microprojection unit 10. As illustrated in FIGS. 17 and 21, the cutting section 402 annularly surrounds the protrusion region 3R, which is a region, in the base sheet 2A, where the protrusions 3 are formed, and has an annular ring-shaped tip-end portion 402s corresponding to the peripheral wall portion 43 of the base component 4. The cutting section 402 having the tip-end portion 402s is formed in a tubular shape with the tip-end portion 402s side opened.

As illustrated in FIGS. 17 and 21, the cutting section 402 is arranged on the other surface 2U (upper surface) side of the base sheet 2A. In the manufacturing device 100, the cutting section 402 is movable in a direction separating from the direction contacting the base sheet 2A. More specifically, the cutting section 402 is made movable vertically in the thickness direction by an electric actuator (not illustrated).

The operation of the cutting section 402 is controlled by a control means (not illustrated) provided to the manufacturing device 100.

Examples of means for cutting in the cutting step include means such as a punching blade or a laser. In the manufacturing device 100, the cutting means in the cutting section 402 is a cutting means consisting of a punching blade. Preferably, the blade at the tip-end portion 402s of the cutting section 402 is arranged within the range of the thickness T4 of the tip-end wall portion 43s of the peripheral wall portion 43 of the base component 4. In the manufacturing device 100, the blade at the tip-end portion 402s of the cutting section 402 is arranged at a position on the protrusion region 3R side, i.e., more inward than the contour 4L of the base component 4—i.e., the outer periphery of the bottom portion 41—and more outward than the outer-side peripheral edge of the continuous joined region 5. Note that a laser is a cutting means that, by irradiation with a laser beam, melts and cuts the base sheet 2A at the same time as melting and bonding the materials of the base sheet 2A and the base component 4 by heat as described above.

As illustrated in FIG. 21, like the lower opening plate 313D of the member joining section 300, the lower opening plate 413D is arranged on the one surface 2D (lower surface) side of the base sheet 2A, and is formed of a board-like plate having a single opening 413a. The opening area of the opening 413a is formed greater than the planar area of the base component fixing part 401 so that the base component fixing part 401 can be passed therethrough when the base component fixing part 401 is moved upward in the thickness direction from the one surface 2D side.

As illustrated in FIG. 21, like the upper opening plate 312U of the member joining section 300, the upper opening plate 412U is arranged on the other surface 2U (upper surface) side of the base sheet 2A, and is formed of a board-like plate having a single opening 412a. The opening area of the opening 412a is formed greater than the planar area of the cutting section 402 so that the cutting section 402 can be passed therethrough when the cutting section 402 is moved downward in the thickness direction from the other surface 2U side.

The lower opening plate 413D and the upper opening plate 412U are movable in a direction separating from the direction contacting the base sheet 2A. In the manufacturing device 100, the lower opening plate 413D and the upper opening plate 412U are made movable vertically in the thickness direction by an electric actuator (not illustrated).

The operation of the lower opening plate 413D and the upper opening plate 412U is controlled by a control means (not illustrated) provided to the manufacturing device 100.

In the method for manufacturing the microprojection unit 10, as illustrated in FIGS. 21(a) and 21(b), the lower opening plate 413D is moved upward and the upper opening plate 412U is moved downward, and the base sheet 2A, to which the base component 4 has been joined and in which the microprojection tool 1 has been provided, is sandwiched between the lower opening plate 413D and the upper opening plate 412U at a position, within the base sheet 2A, more outward than the contour 4L of the base component 4. In this way, the base sheet 2A, to which the base component 4 has been joined, is sandwiched between the lower opening plate 413D and the upper opening plate 412U.

Then, in the method for manufacturing the microprojection unit 10, as illustrated in FIG. 21(c), in a state where the base sheet 2A is sandwiched between the lower opening plate 413D and the upper opening plate 412U, the base component fixing part 401 is passed through the opening from the one surface 2D side (lower surface side) of the base sheet 2A. Then, the base sheet 2A, to which the base component 4 has been joined and in which the microprojection tool 1 has been provided, is held by fitting the outer shape on the bottom portion 41 side of the base component 4 within the depression 403 of the base component fixing part 401.

As illustrated in FIG. 21(d), in a state where the base sheet 2A, to which the base component 4 has been joined, is sandwiched between the lower opening plate 413D and the upper opening plate 412U, the cutting section 402 is passed through the opening 412a of the upper opening plate 412U from the other surface 2U side (upper surface side) of the base sheet 2A, and the microprojection unit 10 is manufactured by bringing the blade at the tip-end portion 402s of the cutting section 402 into contact with the other surface 2U of the base sheet 2A to cut the base sheet 2A along the contour 4L of the base component 4 at a position more inward than the base component 4's contour 4L in a planar view from the microprojection tool 1 side. In the cutting step of the method for manufacturing the microprojection unit 10, the microprojection unit 10 is manufactured by cutting the base sheet 2A on the tip-end wall portion 43s of the peripheral wall portion 43, which is arranged around the outer periphery of the liquid retention space 4k of the base component 4.

After performing the cutting step, as illustrated in FIG. 21(e), the cutting section 402 is moved upward, in the thickness direction, from the other surface 2U side (upper surface side) of the base sheet 2A. Then, as illustrated in FIG. 21(f), a trimmed portion 2At of the base sheet 2A sandwiched between the lower opening plate 413D and the upper opening plate 412U is removed after moving the lower opening plate 413D downward and moving the upper opening plate 412U upward. In this way, the microprojection unit 10 is formed on the base component fixing part 401.

The microprojection unit 10 formed as above is then removed from the base component fixing part 401 and transported downstream in the transporting direction (Y direction). By repeating the aforementioned steps, microprojection units 10 can be manufactured continuously and efficiently.

The present invention has been described above according to preferred embodiments thereof, but the invention is not limited to the foregoing embodiments, and can be modified as appropriate.

For example, the aforementioned microprojection unit 10 illustrated in FIGS. 11 to 13 may be microprojection units 10 having shapes as illustrated in FIGS. 22(a) to 22(d) in a planar view from the microprojection tool 1 side. More specifically, in the microprojection unit 10 illustrated in FIG. 22(a), the shape of the contour 4L of the base component 4 is circular, and nine protrusions 3 are arranged on the upper surface of the sheet-like base 2 in three rows in the longitudinal direction Y and three rows in the lateral direction X. The microprojection unit 10 illustrated in FIG. 22(*a*) can achieve the same effects as the microprojection unit 10 illustrated in FIGS. 11 to 13. In the microprojection unit 10 illustrated in FIG. 22(*b*), the shape of the contour 4L of the base component 4 is circular, and there are a total of twenty-one protrusions 3 arranged on the upper surface of the sheet-like base 2, wherein a single protrusion 3 is arranged at the center of the contour 4L, and a plurality of protrusions 3 are arranged with intervals therebetween on a plurality of circles spreading out concentrically from the single protrusion 3. The microprojection unit 10 illustrated in FIG. 22(*b*) has further improved puncturability, since the protrusions 3 are arranged on concentric circles.

Figure 22:
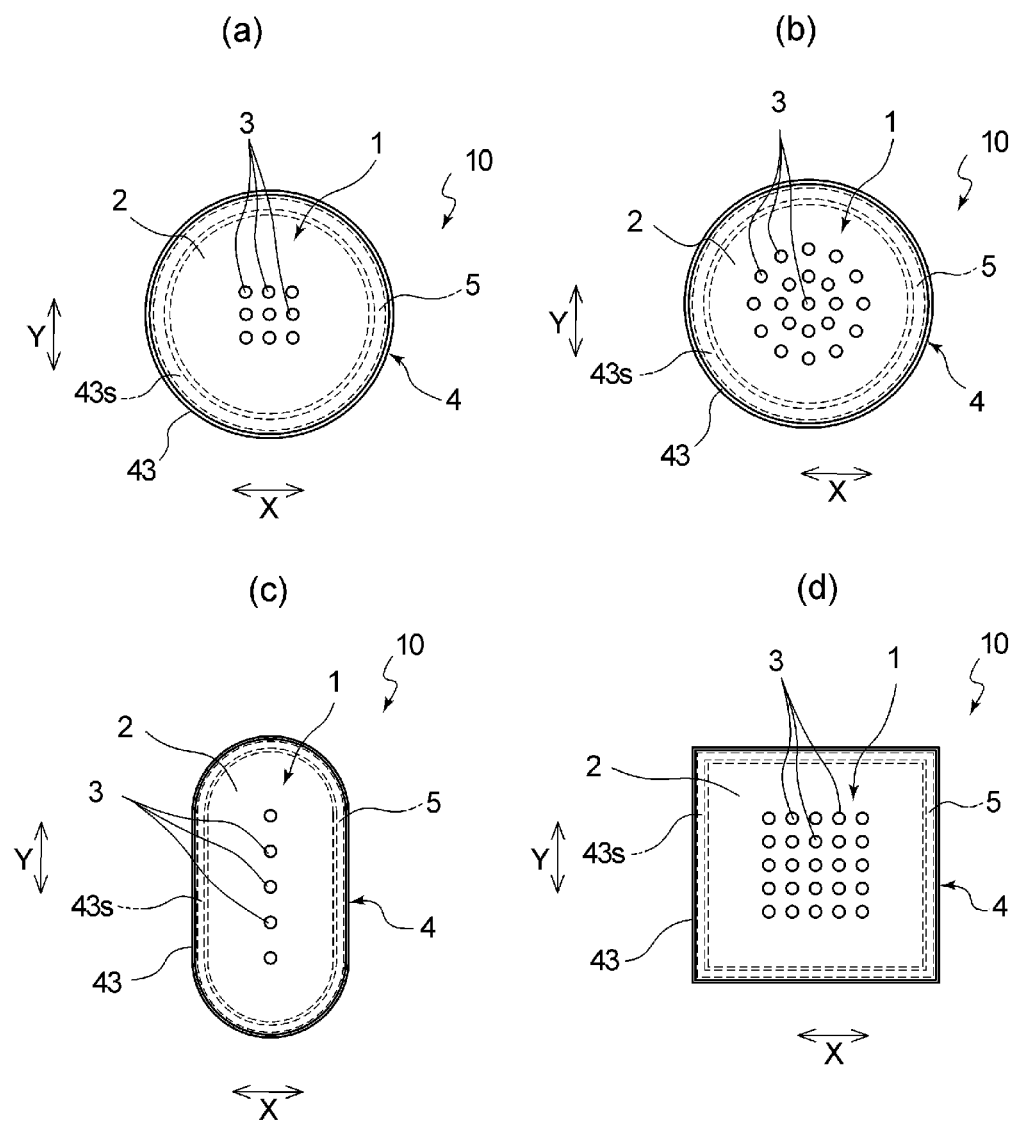
FIGS. 22(a) to 22(d) are plan views of microprojection units according to other embodiments in a planar view from the microprojection tool side.

In the microprojection unit 10 illustrated in FIG. 22(*c*), the shape of the contour 4L of the base component 4 is oval, and five protrusions 3 are arranged on the upper surface of the sheet-like base 2 in a single row with intervals therebetween along the direction in which the oval extends. The microprojection unit 10 illustrated in FIG. 22(*c*) has further improved puncturability, since the protrusions 3 are arranged in a single row. In the microprojection unit 10 illustrated in FIG. 22(*d*), the shape of the contour 4L of the base component 4 is rectangular, and twenty-five protrusions 3 are arranged on the upper surface of the sheet-like base 2 in five rows in the longitudinal direction Y and five rows in the lateral direction X. The microprojection unit 10 illustrated in FIG. 22(*d*) can achieve the same effects as the microprojection unit 10 illustrated in FIGS. 11 to 13. The shape of the contour 4L of the base component 4 may be polygonal, such as rhombic or triangular, other than rectangular.

In relation to the foregoing embodiments, the present invention further discloses the following microprojection unit manufacturing methods.

{1}

A method for manufacturing a microprojection unit that includes a microprojection tool including, on a base, a protrusion with a hollow interior, and a base component having a liquid retention space that is in communication with the interior of the protrusion through the base, the microprojection tool being joined to a tip end of the base component, the manufacturing method comprising:

a microprojection tool forming step of forming the microprojection tool by bringing a projecting mold part into contact from one surface side of a base sheet including a thermoplastic resin, and thus forming a protrusion that protrudes from another surface side of the base sheet, and withdrawing the projecting mold part from the interior of the protrusion; a joining step of joining the one surface side of the base sheet, in which the microprojection tool has been formed, and the tip end of the base component; and a cutting step of cutting the base sheet, to which the base component has been joined, along a contour of the base component at a position more inward than the base component's contour in a planar view of the base sheet as viewed from the microprojection tool side, to manufacture the microprojection unit.

{2}

The method for manufacturing a microprojection unit as set forth in clause {1}, wherein:

the base component includes a peripheral wall portion around an outer periphery of the liquid retention space; and in the cutting step, the base sheet is cut on a tip-end wall portion of the peripheral wall portion of the base component.

{3}

The method for manufacturing a microprojection unit as set forth in clause {1} or {2}, wherein a means for joining in the joining step is heat sealing, ultrasound, a laser, or an adhesive.

{4}

The method for manufacturing a microprojection unit as set forth in any one of clauses {1} to {3}, wherein a means for cutting in the cutting step is a punching blade or a laser.

{5}

The method for manufacturing a microprojection unit as set forth in any one of clauses {1} to {4}, wherein:

in the joining step, a first lower opening plate arranged on the one surface side of the base sheet and a first upper opening plate arranged on the other surface side of the base sheet are used, and joining is performed in a state where the base sheet, in which the microprojection tool has been formed, is sandwiched between the first lower opening plate and the first upper opening plate; and after the joining step, the first lower opening plate is moved downward and the first upper opening plate is moved upward.

{6}

The method for manufacturing a microprojection unit as set forth in any one of clauses {1} to {5}, wherein:

in the cutting step, a second lower opening plate arranged on the one surface side of the base sheet and a second upper opening plate arranged on the other surface side of the base sheet are used, and the microprojection unit is manufactured in a state where the base sheet, to which the base component has been joined, is sandwiched between the second lower opening plate and the second upper opening plate; and after the cutting step, the second lower opening plate is moved downward and the second upper opening plate is moved upward.

{7}

A method for manufacturing a microprojection unit that includes a microprojection tool including, on a base, a protrusion with a hollow interior, and a base component having a liquid retention space that is in communication with the interior of the protrusion through the base, the microprojection tool being joined to a tip end of the base component, the manufacturing method comprising:

a microprojection tool forming step of forming the microprojection tool by bringing a projecting mold part into contact from one surface side of a base sheet including a thermoplastic resin, and thus forming a protrusion that protrudes from another surface side of the base sheet, and withdrawing the projecting mold part from the interior of the protrusion; and a joining-cutting step of joining the one surface side of the base sheet, in which the microprojection tool has been formed, and the tip end of the base component, and simultaneously cutting the base sheet, along a contour of the base component at a position more inward than the base component's contour in a planar view of the base sheet as viewed from the microprojection tool side, to manufacture the microprojection unit.

{8}
The method for manufacturing a microprojection unit as set forth in clause {7}, wherein:
in the joining-cutting step, a third lower opening plate arranged on the one surface side of the base sheet and a third upper opening plate arranged on the other surface side of the base sheet are used, and the microprojection unit is manufactured in a state where the base sheet, in which the protrusion has been formed, is sandwiched between the third lower opening plate and the third upper opening plate; and
after the joining-cutting step, the third lower opening plate is moved downward and the third upper opening plate is moved upward.

{9}
The method for manufacturing a microprojection unit as set forth in any one of clauses {1} to {8}, wherein a continuous base sheet is transported intermittently by: paying out the continuous base sheet from a material roll of the base sheet; transporting the base sheet in a transporting direction; and stopping transportation of the base sheet when the base sheet has been fed to a predetermined position.

{10}
The method for manufacturing a microprojection unit as set forth in any one of clauses {1} to {9}, wherein, in the microprojection tool forming step:
the projecting mold part is brought into contact from the one surface side of the continuous base sheet being transported in the transporting direction; and
while softening, with heat, a contact section in the base sheet where the projecting mold part contacts the base sheet, the projecting mold part is inserted into the base sheet, to form the protrusion that protrudes from the other surface side of the base sheet.

{11}
The method for manufacturing a microprojection unit as set forth in clause {10}, wherein a heating temperature of the base sheet by heating with the projecting mold part is preferably equal to or higher than the glass transition temperature of the base sheet being used to below the melting temperature thereof, and more preferably equal to or higher than the softening temperature to below the melting temperature thereof.

{12}
The method for manufacturing a microprojection unit as set forth in clause {10} or {11}, wherein the heating temperature is preferably 30° C. or higher, more preferably 40° C. or higher, and preferably 300° C. or lower, more preferably 250° C. or lower, and more specifically, preferably from 30° C. to 300° C., more preferably from 40° C. to 250° C.

{13}
The method for manufacturing a microprojection unit as set forth in any one of clauses {1} to {12}, wherein an insertion speed for inserting the projecting mold part into the base sheet is preferably 0.1 mm/second or greater, more preferably 1 mm/second or greater, and preferably 1000 mm/second or less, more preferably 800 mm/second or less, and more specifically, preferably from 0.1 to 1000 mm/second, more preferably from 1 to 800 mm/second.

{14}
The method for manufacturing a microprojection unit as set forth in any one of clauses {1} to {13}, wherein, in the microprojection tool forming step, after the step of forming the protrusion by using a manufacturing device, the protrusion is cooled by using a cold air blowing device in a state where the projecting mold part is inserted in the interior of the protrusion.

{15}
The method for manufacturing a microprojection unit as set forth in clause {14}, wherein the cooling step is performed in a state where the base sheet is sandwiched between an opening plate and a second opening plate. forming step.

{16}
The method for manufacturing a microprojection unit as set forth in clause {14} or {15}, wherein a temperature of the cold air being blown is preferably −50° C. or higher, more preferably −40° C. or higher, and preferably 26° C. or lower, more preferably 10° C. or lower, and more specifically, preferably from −50° C. to 26° C., more preferably from −40° C. to 10° C.

{17}
The method for manufacturing a microprojection unit as set forth in any one of clauses {14} to {16}, wherein a cooling time for cooling by blowing the cold air is preferably 0.01 seconds or greater, more preferably 0.5 seconds or greater, and preferably 60 seconds or less, more preferably 30 seconds or less, and more specifically, preferably from 0.01 to 60 seconds, more preferably from 0.5 to 30 seconds.

{18}
The method for manufacturing a microprojection unit as set forth in any one of clauses {1} to {17}, wherein the base component is held in a manner that an outer shape of the base component's bottom portion side is fitted in a depression of a base component fixing part and the tip-end wall portion of the base component's peripheral wall portion is exposed.

{19}
The method for manufacturing a microprojection unit as set forth in any one of clauses {1} to {18}, wherein:
in the microprojection unit manufacturing method, heating is performed at an annular ring-shaped tip-end portion of a joining section in a state where the base sheet, in which the microprojection tool has been formed, is sandwiched between a first lower opening plate and a first upper opening plate; and
the one surface side (lower surface side) of the base sheet, in which the microprojection tool has been formed, and the tip end of the base component are joined together by forming a joined region in the microprojection unit while causing the base component's tip-end wall portion and a portion of the base sheet located on the tip-end wall portion of the base component's peripheral wall portion to melt.

{20}
The method for manufacturing a microprojection unit as set forth in clause {19}, wherein a heating temperature when causing the joining section to contact the base sheet is preferably 100° C. or higher, more preferably 120° C. or higher, and preferably 300° C. or lower, more preferably 250° C. or lower, and more specifically, preferably from 100° C. to 300° C., more preferably from 120° C. to 250° C.

{21}
The method for manufacturing a microprojection unit as set forth in clause {19} or {20}, wherein a heating time when causing the joining section to contact the base sheet is preferably 0.1 seconds or greater, and preferably 5.0 seconds or less, and more specifically, preferably from 0.1 to 5.0 seconds.

{22}
The method for manufacturing a microprojection unit as set forth in any one of clauses {19} to {21}, wherein a pressing force (pressurizing force) when causing the joining section to contact the base sheet is preferably 10 N or greater, and preferably 100 N or less, and more specifically, preferably from 10 to 100 N.

{23}

The method for manufacturing a microprojection unit as set forth in any one of clauses {19} to {22}, wherein, after the joining step, the joining section is moved upward, in a thickness direction, from the other surface side (upper surface side) of the base sheet, the first lower opening plate is moved downward, and the first upper opening plate is moved upward.

{24}

The method for manufacturing a microprojection unit as set forth in any one of clauses {1} to {23}, wherein:

a cutting section is passed through an opening of a second upper opening plate from the other surface side (upper surface side) of the base sheet in a state where the base sheet, to which the base component has been joined, is sandwiched between a second lower opening plate and the second upper opening plate; and the microprojection unit is manufactured by bringing a blade at a tip-end portion of the cutting section into contact with the other surface of the base sheet to cut the base sheet along the contour of the base component at a position more inward than the base component's contour in a planar view from the microprojection tool side.

{25}

The method for manufacturing a microprojection unit as set forth in clause {24}, wherein:

after the cutting step, the cutting section is moved upward, in the thickness direction, from the other surface side (upper surface side) of the base sheet, the second lower opening plate is moved downward, and the second upper opening plate is moved upward; and then, a trimmed portion of the base sheet sandwiched between the second lower opening plate and the second upper opening plate is removed after moving the second lower opening plate downward and moving the second upper opening plate upward.

In relation to the foregoing embodiments, the present invention further discloses the following microprojection units.

{26}

A microprojection unit comprising:

a microprojection tool including, on a base, a protrusion with a hollow interior; and a base component having a liquid retention space that is in communication with the interior of the protrusion through the base, the microprojection tool being joined to a tip end of the base component, wherein when a liquid is introduced into the liquid retention space of the base component and inner pressure is applied, a region where the protrusion is provided in the microprojection tool's base bends so as to project outward.

{27}

The microprojection unit as set forth in clause {26}, wherein, in a cross-sectional view of the microprojection unit along a thickness direction, a thickness of the base of the microprojection tool is smaller than a length, in the thickness direction, of the base component in a joined region where the base component and the microprojection tool have been joined together.

{28}

The microprojection unit as set forth in clause {26} or {27}, wherein:

the base component includes a bottom portion surrounding the liquid retention space, and a peripheral wall portion arranged so as to extend over an entire outer periphery of the bottom portion; and a thickness of the bottom portion is greater than the thickness of the base. {29}

The microprojection unit as set forth in clause {28}, wherein a thickness of the peripheral wall portion is greater than the thickness of the base.

{30}

The microprojection unit as set forth in any one of clauses {26} to {29}, wherein:

the microprojection tool has an opening on a tip-end side; and the microprojection tool has a shape in which a space penetrating from the base to the opening is formed in the interior of the protrusion.

{31}

The microprojection unit as set forth in any one of clauses {26} to {30}, wherein the protrusion has a protrusion height of preferably 0.01 mm or greater, more preferably 0.02 mm or greater, and preferably 10 mm or less, more preferably 5 mm or less, even more preferably 3 mm or less, and more specifically, preferably from 0.01 to 10 mm, more preferably from 0.01 to 5 mm, even more preferably from 0.02 to 3 mm.

{32}

The microprojection unit as set forth in any one of clauses {26} to {31}, wherein the protrusion has an average thickness of preferably 0.005 mm or greater, more preferably 0.01 mm or greater, and preferably 1.0 mm or less, more preferably 0.5 mm or less, and more specifically, preferably from 0.005 to 1.0 mm, more preferably from 0.01 to 0.5 mm.

{33}

The microprojection unit as set forth in any one of clauses {26} to {32}, wherein the protrusion has a tip end diameter of preferably 0.001 mm or greater, more preferably 0.005 mm or greater, and preferably 0.5 mm or less, more preferably 0.3 mm or less, and more specifically, preferably from 0.001 to 0.5 mm, more preferably from 0.005 to 0.3 mm.

{34}

The microprojection unit as set forth in any one of clauses {26} to {33}, wherein:

the microprojection tool has an opening on a tip-end side; and the opening has an opening area of preferably 0.7 $\mu m^2$ or greater, more preferably 20 $\mu m^2$ or greater, and preferably 200000 $\mu m^2$ or less, more preferably 70000 $\mu m^2$ or less, and more specifically, preferably from 0.7 to 200000 $\mu m^2$, more preferably from 20 to 70000 $\mu m^2$.

{35}

The microprojection unit as set forth in any one of clauses {26} to {34}, wherein a ratio (T2/T3) of the thickness T2 of the base to the thickness T3 of the bottom portion of the base component is preferably 0.001 or greater, more preferably 0.01 or greater, and preferably 1 or less, more preferably 0.5 or less, and preferably from 0.001 to 1, more preferably from 0.01 to 0.5.

{36}

The microprojection unit as set forth in any one of clauses {26} to {35}, wherein the thickness of the base is preferably 0.01 mm or greater, more preferably 0.02 mm or greater, and preferably 1.0 mm or less, more preferably 0.7 mm or less, and more specifically, preferably from 0.01 to 1.0 mm, more preferably from 0.02 to 0.7 mm.

{37}

The microprojection unit as set forth in any one of clauses {26} to {36}, wherein:

the base component includes a bottom portion surrounding the liquid retention space, and a peripheral wall portion arranged so as to extend over an entire outer periphery of the bottom portion; and the thickness of the bottom portion of the base component is preferably 1.0 mm or greater, more preferably 1.5 mm or greater, and preferably 10 mm or less, more preferably 5 mm or less, and more specifically, preferably from 1.0 to 10 mm, more preferably from 1.5 to 5 mm.

{38}

The microprojection unit as set forth in any one of clauses {26} to {37}, wherein:

the base component includes a bottom portion surrounding the liquid retention space, and a peripheral wall portion arranged so as to extend over an entire outer periphery of the bottom portion; and the thickness of the peripheral wall portion of the base component is preferably 1.0 mm or greater, more preferably 1.5 mm or greater, and preferably 10 mm or less, more preferably 5 mm or less, and more specifically, preferably from 1.0 to 10 mm, more preferably from 1.5 to 5 mm.

{39}

The microprojection unit as set forth in any one of clauses {26} to {38}, wherein, in a cross-sectional view of the microprojection unit along the thickness direction, a ratio (T2/L1) of the thickness T2 of the base of the microprojection tool to the length L1, in the thickness direction, of the base component is preferably 0.005 or greater, more preferably 0.01 or greater, and preferably 0.5 or less, more preferably 0.3 or less, and preferably from 0.005 to 0.5, more preferably from 0.01 to 0.3, in a joined region where the base component and the microprojection tool have been joined together.

{40}

The microprojection unit as set forth in any one of clauses {26} to {39}, wherein the length, in the thickness direction, of the base component is preferably 2 mm or greater, more preferably 3 mm or greater, and preferably 20 mm or less, more preferably 15 mm or less, and more specifically, preferably from 2 to 20 mm, more preferably from 3 to 15 mm.

{41}

The microprojection unit as set forth in any one of clauses {26} to {40}, wherein a contour of the base of the microprojection tool is arranged on an inner side of a contour of the base component with a spacing therebetween of preferably 0.05 mm or greater, more preferably 0.1 mm or greater, and preferably 5 mm or less, more preferably 3 mm or less, and more specifically, preferably from 0.05 to 5 mm, more preferably from 0.1 to 3 mm.

{42}

The microprojection unit as set forth in any one of clauses {26} to {41}, wherein:

in the microprojection unit, the base component and microprojection tool are joined together by a continuous joined region; and the continuous joined region has a width of preferably 0.5 mm or greater, more preferably 1 mm or greater, and preferably 5 mm or less, more preferably 3 mm or less, and more specifically, preferably from 0.5 to 5 mm, more preferably from 1 to 3 mm.

{43}

The microprojection unit as set forth in any one of clauses {26} to {42}, wherein:

in the microprojection unit, the base component and the microprojection tool are joined together by a continuous joined region; and the contour of the base and an outer-side peripheral edge of the joined region are arranged with a spacing therebetween of preferably 0.05 mm or greater, more preferably 0.1 mm or greater, and preferably 5 mm or less, more preferably 3 mm or less, and more specifically, preferably from 0.05 to 5 mm, more preferably from 0.1 to 3 mm.

{44}

The microprojection unit as set forth in any one of clauses {26} to {43}, wherein: the base component includes a bottom portion surrounding the liquid retention space, and a peripheral wall portion arranged so as to extend over an entire outer periphery of the bottom portion;

the base component and the microprojection tool are joined together by a continuous joined region; and in the microprojection unit, an inner-side peripheral edge of the joined region on a protrusion region 3R side and an inner wall of a tip-end wall portion of the peripheral wall portion are arranged with a spacing therebetween of preferably 0.05 mm or greater, more preferably 0.1 mm or greater, and preferably 5 mm or less, more preferably 3 mm or less, and more specifically, preferably from 0.05 to 5 mm, more preferably from 0.1 to 3 mm.

INDUSTRIAL APPLICABILITY

According to the present invention, it is possible to efficiently and accurately manufacture a microprojection unit that includes a microprojection tool and a base component with less restriction on the shape of the microprojection tool and the base component.

Further, according to the present invention, puncturability is improved and thus the feel upon use is improved, with less restriction on the shape of the microprojection tool and the base component.

The invention claimed is:

1. A method for manufacturing a microprojection unit that includes
a microprojection tool, and
a base component, which is a member separate from the microprojection tool, the microprojection tool joined to a tip end of the base component,
the microprojection tool including a base and a protrusion provided so as to stand up on an upper surface of the base,
a base component having a liquid retention space in communication with the interior of the protrusion through the base,
the manufacturing method comprising:
a microprojection tool forming step including:
bringing a projecting mold part into contact from one surface side of a base sheet including a thermoplastic resin, and thus forming a protrusion that protrudes from another surface side of the base sheet, and
withdrawing the projecting mold part from the interior of the protrusion;
a joining step of joining:
the one surface side of the base sheet, in which the microprojection tool has been formed, and
the tip end of the base component; and
a cutting step of cutting the base sheet, to which the base component has been joined, along a contour of the base component at a position more inward than the base component's contour in a planar view of the base sheet as viewed from the microprojection tool side, to manufacture the microprojection unit; and wherein the one surface side of the base sheet, in which the microprojection tool has been formed, and the tip end of the base component are joined together by forming a continuous joined region in the microprojection unit while causing the base component's tip-end wall portion and a portion of the base sheet located on the tip-end wall portion of the base component's peripheral wall portion to melt, and wherein a width of the continuous joined region in a planar view from the microprojection tool side is from 1 to 3 mm, or wherein the one surface side of the base sheet, in which the microprojection tool has been formed, and the tip end of the base component are joined together by forming a continuous joined region in the microprojection unit while causing the base component's tip-end wall portion and a portion of the base sheet located on the tip-end wall portion of the base component's peripheral wall portion to melt, and wherein a spacing between the contour of the base of the microprojection tool and an outer-side peripheral edge of the continuous joined region is from 0.1 to 3 mm, or wherein the one surface side of the base sheet, in which the microprojection tool has been formed, and the tip end of the base component are joined together by forming a continuous joined region in the microprojection unit while causing the base component's tip-end wall portion and a portion of the base sheet located on the tip-end wall portion of the base component's peripheral wall portion to melt, and wherein a spacing between an inner-side peripheral edge of the continuous joined region and an inner wall of a tip-end wall portion of a peripheral wall portion of the base component is from 0.1 to 3 mm.

2. The method for manufacturing a microprojection unit according to claim 1, wherein:
the base component includes a peripheral wall portion around an outer periphery of the liquid retention space; and
in the cutting step, the base sheet is cut on a tip-end wall portion of the peripheral wall portion of the base component.

3. The method for manufacturing a microprojection unit according to claim 1, wherein the joining step includes joining with heat sealing, ultrasound, a laser, or an adhesive.

4. The method for manufacturing a microprojection unit according to claim 1, wherein the cutting step includes cutting with a punching blade or a laser.

5. The method for manufacturing a microprojection unit according to claim 1, wherein:
in the joining step, a first lower opening plate is arranged on the one surface side of the base sheet and a first upper opening plate is arranged on the other surface side of the base sheet, and joining is performed in a state where the base sheet, in which the microprojection tool has been formed, is sandwiched between the first lower opening plate and the first upper opening plate; and
after the joining step, the first lower opening plate is moved downward and the first upper opening plate is moved upward.

6. The method for manufacturing a microprojection unit according to claim 1, wherein, in the joining step, a base component fixing part is arranged on the one surface side of the base sheet, and the base component is held in a manner that an outer shape of the base component's bottom portion side is fitted in a depression of the base component fixing part and the tip-end wall portion of the base component's peripheral wall portion is exposed.

7. The method for manufacturing a microprojection unit according to claim 1, wherein:
in the joining step, a first lower opening plate is arranged on the one surface side of the base sheet, a first upper opening plate is arranged on the other surface side of the base sheet, and a joining member is arranged on the other surface side of the base sheet, and heating is performed at a tip-end portion of the joining member in a state where the base sheet, in which the microprojection tool has been formed, is sandwiched between the first lower opening plate and the first upper opening plate.

8. The method for manufacturing a microprojection unit according to claim 7, wherein a heating temperature when the joining member contacts the base sheet is from 100° C. to 300° C.

9. The method for manufacturing a microprojection unit according to claim 7, wherein a heating time when the joining member contacts the base sheet is from 0.1 to 5.0 seconds.

10. The method for manufacturing a microprojection unit according to claim 7, wherein, after the joining step, the joining member is moved upward, in a thickness direction, from the other surface side of the base sheet, the first lower opening plate is moved downward, and the first upper opening plate is moved upward.

11. The method for manufacturing a microprojection unit according to claim 1, wherein:
in the cutting step, a second lower opening plate is arranged on the one surface side of the base sheet and a second upper opening plate is arranged on the other surface side of the base sheet, and the microprojection unit is manufactured in a state where the base sheet, to which the base component has been joined, is sandwiched between the second lower opening plate and the second upper opening plate; and
after the cutting step, the second lower opening plate is moved downward and the second upper opening plate is moved upward.

12. The method for manufacturing a microprojection unit according to claim 1, wherein:
in the cutting step, a second lower opening plate is arranged on the one surface side of the base sheet, a second upper opening plate is arranged on the other surface side of the base sheet, and a cutting section is arranged on the other surface side of the base sheet, and the cutting section is passed through an opening of the second upper opening plate from the other surface side of the base sheet in a state where the base sheet, to which the base component has been joined, is sandwiched between the second lower opening plate and the second upper opening plate; and
the microprojection unit is manufactured by bringing a blade at a tip-end portion of the cutting section into contact with the other surface of the base sheet to cut the base sheet along the contour of the base component at a position more inward than the base component's contour in a planar view from the microprojection tool side.

13. The method for manufacturing a microprojection unit according to claim 12, wherein:
    after the cutting step, the cutting section is moved upward, in the thickness direction, from the other surface side of the base sheet, the second lower opening plate is moved downward, and the second upper opening plate is moved upward; and
    then, a trimmed portion of the base sheet sandwiched between the second lower opening plate and the second upper opening plate is removed after moving the second lower opening plate downward and moving the second upper opening plate upward.

14. A method for manufacturing a microprojection unit that includes
    a microprojection tool, and
    a base component, which is a member separate from the microprojection tool, the microprojection tool being joined to a tip end of the base component,
    the microprojection tool including a base and a protrusion provided so as to stand up on an upper surface of the base,
    a base component having a liquid retention space in communication with the interior of the protrusion through the base,
    the manufacturing method comprising:
    a microprojection tool forming step including
    bringing a projecting mold part into contact from one surface side of a base sheet including a thermoplastic resin, and thus forming a protrusion that protrudes from another surface side of the base sheet, and
    withdrawing the projecting mold part from the interior of the protrusion; and
    a joining-cutting step of joining the one surface side of the base sheet, in which the microprojection tool has been formed, and the tip end of the base component, and simultaneously cutting the base sheet, along a contour of the base component at a position more inward than the base component's contour in a planar view of the base sheet as viewed from the microprojection tool side, to manufacture the microprojection unit; and
    wherein the one surface side of the base sheet, in which the microprojection tool has been formed, and the tip end of the base component are joined together by forming a continuous joined region in the microprojection unit while causing the base component's tip-end wall portion and a portion of the base sheet located on the tip-end wall portion of the base component's peripheral wall portion to melt, and wherein a width of the continuous joined region in a planar view from the microprojection tool side is from 1 to 3 mm, or
    wherein the one surface side of the base sheet, in which the microprojection tool has been formed, and the tip end of the base component are joined together by forming a continuous joined region in the microprojection unit while causing the base component's tip-end wall portion and a portion of the base sheet located on the tip-end wall portion of the base component's peripheral wall portion to melt, and wherein a spacing between the contour of the base of the microprojection tool and an outer-side peripheral edge of the continuous joined region is from 0.1 to 3 mm, or
    wherein the one surface side of the base sheet, in which the microprojection tool has been formed, and the tip end of the base component are joined together by forming a continuous joined region in the microprojection unit while causing the base component's tip-end wall portion and a portion of the base sheet located on the tip-end wall portion of the base component's peripheral wall portion to melt, and wherein a spacing between an inner-side peripheral edge of the continuous joined region and an inner wall of a tip-end wall portion of a peripheral wall portion of the base component is from 0.1 to 3 mm.

15. The method for manufacturing a microprojection unit according to claim 14, wherein:
    in the joining-cutting step, a third lower opening plate is arranged on the one surface side of the base sheet and a third upper opening plate is arranged on the other surface side of the base sheet, and the microprojection unit is manufactured in a state where the base sheet, in which the protrusion has been formed, is sandwiched between the third lower opening plate and the third upper opening plate; and
    after the joining-cutting step, the third lower opening plate is moved downward and the third upper opening plate is moved upward.

16. The method for manufacturing a microprojection unit according to claim 1, wherein a continuous base sheet is transported intermittently by: paying out the continuous base sheet from a material roll of the base sheet; transporting the base sheet in a transporting direction; and stopping transportation of the base sheet when the base sheet has been fed to a predetermined position.

17. The method for manufacturing a microprojection unit according to claim 1, wherein the method further comprises forming an opening in a vicinity of a tip of the protrusion by bringing the projection mold part into contact from one surface side a base sheet including a thermoplastic resin until it penetrates the base sheet.

18. The method for manufacturing a microprojection unit according to claim 1, wherein the base sheet and the base component each contain a thermoplastic resin and the joining of the one surface side of the base sheet, in which the microprojection tool has been formed, and
    the tip end of the base component comprises fusion-bonding.

19. The method for manufacturing a microprojection unit according to claim 1, wherein the method further comprises providing an ultrasonic vibration device which heats the projecting mold part.

20. The method for manufacturing a microprojection unit according to claim 19, wherein the ultrasonic vibration device heats the projection mold part to a temperature that is equal to or higher than the softening temperature of the base sheet and below the melting temperature of the base sheet.

* * * * *